(12) United States Patent
Yoo

(10) Patent No.: US 8,101,356 B2
(45) Date of Patent: *Jan. 24, 2012

(54) NUCLEIC ACID HYBRIDIZATION ASSAY METHOD

(75) Inventor: Jae Chern Yoo, Pohang (KR)

(73) Assignee: Jae Chern Yoo, Kyungsangbuk-Do (KR)

( * ) Notice: Subject to any disclaimer, the term of this patent is extended or adjusted under 35 U.S.C. 154(b) by 15 days.

This patent is subject to a terminal disclaimer.

(21) Appl. No.: 12/585,513

(22) Filed: Sep. 16, 2009

(65) Prior Publication Data

US 2010/0129812 A1 May 27, 2010

Related U.S. Application Data

(62) Division of application No. 10/470,487, filed as application No. PCT/KR02/00126 on Jan. 28, 2002, now abandoned.

(30) Foreign Application Priority Data

Jan. 27, 2001 (KR) .................................. 2001-3956

(51) Int. Cl.
*C12Q 1/68* (2006.01)
(52) U.S. Cl. ........................................................ 435/6.1
(58) Field of Classification Search .................. None
See application file for complete search history.

(56) References Cited

U.S. PATENT DOCUMENTS

| | | | |
|---|---|---|---|
| 4,775,619 A | 10/1988 | Urdea | 435/6 |
| 5,118,605 A | 6/1992 | Urdea | 435/6 |
| 5,766,934 A | 6/1998 | Guiseppe-Elie | 435/287.9 |
| 6,047,259 A | 4/2000 | Campbell et al. | 705/3 |
| 6,300,070 B1 | 10/2001 | Boles et al. | 435/6 |
| 6,312,901 B2 | 11/2001 | Virtanen | 435/6 |
| 6,613,508 B1 | 9/2003 | Ness et al. | |

FOREIGN PATENT DOCUMENTS

KR 2001-0004339 1/2001

OTHER PUBLICATIONS

U.S. Office Action mailed Jan. 14, 2011 in related U.S. Appl. No. 12/585,504.
Final Office Action mailed Jan. 14, 2010 in U.S. Appl. No. 10/470,487.
U.S. Appl. No. 10/470,487, filed Jan. 28, 2002, Jae Chern Yoo.
U.S. Patent Office Action, mailed Sep. 14, 2006, issued in corresponding U.S. Appl. No. 10/470,487.
U.S. Patent Office Action, mailed Jan. 26, 2007, issued in corresponding U.S. Appl. No. 10/470,487.
U.S. Patent Office Action, mailed Aug. 7, 2007, issued in corresponding U.S. Appl. No. 10/470,487.
U.S. Patent Office Action, mailed Jan. 24, 2008, issued in corresponding U.S. Appl. No. 10/470,487.
U.S. Patent Office Action, mailed Sep. 2, 2008, issued in corresponding U.S. Appl. No. 10/470,487.
U.S. Patent Office Action, mailed Mar. 17, 2009, issued in corresponding U.S. Appl. No. 10/470,487.
U.S. Patent Office Action mailed Aug. 31, 2011 in corresponding U.S. Appl. No. 12/585,504.
Chrisey et al., Covalent attachment of synthetic DNA to self-assembly monolayer films, Nucleic Acids Res. (1996) 24:3031-3039.

*Primary Examiner* — Kenneth R. Horlick
*Assistant Examiner* — David Thomas
(74) *Attorney, Agent, or Firm* — Staas & Halsey LLP

(57) ABSTRACT

A cleavable signal element applicable to quantitative and qualitative assay devices, using a cleavable technique specifically responsive to a complementary double strand or single strand of nucleic acids, and a nucleic acid hybridization assay method and device using the cleavable signal element are provided. Using the cleavable technique responsive to the complementary double strand or single strand of nucleic acids, detection sensitivity to a target nucleic acid can be increased, and diagnosis and detection reliability can be improved twice through in-situ determinations. Through simultaneous single nucleotide polymorphism (SNP) detection and expression profile determination, more accurate diagnosis for many diseases can be achieved. The assay device can be easily modified to be suitable for detection with general laser-based detection systems such as CD-ROM readers. Information read from the assay device is digitized as software and transmitted to and received by doctors and patients through a computer network or wirelessly, which enables construction of remote diagnosis systems.

10 Claims, 29 Drawing Sheets

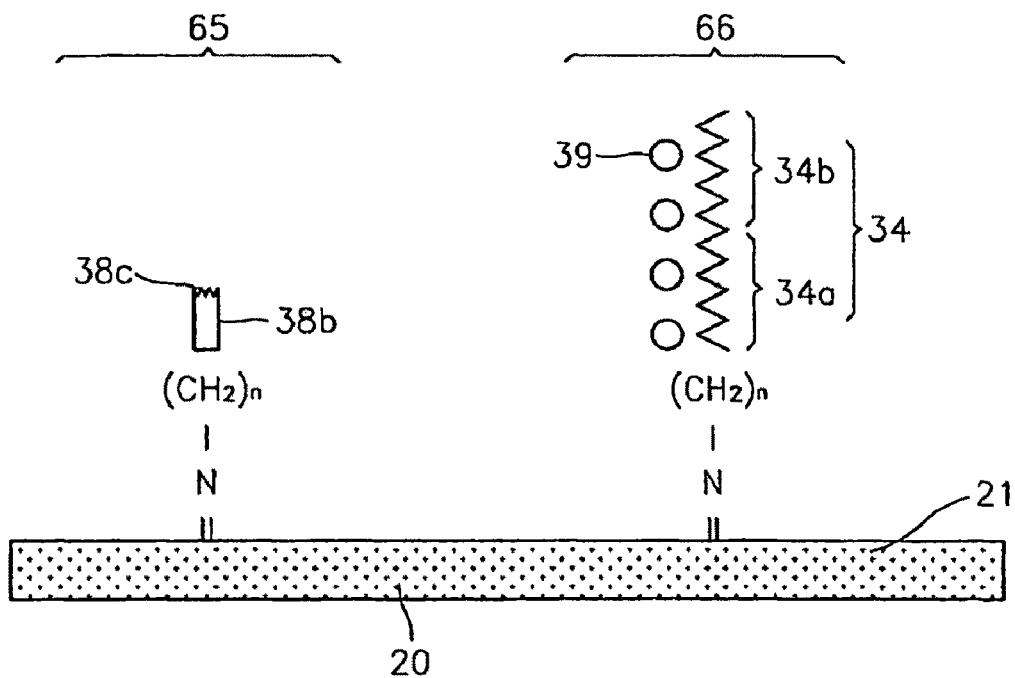
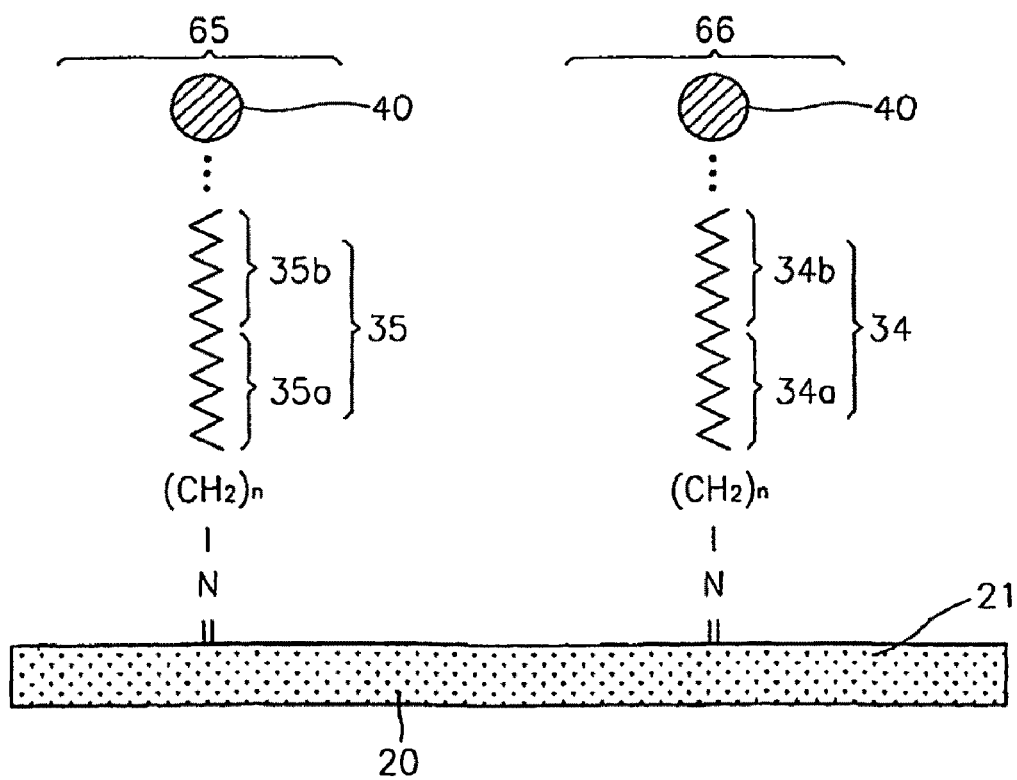

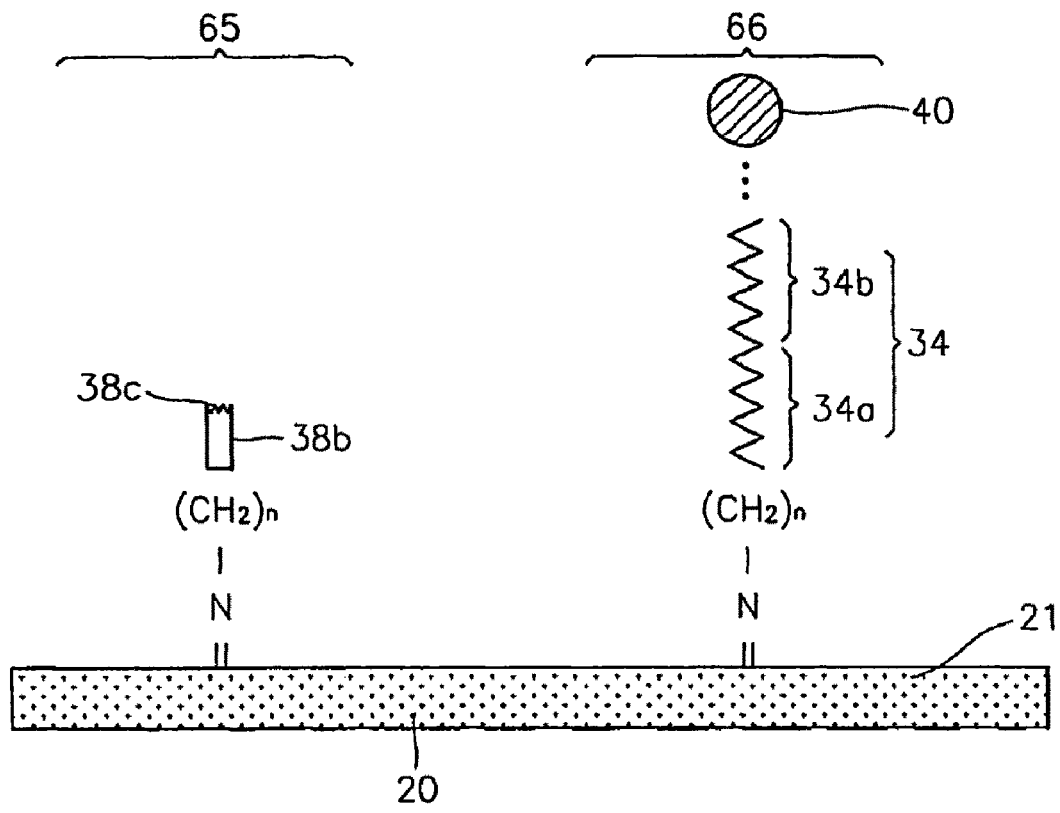
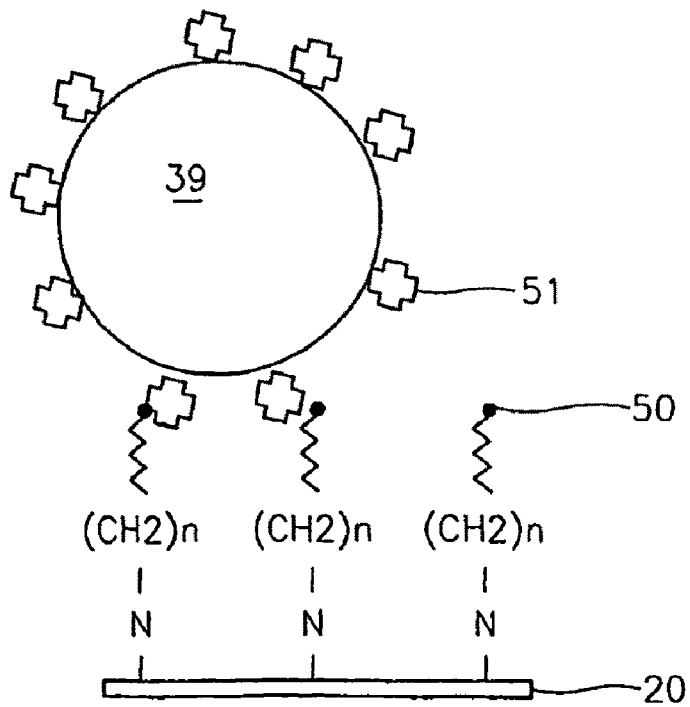

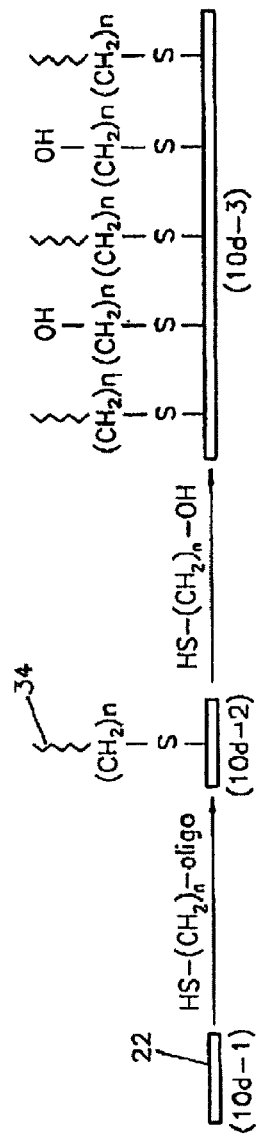
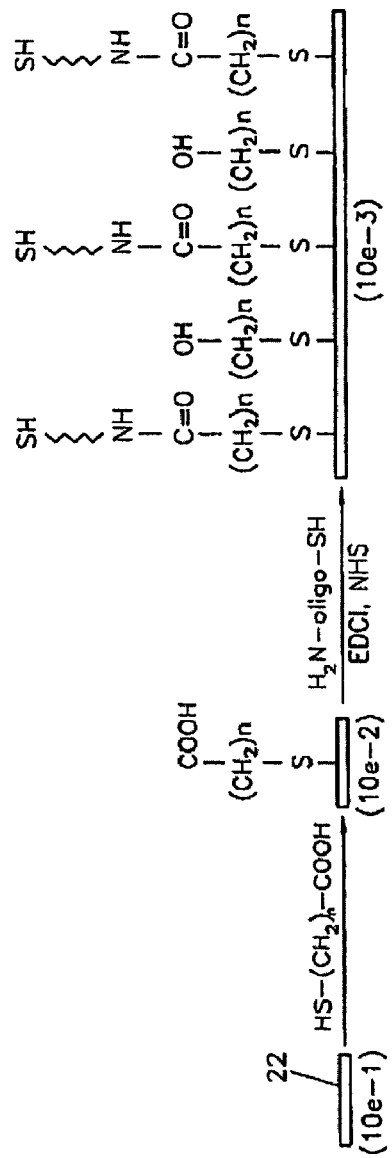
FIG. 10D
FIG. 10E

NUCLEIC ACID HYBRIDIZATION ASSAY METHOD

CROSS-REFERENCE TO RELATED APPLICATIONS

This application is a U.S. divisional application filed under 35 USC 1.53(b) claiming benefit of U.S. Ser. No. 10/470,487 filed in the United States on Feb. 17, 2004, now abandoned which claims earlier benefit of PCT Patent Application No. PCT/KR02/00126 filed Jan. 28, 2008 and also which claims earlier benefit of Korean Application No. 2001-3956 filed in Korea on Jan. 27, 2001, all of which this application hereby incorporates by reference.

TECHNICAL FIELD

The present invention relates to cleavable signal elements using a cleavage technique specifically responsive to a complementary double strand or single strand of nucleic acids, which are applicable to quantitative and qualitative assay devices, and a nucleic acid hybridization assay method and device using the cleavable signal element.

BACKGROUND ART

To date, most clinical diagnostic assays for the detection of small quantities of analytes in fluids have been conducted as individual tests; that is, as single tests conducted upon single samples to detect individual analytes. More recently, multiple-sample preparation and automated reagent addition devices and multiple-sample assay devices, either in parallel or in serial procession, have been designed to improve efficiency and economy. Such automated reagent preparation devices and automated multiplex analyzers are often integrated into a single device.

Large-scale clinical laboratory analyzers of this type can accurately perform hundreds of assays in one hour automatically or semi-automatically. However, these analyzers are expensive and only centralized laboratories and hospitals can afford them. Such centralization necessitates sample transport to the laboratory or hospital, and often precludes urgent or emergent analysis of time-critical samples.

Thus, to address these problems, there is an increasing need for clinical analyzers which are cheap and easy-to-handle for everyone, such as clinical analyzers suitable for use at the patient bedside or in the patient's home without dedicated detectors. Blood glucose and pregnancy testers are well known examples.

Although useful tests of this sort have been offered for many years, a major breakthrough was the introduction of solid phase immunoassays and other strip tests since 1980. Most notable are Advance® test (Johnson & Johnson), TAM™ hCG assay (Monoclonal Antibodies, Inc.), Clear Blue Easy™ (Unipath Ltd.), and ICON (Hybritech). Commercially Available are Quantab™ (Environmental Test Systems), AccuLevel® (Syva), AccuMeter® (ChemTrak), Clinimeter™ (Crystal Diagnostics), and Q.E.D.™ (Enxymatics). One of the newest is a thermometer-type assay device (Ertinghausen G., U.S. Pat. No. 5,087,556) that is not yet commercially available. These systems can be used to assay blood levels of therapeutic drugs and general chemical analytes such as cholesterols.

One disadvantage, however, of each of these formats is that only one, or a very limited number, of assays can conveniently be performed simultaneously.

To fill the gap between massive analyzers and strip testers, some small instruments have been developed. The most notable is Eclipse ICA™ (Biotope, Inc.). This device is an automated centrifugal immunoassay and chemistry system. Patient samples are pipetted into cassettes that are placed into a rotary device. Sixteen tests can be run in approximately 17 minutes. The results are measured by UV/Nisible spectrometry or by fluorometry.

Despite these developments, there still exists a need for a simple device that can easily be used for multiple quantitative assays without a specialized detector.

<Spatially Addressable Probe Assays>

Recently, spatially addressable arrays of different biomaterials have been fabricated on solid supports. These probe arrays permit the simultaneous analysis of a large number of analytes. Examples are arrays of oligonucleotides or peptides that are fixed to a solid support and that capture complementary analytes. One such system is described by Fodor et al., *Nature*, Vol. 364, Aug. 5, 1993. Short oligonucleotide probes attached to a solid support bind complementary sequences contained in longer strands of DNA in liquid sample; the sequence of the sample nucleic acids is then calculated by computer based on the hybridization data so collected.

There remains a need for an economical system to fabricate spatially addressable probe arrays in a simplified format that provides both for ready detection and the ability to assay for large numbers of test substances (i.e. analytes) in a fluid test sample in a single step, or a minimum number of steps, or assay for a single test substance or analyte in a large number of fluid test samples.

<Spatially Addressable Laser-Based Detection Systems>

Several devices permit spatially addressable detection of digital information. In particular, several formats have been developed based on differential reflectance and transmittance of recording information.

In conventional audio or CD-ROM compact disks, digital information or digitally encoded analog information is encoded on a circular plastic disk by means of indentations in the disk. Typically, such indentations are on the order of one-eighth to one-quarter of the wavelength of the incident beam of a laser that is used to read the information from the disk. The indentations on the disk cause destructive interference within the reflected beam, which corresponds to a bit having a "zero" value. The flat areas of the disk reflect the laser beam back to a detector and the detector gives a value of "one" to the corresponding bit.

In another convention, a change of intensity of a reflected light beam gets a value of one while a constant intensity corresponds to zero.

Since the indentations have been formed in the disk in a regular pattern from a master copy containing a predetermined distribution of bits of "zero" and bits of "one", the resultant signal received by the detector is able to be processed to reproduce the same information that was encoded in the master disk.

The standard compact disk is formed from a 12-cm polycarbonate substrate, a reflective metal layer, and a protective lacquer coating. The format of current CDs and CD-ROMs is described by the ISO 9660 industry standard.

The polycarbonate substrate is optical-quality clear polycarbonate. In a standard pressed, or mass-replicated CD, the data layer is part of the polycarbonate substrate, and the data are impressed in the form of a series of pits by a stamper during the injection molding process. The stamping master is typically glass.

Pits are continuously spirally impressed in the CD substrate. The reflective metal layer applied thereupon, typically aluminum, assumes the shape of the solid polycarbonate substrate, and differentially reflects the laser beam to the reading assembly depending on the presence or absence of "pits." An acrylic lacquer is spin-coated as a thin layer on top of the reflective metal layer to protect it from abrasion and corrosion.

Although similar in concept and compatible with CD readers, the information is recorded differently in a recordable compact disk (CD-R). In CD-R, the data layer is separate from the polycarbonate substrate. The polycarbonate substrate instead has impressed upon it a continuous spiral groove as an address for guiding the incident laser. An organic dye is used to form the data layer. Cyanine or a metal-stabilized cyanine compound is generally used to form the data layer. An alternative material is phthalocyanine. One such metallophthalocyanine compound is described in U.S. Pat. No. 5,580,696.

In CD-R, the organic dye layer is sandwiched between the polycarbonate substrate and the metallized reflective layer, usually 24 carat gold, but alternatively silver, of the media. Information is recorded by a recording laser of appropriate preselected wavelength that selectively melts "pits" into the dye layer, causing the pits to become non-translucent. The reading sensor reads the presence or absence of pits from refractivity rather than differential reflectivity by physical pits in the standard CD. As in a standard CD, a lacquer coating protects the information layer.

Other physical formats for recording and storing information have been developed based on the same concept as the compact disk: creation of differential reflectance or transmittance on a substrate to be read by laser. One such format is termed digital versatile disk (DVD). A DVD looks like standard CD: it is a 120-mm (4.75 inch) disk with a hole in the center for engaging a rotatable drive mechanism. Like a CD, data is recorded on the disk in a spiral trail of tiny pits, and the disks are read using a laser beam. In contrast to a CD, which can store approximately 680 million bytes of digital data under the ISO 9660 standard, the DVD can store from 4.7 billion to 17 billion bytes of digital data. The DVD's larger capacity is achieved by making the pits smaller and the spiral tighter, that is, by reducing the pitch of the spiral, and by recording the data in as many as four layers, two on each side of the disk. The smaller pit size and tighter pitch require that the reading laser wavelength be smaller. While the smaller wavelength is compatible with standard pressed CDs, it is incompatible with current versions of the dye-based CD-R.

Thus, a single sided/single layer DVD can contain 4.7 GB of digital information. A single sided/dual layer DVD can contain 8.5 GB of information. A Dual sided/single layer disk can contain 9.4 GB of information, while a dual sided/dual layer DVD contains up to 17 GB of information.

Depending on the capacity, the disk may have one to four information layers. In the 8.5 GB and 17 GB options, a semi-reflector is used in order to access two information layers from one side of the disk. For the 8.5 GB DVD and 17 GB options, the second information layer per side may be molded into the second substrate or may be added as a photopolymer layer. In either case, a semi-reflector layer is required to allow both information layers to be read from one side of the disk. For the 17 GB DVD, it is necessary to produce two dual-layer substrates, and bond them together.

The DVD laser reader is designed to adjust its focus to either layer depth so that both of them can be quickly and automatically accessed.

All of the above-described formats require that the disk be spun. The nominal constant linear velocity of a DVD system is 3.5 to 4.0 meters per second (slightly faster for the larger pits in the dual layer versions), which is over 3 times the speed of a standard CD, which is 1.2 mps.

<Detection Method of DNA Chips>

DNA chips refer to chips having highly immobilized DNA probes of interest on solid substrates and are used for the analysis of a gene expression profile, genetic defects, etc., in samples. To investigate whether the sample contains a target nucleic acid that binds to the probe immobilized on the substrate, a detection system therefor is required.

Most currently-available genetic analysis DNA chips employ a method of fluorescently labeling a sample DNA, reacting it with the proves immobilized on the chip, and detecting the unreacted fluorescent material remaining on the chip surface using a confocal microscope or charge coupled device (CCD) imager (U.S. Pat. No. 6,141,096). However, such optical detection method is disadvantageous in size reduction and cannot display digitized outputs. For these reasons, research on the development of a new detection method for electrical signal outputs is actively being conducted.

Many research institutes, including Clinical Micro Sensors, are researching the electrochemical detection of DNA hybridization using a metal compound that is liable to oxidation/reduction (U.S. Pat. Nos. 6,096,273, 6,090,933). Separate compounds containing easily oxidizable/reducible metals form a complex upon DNA hybridization, and the complex is electrochemically detected (*Anal. Chem.*, Vol., 70, pp. 4670-4677, 1998; *J. Am. Chem. Soc.*, Vol. 119, pp. 9861-9870, 1997; *Analytica Chemica Acta*, Vol, Vo. 2886, pp. 216-224, 1994; *Bioconjugate Chem.*, Vol. 8, pp. 906-913, 1997). However, this electrochemical method still needs separate labeling.

Approaches to assay methods not using the fluorescent label or any other labels have been actively made. As a result, a method of measuring a difference in mass before and after binding using a quartz crystal microbalance (*Anal. Chem.*, Vol. 70, pp, 1288-1296, 1998), an assay method using matrix assisted laser description ionization (MALDI) mass spectrometry (*Anal. Chem.*, Vol. 69, pp. 4540-4546, 1997, U.S. Pat. No. 6,043,031) were developed.

Even a single-base difference can be analyzed using a microfabricated cantilever, which is a mechanical sensor type for measuring molecular binding force before and after binding of DNA probe and target (*Science*, Vol., 288, pp. 316-318, 2000; *Proc. Natl., Acad. Sci. USA*, 98, 2560, 2001). However, this method needs additional equipment, such as a laser, for accurate measurement of cantilever beam deflection.

The present invention relates to the field of diagnosis and detection of small quantities of materials in fluids. It is an object of the present invention to provide cleavable signal elements using a cleavage technique specifically responsive to a double strand or single strand of nucleic acids or oligonucleotides having a complementary sequence, which are applicable to quantitative and qualitative assay devices, and a nucleic acid hybridization assay method and device using the cleavable signal element.

It is another object of the present invention to provide an accurate method and device of diagnosing a variety of diseases from both single nucleotide polymorphism (SNP) detection and gene expression profile obtained using the nucleic acid hybridization assay device.

An analytical apparatus based on the nucleic acid hybridization assay method and device using the cleavage technique can be modified to use the standard laser-based detection system, such as CD-ROM reader or DVD reader, and can be coupled to a detector including an optical device, an electrochemical device, or a capacitance and impedance measurement device. The analytical apparatus and method according to the present invention are useful in both detecting a number of individual analytes in a test sample and detecting a single analyte in a large number of separate samples.

It is still another object of the present invention is to provide a remote diagnostic system providing convenience to both patients and doctors by transmitting and receiving the information read from the analytical apparatus and digitalized as computer software, through an existing communication network, such as the Internet.

DISCLOSURE OF THE INVENTION

It is an object of the present invention to provide a nucleic acid hybridization assay method and device applicable to quantitative and qualitative assay devices, which use a cleavage technique specifically responsive to a complementary double strand of nucleic acids of a particular sequence.

In the present invention, cleavage is performed using a restriction enzyme specifically responsive to only a double strand of a particular sequence. Hereinafter, the particular sequence is referred to as a "restriction sequence", and each single strand of the restriction sequence is referred to as a "restriction probe". The restriction probe is additionally ligated to one end of a capture probe that has a complementary sequence to a target DNA and thus is hybridized to the target DNA, and then immobilized on a substrate. The restriction probe and capture probe can be designed collectively as a single probe. In forming a double strand from the capture probe and restriction probe, the restriction probe is cleaved by the restriction enzyme, and thus the restriction and capture probes are collectively referred to as "cleavable capture probes" or "cleavable signal elements".

Although use of the restriction enzyme that specifically responds to a restriction sequence of the designed restriction probe is well known in the field, it is preferable to design the restriction probe such that the sequence of the restriction probe ligated to one end of the capture probe does not overlap with the sequence of the capture probe.

The sequence of the capture probe is determined to be specific to an analyte of interest for diagnosis or analysis purpose. As the capture probe contacts a sample containing a target nucleic acid having a complementary sequence to the capture probe, the capture probe forms a double strand with the target nucleic acid through hybridization. At this time, the restriction probe attached to one end of the capture probe still remains as a single strand and does not form the double stand.

To form a double strand of the non-hybridized restriction probe, a solution mixture containing four dNTPs and a DNA polymerase required for DNA extension are added. Formation of a double-strand of the restriction probe is achieved through DNA extension using the target nucleic acid hybridized to the capture probe as a primer.

Once the cleavable capture probe forms a complete double strand through hybridization of the capture probe to the target nucleic acid and formation of the restriction probe double strand, the double-stranded restriction probe is cleavable by the restriction enzyme. After cleavage of the double strand by the restriction enzyme, the cleaved signal element is removed from the substrate through washing.

In contrast, when the capture probe contacts a sample that does not have a complementary nucleic acid sequence to the capture probe, the cleavable capture probe cannot form the double strand, so it remains attached to the substrate after the addition of the restriction enzyme and washing. The cleavable capture probe remaining on the substrate is referred to as an "uncleaved probe". To improve the sensitivity of a detector, a "label-attached uncleaved probe" structure can be optionally formed on the substrate by contacting the uncleaved probe with fluorescent labels or other labeling elements such as metal microspheres.

After sample-to-probe contact, reaction using the DNA polymerization solution and the restriction enzyme, and washing, detection of the presence or absence of the uncleaved probe or "label-attached uncleaved probe" structure on the substrate by a detector including an optical device, an electrochemical device, a mass measurement device, or a capacitance and impedance measurement device, indicates the presence or absence of a particular analyte.

As described above, "uncleaved probes (cleavable capture probes not cleaved and adhering to the substrate)" or "label-attached uncleaved probe" structures act as signal elements for the presence of particular analytes. The presence of the cleavable signal element (uncleaved signal element) on the substrate means that sample does not contain a particular analyte, and the absence of the cleavable signal element (cleaved signal element) from the substrate means that sample contains a particular analyte.

The present invention provides a nucleic acid hybridization assay method using the cleavable capture probe as a cleavable signal element.

In general, the assay method using the assay device and a cleavage technique specifically responsive to a particular sequence involves: contacting the assay device with a liquid sample; reacting the cleavable signal probe with a DNA polymerization solution to form a double strand; contacting the cleavable capture probe with a restriction enzyme to cleave the double strand; removing the cleaved double strand through washing; and detecting the presence or absence of the cleavable signal element on a solid support substrate using the detector including an optical device, an electrochemical device, a mass measurement device, or a capacitance and impedance measurement device, as described above.

After washing, a label may be optionally attached to the uncleaved probe remaining on the solid support substrate to form a "label-attached uncleaved probe" structure. This label attachment improves the sensitivity of the detector including an optical device, an electrochemical device, a mass measurement device, or a capacitance and impedance measurement device.

According to the present invention, the presence of a particular analyte can be double checked through two steps, thereby increasing assay reliability. As a first step, after contact with a sample, whether the capture probe is double-stranded or not with the target nucleic acid is determined. As a second step, after the reaction with the DNA polymerization solution, the restriction enzyme treatment, and the washing, whether the cleavable capture probe remains on the substrate or not is determined in situ. Therefore, the particular analyte can be detected with higher reliability.

In another aspect, the present invention provides an assay device comprising a solid support substrate on which a plurality of cleavable capture probes (cleavable signal elements) are deposited in a spatially-addressable pattern. Suitable materials for the solid support substrate of the assay device include gold, glass, and silicon, with polycarbonate being preferred. Alternative examples of the solid support substrate include disks of any shape compatible for detection using existing laser reflectance-based detectors, including audio compact disk (CD) readers, CD-ROM (compact disk read-only memory) readers, recordable CD readers, DVD (digital versatile disk) readers, and the like.

In a preferred embodiment of the present invention, an "uncleaved probe" or a "label-attached uncleaved probe"

structure and the cleaved double strand differentially reflect or scatter incident light, in particular, incident laser light, which can be adapted for detection using existing laser-reflectance based detectors, including CD readers, CD-R readers, CD-ROM readers, or DVD readers. Furthermore, according to the present invention, a bioinformatics-related database for diagnosis and assay interpretation, as well as hospital telephone numbers and web link information for remote diagnosis, may be loaded to a spatial address. In addition, the present invention enables personal medical history management by writing the diagnosis result to a CD-R or a hard disk.

The deposition of cleavable signal elements (cleavable capture probes) on the assay device in a spatially-addressable pattern permits a single-sample assay for multiple analytes, a multi-sample assay for a single analyte, and a multi-sample assay for multiple analytes.

Another aspect of the present invention provides a nucleic acid assay device including cleavable signal elements responsive to a variety of nucleic acid sequences. In view of this, the present invention provides an assay method and device for assaying a nucleic acid sequence present in a sample from the spatial address of a signal generated upon contact with the nucleic acid containing sample.

The present invention simultaneously provides single nucleotide polymorphism (SNP) detection and expression profile determination, thereby enabling more accurate diagnosis of many kinds of diseases.

Another aspect of the present invention provides a remote diagnostic system providing convenience to both patients and doctors, which detects a plurality of cleavable signal elements attached to a solid support substrate using the detector including an optical device, an electrochemical device, a mass measurement device, or a capacitance and impedance measurement device, digitizes the detected information as computer software, and transmits to both doctor and patient through an existing communication network, such as the Internet.

The assay device and method according to the present invention uses cleavable capture probes as cleavable signal elements for detection of analytes in fluid test samples. Binding of the analyte preselected for detection enables cleavage of the cleavable capture probe at its restriction probe portion and removal of the cleavable capture probe from the substrate surface.

When the sample does not contain the target nucleic acid, the cleavable capture probe remains attached to the substrate surface. Therefore, the presence or absence of the cleavable signal element (cleavable capture probe) can be used as digital (binary) information indicating whether a particular analyte exists or not in the sample. A differential signal between the uncleaved signal element and the cleaved signal element indicates whether the particular analyte exists or not in the sample.

In a preferred embodiment, the signal element according to the present invention reflects or scatters incident light and is light addressable. Binding of the analyte preselected for detection enables cleavage and removal of the signal element. Reflection or scattering of incident light, in particular, incident laser light, from the uncleaved signal element indicates the absence of a particular analyte in the sample, and reflection or scattering from the cleaved signal element indicates the presence of the analyte in the sample.

The cleavable signal elements of the present invention are particularly adapted for detection using existing laser reflectance-based detectors, including CD readers, CD-ROM readers, laser disk readers, DVD readers, and the like. The cleavable signal elements of the present invention thus permits the ready adaptation of existing assay chemistries and existing assay schemes to detection using-existing laser reflectance-base detectors. This leads to substantial cost savings per assay over standard assays using dedicated detectors.

Applicable assay examples are immunoassays, cell counting, genetic detection assays based upon hybridization, genetic detection assays based upon nucleic acid sequencing, nucleic acid sequencing itself, and the like. The present invention thus allows distribution of assay devices to research laboratories, physician's offices, and individual homes that must currently be performed at centralized locations.

The spatially addressable capabilities of the laser reflectance-based detectors currently used to detect and interpret information encoded on CDs and the like confer particular advantages on assays adapted to use the cleavable reflective signal elements of the present invention.

Thus, patterned deposition of multiple signal elements on a single support or substrate, coupled with use of a detector capable of addressing the spatial location of these individual signal elements, permits the concurrent assay of a single sample for multiple different analytes, multiple samples for a single analyte, or multiple samples for multiple analytes. The present invention is thus further directed to assay devices, commonly referred to herein as disk, bio-compact disks, bio-DCs, or bio-DVDs, comprising spatially addressable combinations (diverse geometries) of cleavable signal elements of different analyte specificity. Among such useful combinations are those that increase the predictive value or specificity of each of the individual assays, combinations that inculpate or exculpate particular diagnoses in a differential diagnosis, combinations that provide broad general screening tools, and the like.

Patterned deposition of multiple signal elements with identical specificity further permits the detection, using a single assay device, of large concentration ranges of a single analyte. It is thus another aspect of the present invention to provide assay devices comprising spatially addressable cleavable signal elements of identical specificity, the physical location of which is capable of conveying concentration information.

The spatially addressable capabilities of the laser reflectance-based digital detectors further permits the combination of interpretive software and the assay elements themselves on a single assay device. Another aspect of the present invention, therefore, is an assay device upon which software is encoded in an area spatially distinct from the patterned deposition of cleavable signal elements. The software may include information important for correct tracking by the incident laser, assay interpretive algorithms, standard control values, bioinformatics information, self-diagnostics, and the like. The software may include device drivers and software capable of uploading the diagnostic information to remote locations. The software may include educational information for patients on clinical assays, and may be adapted for chosen audiences. The software may include a variety of web sites and links, for example, a web site enabling a patient to communicate with a doctor or hospital based on his/her diagnosis result.

To increase detection sensitivity to reflection variations in the nucleic acid hybridization assay according to the present invention, one end of the cleavable capture probe (cleavable signal element) is covalently bound to the substrate, and the other end of the cleavable capture probe is labeled with, for example, a conducting polymer (e.g., polyaniline), a fluorescent label, or a metal microsphere, to form a label-attached signal element ("label-attached cleavable capture probe"), thereby increasing a reflectivity variation relative to the cleaved signal element.

In another preferred embodiment, the cleavable signal element according to the present invention provides information (signal) on the presence or absence of analytes in the sample to a capacitance and impedance measurement device for measuring conductance variations. Binding of the analyte preselected for detection enables removal of the cleavable signal element through cleavage. A conductance difference between the uncleaved signal element and the cleaved signal element signals whether the analyte exists or not in the sample. After washing, a "label-attached uncleaved probe" structure may be optionally formed on the substrate by contacting the uncleaved signal element with a label, such as a metal microsphere, to increase detector sensitivity.

To increase detection sensitivity to conductance variations in the nucleic acid hybridization assay according to the present invention, one end of the cleavable capture probe is bound to the substrate, and the other end of the cleavable capture probe is labeled with, for example, a conducting polymer (e.g., polyaniline), a fluorescent label, or a metal microsphere, to form a label-attached signal element ("label-attached cleavable capture probe"), thereby increasing a conductance (capacitance and impedance) variation relative to the cleaved signal element.

Another object of the present invention is to provide a nucleic acid hybridization assay method and device using a cleavage enzyme specifically responsive to a complementary double strand of nucleic acids, which are applicable to quantitative and qualitative assay devices.

In the present invention, cleavage is achieved by a cleavage enzyme, such as a DNAse, specific to double stands. In this case, only a capture probe acts as a cleavable signal element without a restriction probe. After the capture probe forms a double stand, the DNAse cleaves the double strand at a capture probe portion. Therefore, the capture probe functions as a "cleavable signal element"

Once a double strand that is cleavable by the DNAse is formed through hybridization of the capture probe to a target nucleic acid, the double strand is cleaved by the DNAse and separated from the substrate through washing.

In contrast, when the capture probe contacts a sample not including a complementary sequence to the capture probe, the capture probe does not form the double strand and thus remains as an uncleaved capture probe, attached to the substrate even after the addition of the DNAse and washing. After washing, a "label-attached uncleaved probe" structure may be optionally formed on the substrate by contacting the uncleaved signal element with a label, such as a fluorescent label or a metal microsphere, to increase detector sensitivity.

After contacting the sample, reaction with the DNAse, and washing, detection of the presence of the uncleaved probe or "label-attached uncleaved probe" on the substrate by the detector including an optical device, an electrochemical device, a mass measurement device, or a capacitance and impedance measurement device, indicates whether the analyte is present or not in the sample. Therefore, the "uncleaved probe" or "label-attached uncleaved probe" acts as an analyte presence/absence signal element. The presence of the cleavable signal element (uncleaved signal element) on the substrate indicates that sample does not contain a particular analyte, and the absence of the cleavable signal element (the cleaved signal element remain) indicates that sample contains a particular analyte.

Still another object of the present invention to provide a nucleic acid hybridization assay method and device using a cleavage enzyme specifically responsive to a single strand of nucleic acids, which are applicable to quantitative and qualitative assay devices.

In the present invention, cleavage is achieved by a cleavage enzyme, such as a nuclease, for example, derived from mung bean, specific to single strands. In this case, only a capture probe acts as a cleavable signal element without a restriction probe.

When the capture probe contacts a sample not including a complementary sequence to the capture probe, the capture probe does not form a double strand and remains as a single strand which is cleavable by the nuclease. The single strand is cleaved by the nuclease and separated from the substrate through washing.

In contrast, when the capture probe is double-stranded through hybridization to a target nucleic acid, the capture probe remains as an uncleaved probe, attached to the substrate even after the addition of the nuclease and washing.

After washing, a "label-attached uncleaved probe" structure may be optionally formed on the substrate by contacting the uncleaved signal element with a label, such as a fluorescent label or a metal microsphere, to increase detector sensitivity.

After contacting the sample, reaction with the nuclease, and washing, detection of the presence of the uncleaved probe or "label-attached uncleaved probe" on the substrate by the detector including an optical device, an electrochemical device, a mass measurement device, or a capacitance and impedance measurement device, indicates whether the analyte is present or not in the sample. Therefore, the "uncleaved probe" or "label-attached uncleaved probe" acts as an analyte presence/absence signal element. The presence of the cleavable signal element (uncleaved signal element) on the substrate indicates that sample contains a particular analyte, and the absence of the cleavable signal element (the cleaved signal element remain) indicates that sample does not contain a particular analyte.

Hereinafter, the structure of the present invention provided to achieve the above objects will be described.

To achieve an object of the present invention, there is provided a cleavable signal element comprising: a restriction probe of a single strand having a particular sequence cleavable by a restriction enzyme specific to a double strand of a particular sequence; and a capture probe of a single strand having a complementary sequence to a target nucleic acid for diagnosis or assay to form a double strand through hybridization to the target nucleic acid, wherein one end of the restriction probe is attached to a solid support substrate, and the other end of the restriction probe is ligated to the capture probe, thus forming a single-stranded, cleavable capture probe.

In the present invention, when the capture probe contacts a sample including the target nucleic acid of the complementary sequence, the capture probe is double-stranded through hybridization to the target nucleic acid, the restriction probe is double-stranded through DNA extension using the target nucleic acid hybridized to the capture probe as a primer with the addition of a DNA polymerization solution, the double-stranded restriction probe is cleaved by the restriction enzyme, and the cleaved cleavable capture probe is removed from the solid support substrate through washing, thus resulting in a cleaved signal element. In contrast, when the capture probe contacts a sample not including the target nucleic acid of the complementary sequence, the single-stranded, cleavable capture probe remains attached to the solid support substrate even after additions of the DNA polymerization solution and the restriction enzyme and washing, thus resulting in an uncleaved signal element. Preferably, the DNA polymerization solution comprises a solution of four dNTPs and a DNA polymerase solution.

Another cleavable signal element according to the present invention comprises a capture probe of a single strand having a complementary sequence to a target nucleic acid for diagnosis or assay to form a double strand through hybridization to the target nucleic acid, wherein one end of the capture probe is attached to a solid support substrate, and the capture probe itself forms a single-stranded, cleavable capture probe which is cleavable by a cleavage enzyme specifically responsive to a double strand or single strand of nucleic acids.

In this case, when the capture probe contacts a sample including the target nucleic acid of the complementary sequence, the capture probe is double-stranded through hybridization to the target nucleic acid, the double-stranded capture probe is cleaved by the cleavage enzyme specifically responsive to the double strand of nucleic acids, and the cleaved cleavable capture probe is removed from the solid support substrate through washing, thus resulting in a cleaved signal element. In contrast, when the capture probe contacts a sample not including the target nucleic acid of the complementary sequence, the single-stranded, cleavable capture probe remains attached to the solid support substrate even after the addition of the cleavage enzyme and washing, thus resulting in an uncleaved signal element. Preferably, the cleavage enzyme is a DNAse.

When the capture probe contacts a sample not containing the target nucleic acid of the complementary sequence, the capture probe remains as a single strand without hybridization, the single-stranded capture probe is cleaved by the cleavage enzyme specifically responsive to the single strand of nucleic acids, and the cleaved cleavable capture probe is removed from the solid support substrate through washing, thus resulting in a cleaved signal element. In contrast, when the capture probe contacts a sample including the target nucleic acid of the complementary sequence, the capture probe is double-stranded through hybridization to the target nucleic acid, and the double-stranded, cleavable capture probe remains attached to the solid support substrate even after the addition of the cleavage enzyme and washing, thus resulting in an uncleaved signal element. Preferably, the cleavage enzyme is a nuclease, more preferably, derived from mung bean.

In the cleavable signal elements according to the present invention, the solid support substrate may be a plastic substrate, a glass substrate, a silicon substrate, or a gold substrate. Preferably, the solid support substrate has a self-assembled monolayer (SAM) on the surface. Preferably, the capture probe has a length ranging from about 5- to about 30-mers.

To increase detection sensitivity for an uncleaved signal element, it is preferable that a label is attached to one end of the cleavable capture probe to form a label-attached cleavable capture probe structure or to one end or side of an uncleaved probe to form a label-attached uncleaved probe structure, to increase detection sensitivity for an uncleaved signal element. In this case, the label may comprise a metal microsphere, a conducting polymer, a fluorescent dye, a magnetic microsphere, and a streptavidin-labeled microsphere. Preferably, the metal microsphere is formed of a metal selected from the group consisting of gold, silver, nickel, platinum, chromium, and copper. Preferably, a gold microsphere has a diameter ranging from about 1 nm to about 10 µm. Preferably, the streptavidin-labeled microsphere is attached to the cleavable capture probe via biotin.

To achieve another object of the present invention, there is provided a nucleic acid hybridization assay device comprising: a solid support substrate; a plurality of cleavable signal elements according to any of the cleavable signal elements described above attached to the solid support substrate; and an internal or external detector which detects a uncleaved signal element and a cleaved signal element from the plurality of cleavable signal elements.

It is preferable that the detector comprises an optical device, an electrochemical device, a mass measurement device, or a capacitance and impedance measurement device. Preferably, the optical device detects fluorescence of the uncleaved signal element and cleaved signal element.

It is preferable that the detector detects a differential reflective signal or a differential conductive signal of the uncleaved signal element and the cleaved signal element. Preferably, the detector detects the differential reflective signal by measuring the reflectance, absorbance, or scattering of light or a laser beam incident on the uncleaved signal element and the cleaved signal element.

Alternatively, the detector may detect the differential conductive signal by measuring the capacitance and impedance of the uncleaved signal element and the cleaved signal element. In this case, preferably, the capacitance and impedance measurement device measures the frequency response characteristics of the uncleaved signal element and the cleaved signal element.

In the nucleic acid hybridization assay device according to the present invention, the capacitance and impedance measurement device may comprise interdigitated array electrodes having at least one digit and arranged on the solid support substrate. Preferably, the interdigitated array electrodes are substantially formed of gold. Preferably, the interdigitated array electrodes have an input port to check for the frequency response characteristics, and the input port is connected to an electronic control device which generates a frequency signal of a constant bandwidth.

In the nucleic acid hybridization assay device according to the present invention, a plurality of cleavable signal elements may be deposited on the interdigitated array electrodes, preferably only in the space between the interdigitated array electrodes.

In the nucleic acid hybridization device according to the present invention, to increase the sensitivity of the detector, it is preferable that a label-attached uncleaved probe structure is formed on the solid support substrate by attaching a label to the uncleaved signal element.

Preferably, the plurality of cleavable signal elements are deposited on the solid support substrate in a spatially-addressable pattern, more preferably, to enable a single-sample assay for multiple analytes, a multiple-sample assay for a single analyte, or a multiple sample assay for multiple analytes.

In the nucleic acid hybridization device according to the present invention, it is preferable that the solid support substrate is a plastic substrate formed of a material selected from the group consisting of polypropylenes, polyacrylates, polyvinyl alcohols, polyethylenes, polymethylmethacrylates, and polycarbonates. Among those materials for the solid support substrate, polycarbonates are more preferred. Preferably, the solid support substrate is formed of a circular disk or a rectangular disk. The circular disk may have a diameter of approximately 120 mm and a thickness of approximately 1.2 mm. The nucleic acid hybridization assay device according to the present invention may include a plurality of circular disks.

It is preferable that, in the nucleic acid hybridization device according to the present invention, the circular disk comprises: a central void to engage a rotational drive means; a sample injection port through which a sample is injected; and an annular and/or a spiral track in which the plurality of cleavable signal elements are deposited in the spatially-addressable pattern. Preferably, an address pattern that provides coded address information is formed on the circular disk.

Alternatively, the circular disk in the nucleic acid hybridization device according to the present invention may comprise: a central void to engage a rotational drive means; a sample injection port through which a sample is injected; and a radial assay sector in which the plurality of cleavable signal elements are deposited in the spatially-addressable pattern. Preferably, the circular disk comprises a plurality of assay sectors. The plurality of assay sectors may be connected to respective separate sample injection ports or to a common sample injection port. The plurality of cleavable signal elements are deposited in each of the plurality of assay sectors in an appropriate pattern for a single-analyte assay or a multiple-analyte assay. Therefore, the nucleic acid hybridization assay device according to the present invention is applicable for a single-sample assay for multiple analytes, a multi-sample assay for a single analyte, and a multi-sample assay for multiple analytes.

It is preferable that the circular disk includes in a central track a database associated with bioinformatics required for diagnosis and assay interpretation, and telephone numbers, web link information and software required for remote diagnosis.

In the nucleic acid hybridization device according to the present invention, it is preferable that a detector is mounted on the circular disk. The detector may comprise a non-contact interface through which information read from the cleaved signal element and the uncleaved signal element is transmitted to an external central controller or storage device. Preferably, the non-contact interface comprises an infrared interface and an optical interface. As an example, the infrared interface may an infrared sensor, and the optical interface may be a photosensor.

Preferably, the circular disk in the nucleic acid hybridization assay device according to the present invention simultaneously comprises at least one SNP (single nucleotide polymorphism) assay sector for SNP detection and at least one expression assay sector for expression profile analysis. In this case, the SNP assay sector and the expression assay sector may be arranged separate in an angular direction or in a radial direction.

To achieve still another object of the present invention, there is provided bio-driver apparatus comprising: a rotary disk receiver onto which any nucleic acid assay device described above is to be loaded; a motor driver which rotates the disk; a rotary connector which connects the motor driver to a central void portion of the disk such that the disk is rotatable; and an optical device to write data in or to read data from the disk.

Preferably, the bio-driver apparatus further comprises a central controller which transmits information read from the disk by the optical device to an external storage unit, transmits information to be written to the optical device, and generates and outputs a variety of control signals for the motor driver and the other elements.

In the bio-driver apparatus according to the present invention, it is preferable that the rotary connector comprises an upper rotor and/or a lower rotor, the upper and lower rotors being pushed close to the top and bottom surfaces, respectively, of the central void portion when the disk begins to rotate.

In the bio-driver apparatus according to the present invention, the optical device may detect fluorescence, preferably, a differential reflective signal by measuring the reflectance, absorbance, or scattering of incident light or an incident laser beam.

Alternatively, the present invention provides a bio-driver apparatus comprising: a rotary disk receiver onto which any nucleic acid assay device described above is to be loaded; a motor driver which rotates the disk; a rotary connector which rotatably connects the motor driver to a central void portion of the disk; an external power connector which powers and/or supplies a control signal to a detector mounted on the disk; and a non-contact interface through which information read by the detector is transmitted.

Preferably, the bio-driver apparatus further comprises a central controller which transmits information read from the disk by the detector to an external storage unit and generates and outputs a variety of control signals for the motor driver and the other elements.

Preferably, the bio-driver apparatus further comprises an optical device to write data in or to read data from the disk. Software including, for example, bioinformatics information, can be written in or read from the disk.

Preferably, the detector detects a differential conductive signal by measuring capacitance and impedance.

Preferably, the rotary connector comprises an upper rotor and/or a lower rotor, the upper and lower rotors being pushed close to the top and bottom surfaces, respectively, of the central void portion when the disk begins to rotate.

Preferably, the power connector comprises a brush that frictionally contacts the upper and/or lower rotors in connection with an external power supply unit, and each of the upper and lower rotors comprises an annular electrode plate frictionally contacting the brush. One of the upper and lower rotors may be used. In this case, two opposite nodes of the power supply unit are connected to one brush. When both of the upper and lower rotors are used, brushes contacting the upper and lower rotors may respectively connected to the opposite nodes of the power supply unit.

It is preferable that the annular electrode plate comprises at least one conductive arm connected thereto, and the central void portion of the disk comprises a hole to engage the at least one conductive arm and a circuit pattern connected to the hole to power the detector mounted on the disk and/or supply the control signal to the detector. In this case, the at least one conductive arm may a spring at its one end that is connected to the annular electrode plate.

In the bio-driver apparatus according to the present invention, it is preferable that the power connector comprises an electromagnet attached to the rotary disk receiver in connection with the external power supply unit, and the electromagnet induces an AC voltage to a wound coil on the disk so that the detector is powered in a non-contact manner. In this case, the disk further preferably comprises a rectifier for rectifying the AC voltage induced to the wound coil.

To achieve yet still another object of the present invention, there is provided a remote diagnostic system comprising: any nucleic acid hybridization assay device according to the present invention described above, an existing communication network such as the Internet; and a computer in which software capable of controlling access to the existing communication network and digitizing information read from the nucleic acid hybridization assay device is installed, wherein the digitized information from the nucleic acid assay hybridization assay device is transmitted to a doctor or a hospital, and a patient is provided with a prescription, through the existing communication network.

In the remote diagnostic system according to the present invention, the computer may comprise assay interpretive algorithms, bioinformatics information, and self-diagnostics related software. Preferably, the computer comprises software capable of uploading diagnostic information to remote locations and device drivers. In this case, the software may include educational information for patients on clinical assays, a variety of wet sites and links enabling a patient to directly communicate with a doctor or hospital based on his/her diagnosis result.

It is preferable that the computer comprises a camera and a microphone for viewing a patient's face and listening to his/her voice. It is preferable that the diagnostic data based on the digitized information are displayed on a computer monitor, the computer automatically or manually transmits the diagnostic data to a specialist through the existing communication network, and the patient waits for a prescription from the specialist.

To achieve another object of the present invention, there is provided a nucleic acid hybridization assay method comprising: hybridizing a capture probe to a target nucleic acid present in a liquid sample by contacting any nucleic acid hybridization assay device according to the present invention described above, with the liquid sample; contacting the cleavable capture probe with a restriction enzyme or cleavage enzyme which is specifically responsive to a cleavable signal element depending on whether the capture probe and the target nucleic acid are hybridized or not; washing the nucleic acid hybridization assay device to remove the cleavable signal element cleaved by the restriction enzyme or cleavage enzyme; and detecting whether the uncleaved signal element or the cleaved signal element exists on the solid support substrate.

Preferably, the nucleic acid hybridization assay method further comprises contacting the cleavage capture probe with a DNA polymerization solution before contact with the restriction enzyme. As a result, the restriction probe forms a double strand through DNA extension using the target nucleic acid hybridized to the capture probe as a primer. Preferably, the nucleic acid hybridization assay method further comprises contacting the cleavage capture probe with a 3'-5' exonuclease solution before contact with the DNA polymerization solution. As a result, a portion of the target nucleic acid that remains as a single strand without hybridization to the capture probe is cleaved, so that the target nucleic acid can act as the primer.

It is preferable that the nucleic acid hybridization assay method further comprises attaching a label to the cleavable signal element before contacting the capture probe with the liquid sample, or to an uncleaved signal element after contacting the cleavable capture probe with the restriction enzyme or cleavage enzyme. When the label attachment is applied before contacting the sample, it is preferable that the label is attached during the synthesis of the capture probe or after the immobilization of the capture probe to a solid support substrate. Preferably, simple washing is performed between contact with the restriction enzyme and the label attachment.

It is preferable that the nucleic acid hybridization assay method further comprises at least one wash step. In the nucleic acid hybridization assay method, washing may be performing by rotating the nucleic acid hybridization assay device with or without addition of a detergent solution, or by applying an external electric field.

One embodiment of the nucleic acid hybridization assay method according to the present invention comprising: (a) injecting a sample into a sample injection port disposed near the center of a disk in a nucleic acid hybridization assay device; (b) rotating the disk and stopping the rotation of the disk when the sample reaches an outer edge of the disk; (c) incubating the disk in a stationary state at room temperature for hybridization; (d) adding a buffer solution as a washing solution while rotating the disk at a high speed, to wash the disk; (e) adding a DNA polymerization solution containing a mixed solution of four dNTPs and a DNA polymerase and incubating the disk in a stationary state for DNA extension; (f) adding a solution of a restriction enzyme specifically responsive to a double strand of a particular sequence and incubating the disk in a stationary state, to cleave the double strand; (g) washing the disk by rotating the disk at a high speed with the addition of a buffer solution or by applying an external electric or magnetic field; and (h) drying the disk and reading information from the disk using a detector which is programmed to detect a predetermined assay site on which a cleavable signal element is deposited and comprises an optical device, an electrochemical device, or a capacitance and impedance measurement device.

It is preferable that the nucleic acid hybridization assay method further comprises adding a 3'-5' exonuclease solution before step (e) of DNA extension. As a result, a portion of the target nucleic acid that remains as a single strand without hybridization to the capture probe is cleaved, so that the target nucleic acid can act as the primer.

Another embodiment of the nucleic acid hybridization assay according to the present invention comprises: (a) injecting a sample into a sample injection port disposed near the center of a disk in a nucleic acid hybridization assay device; (b) rotating the disk and stopping the rotation of the disk when the sample reaches an outer edge of the disk; (c) incubating the disk in a stationary state at room temperature for hybridization; (d) adding a buffer solution as a washing solution while rotating the disk at a high speed, to wash the disk; (e) adding a solution of a cleavage enzyme specifically responsive to a double strand or single strand of nucleic acids and incubating the disk in a stationary state, to cleave the double strand or single strand; (f) washing the disk by rotating the disk at a high speed with the addition of a buffer solution or by applying an external electric or magnetic field; and (g) drying the disk and reading information from the disk using a detector which is programmed to detect a predetermined assay site on which a cleavable signal element is deposited and comprises an optical device, an electrochemical device, or a capacitance and impedance measurement device.

To increase detection sensitivity, the nucleic acid hybridization assay methods described above may further comprise attaching a label to the cleavable signal element before sample injection, or to an uncleaved signal element after strand cleavage. When the label attachment is applied before contacting the sample, it is preferable that the label is attached during the synthesis of the capture probe or after the immobilization of the capture probe to a solid support substrate. Preferably, simple washing is performed between contact with the restriction enzyme and the label attachment.

BRIEF DESCRIPTION OF THE DRAWINGS

FIGS. 1A through 2C show alternative embodiments of the attachment of a plurality of cleavable signal elements to a derivatized site of a variety of substrates, in particular:

FIG. 1A is a schematic representation of the attachment of a plurality of cleavable capture probes (cleavable signal elements) at a derivatized site on the plastic (carbonate) substrate of an assay device by covalent bonds, where n of $(CH)_n$ is an integer greater than zero;

FIG. 1G is a schematic representation of the formation of a "label-attached uncleaved probe" structure by contacting the second capture probe with a label, for example, an SSB protein, in which the second capture probe is tethered to the substrate surface while the first capture probe is removed from the substrate surface through washing, which provides differential signals as well as spatially-addressable differential reflective signals to a detector including an optical device, an electrochemical device, a mass measurement device, or a capacitance and impedance measurement device;

FIG. 2A is a schematic representation of an embodiment of the nucleic acid hybridization assay according to the present invention to increase the sensitivity of a detector including an optical device, an electrochemical device, a mass measurement device, or a capacitance and impedance measurement device, in which a plurality of cleavable capture probes (cleavable signal elements) are covalently bound to a derivarized site of the plastic substrate (polycarbonate) surface of an assay device, and metal microspheres, conducting polymers, or fluorescent labels are attached to the other free end of the cleavable capture probes;

FIG. 2B is a schematic representation of the cleavage and removal of the first capture probe by washing; and FIG. 2C is a schematic representation of the labeling of the other free end of the cleavable capture probes with a streptavidin-labeled magnetic microbead;

FIGS. 10A through 10K illustrate embodiments of attachment of cleavable signal elements to different types of substrate surfaces for an assay device;

DETAILED DESCRIPTION OF THE INVENTION

The present invention, including a nucleic acid hybridization assay method and device, using a cleavage technique specifically responsive to a complementary double strand or single strand of nucleic acids or oligonucleotide will be described in greater detail with reference to the appended drawings.

<Spatially Addressable Cleavable Signal Elements>

Figure 1A:
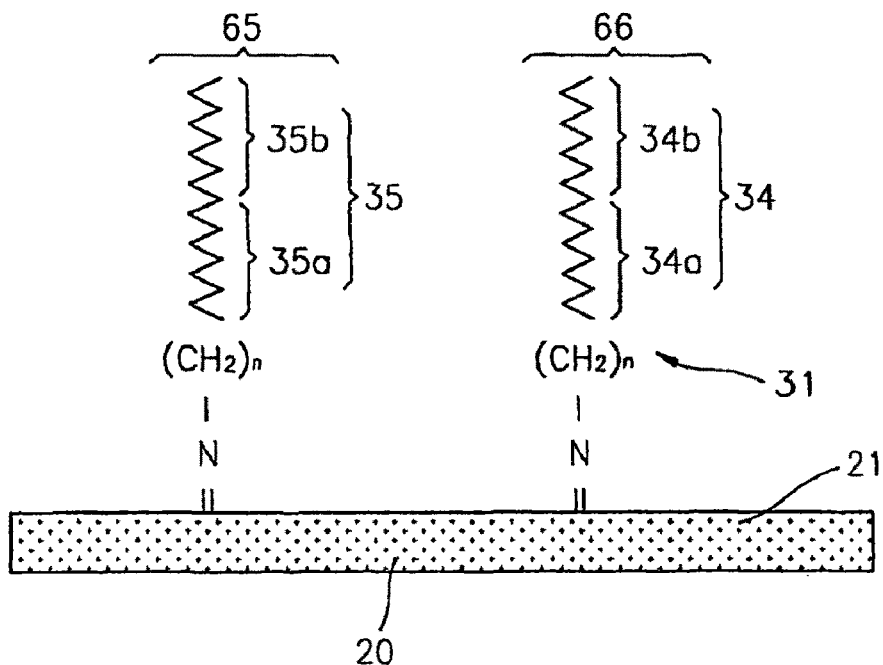
Figure 1B:
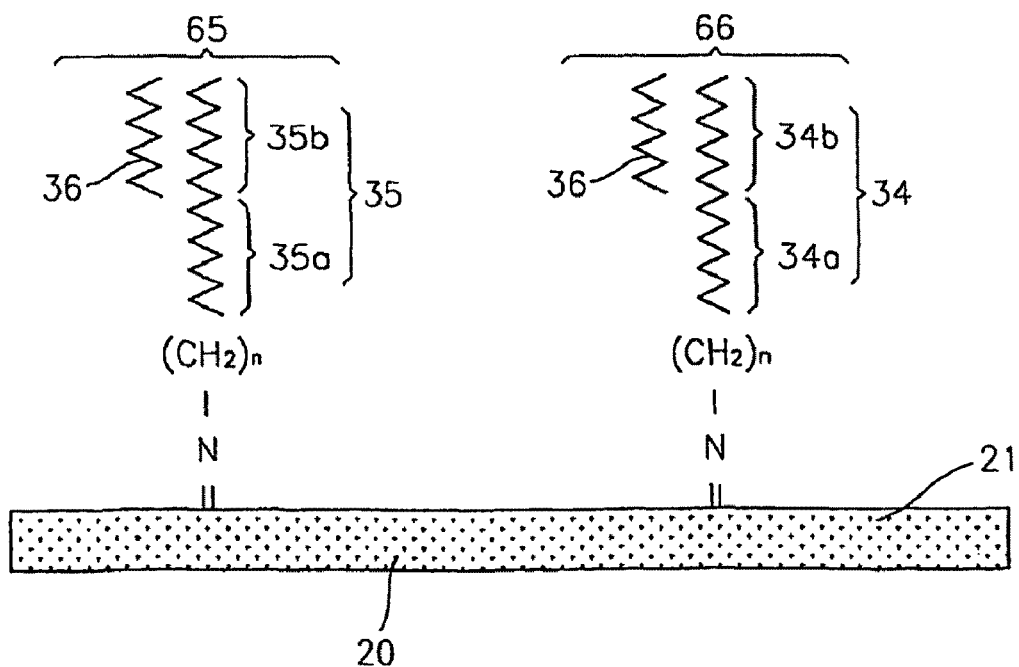
FIG. 1B is a schematic representation of a nucleic acid hybridization assay shortly after introduction of a sample containing nucleic acids.
Figure 1C:
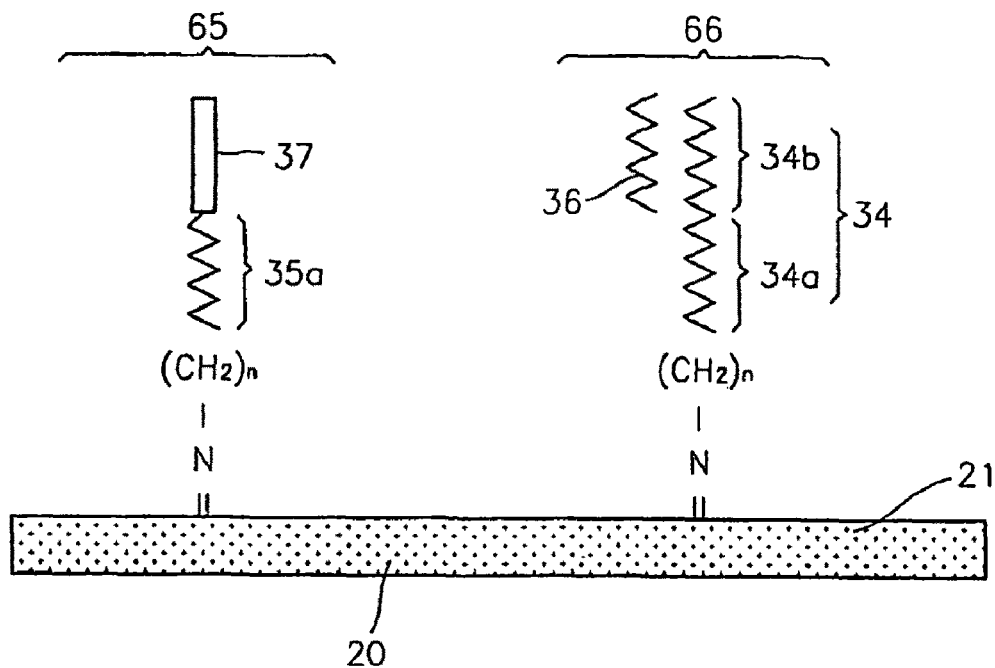
FIG. 1C is a schematic representation of a step after the procedure of FIG. 1B, in which oligonucleotides present in the sample have bound to complementary oligonucleotide of a first capture probe to form a double strand, but have not bound to oligonucleotide of a second capture probe, where the rectangular box denotes the complementary double strand formation.

The reaction mechanism of a cleavable signal element according to the present invention, termed a "bio-bit", can be easily understood by reference to FIGS. 1A through 1C. Referring to FIG. 1A, a plastic substrate 20 has a substrate 21 to which are attached cleavable capture probes 34 and 35. The substrate 20 can be formed of a porous or solid substrate using a variety of materials including plastic, glass, mica, silica, and the like, but plastic is most preferred for reasons of economy, ease of derivatization for attaching the cleavable signal elements to the surface, and compatibility with existing laser reflection-based detectors, such as CD-ROM and DVD readers. Suitable plastics include polypropylenes, polyacrylates, polyvinyl alcohols, polyethylenes, polymethylmethacrylates, and polycarbonates, with polypropylenes and polycarbonates being preferred and polycarbonates being the most preferred.

The cleavable signal elements 34 and 35 include respective capture probes 34b and 35b and respective restriction probes 34a and 35a. The surface 21 of the substrate 21 can be derivatized to provide covalent bonding to each of the cleavable signal elements 34 and 35. To protect the cleavable capture probes 34 and 35 from direct contact with the surface 21 of the substrate 21, a monomer layer of non-reactive molecules, for example, an alkane chain $(CH.sub.2)_n$, can be formed on any substrate according to the present invention. As an example, an alkane chain $((CH.sub.2)_n)$ 31 attached to one end of the restriction probe 34a is shown.

The alkane chain 21 at one end of each restriction probes 34a and 35a is attached to the surface 21 via an amide linkage. The restriction probes 34a and 35a of the cleavable signal elements 34 and 35 have a cleavage site that is susceptible to cleavage by a restriction enzyme in double-strand formation.

Analyte specificity is conferred upon the cleavable signal element by the sequence of the capture probes 34b and 35b. The capture probes 34b and 35b includes an oligonucleotide of 5- to 20-mers, preferably 8- to 17-mers, most preferably 8- to 12-mers, but longer oligonucleotides (cDNA) can be used. A large number of cleavable signal elements 34 and 35 are present at particular derivatized sites on the surface 21 of the substrate 20 of an assay device called a "bio-disk".

In the present invention, the oligonucleotides of the capture probes 34b and 35b bind with the complementary single strands of nucleic acids present in a test sample. In other words, the complementary oligonucleotides form double strands, each including a specific binding pair.

As shown in FIGS. 1A through 2C, the cleavable signal elements (cleavable capture probes) 34 and 35 at different sites on the assay device surface have discrete oligonucleotide sequences. In FIG. 1A, the first and second cleavable signal elements 65 and 66 have oligonucleotides 35b and 34b, respectively.

As shown in FIGS. 1B and 1C, when contacted with a test sample containing an oligonucleotide 36, the complementary oligonucleotide 35b binds with the oligonucleotide 36 present in the test sample to form a double strand (referred to as also a "capture double strand") 37, as shown in FIG. 1C. If there no complementarity between the sample oligonucleotide 36 and the oligonucleotide 34b, there is no binding between those groups as illustrated in FIG. 1C. The capture probe 35b forms the double strand 37 with the sample oligonucleotide 36, whereas the restriction probe 35a at one end of the capture probe 35b currently remains as a single strand.

Figure 1D:
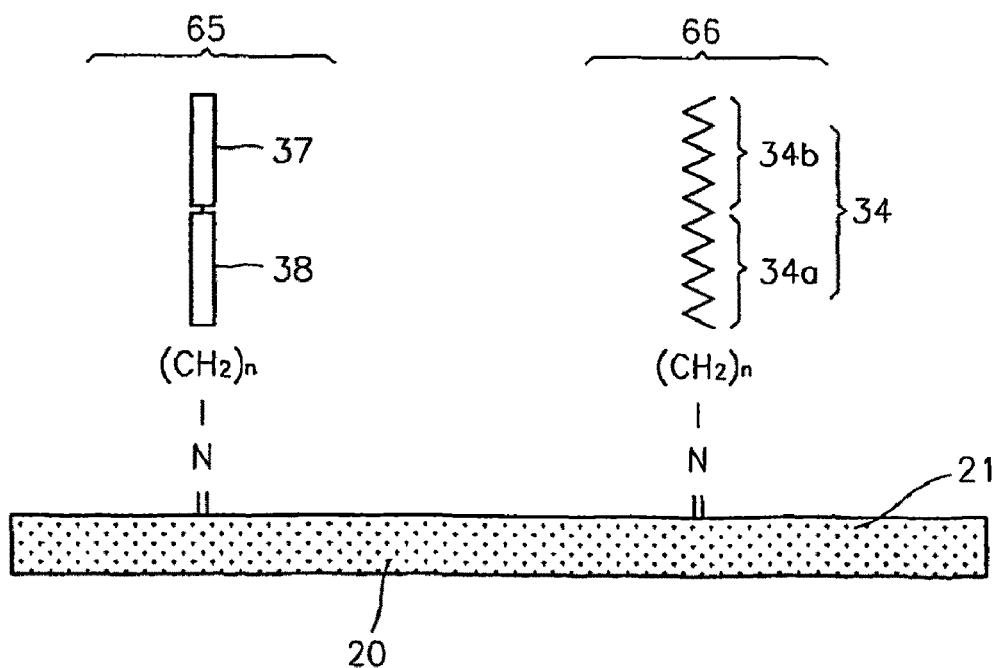
FIG. 1D is a schematic representation of a step after the procedure of FIG. 1C, in which a single-stranded restriction probe ligated to the end of the first capture probe is double-stranded using a DNA polymerization solution, in particular, the restriction probe forms a double strand through DNA extension using the complementary target nucleic acid attached to the first capture probe in the step of FIG. 1C as a primer, whereas the second capture probe still remains as a single strand.

To form a double strand of the restriction probe 35a at one end of the capture probe 35b that have formed the double strand 37, as shown in FIG. 1D, a DNA polymerization solution is added. The restriction probe 35a is double-stranded via DNA extension using a target nucleic acid hybridized to the capture probe 35b as a primer. The restriction double strand 38 formed through the DNA extension is shown in FIG. 1B.

Figure 1E:
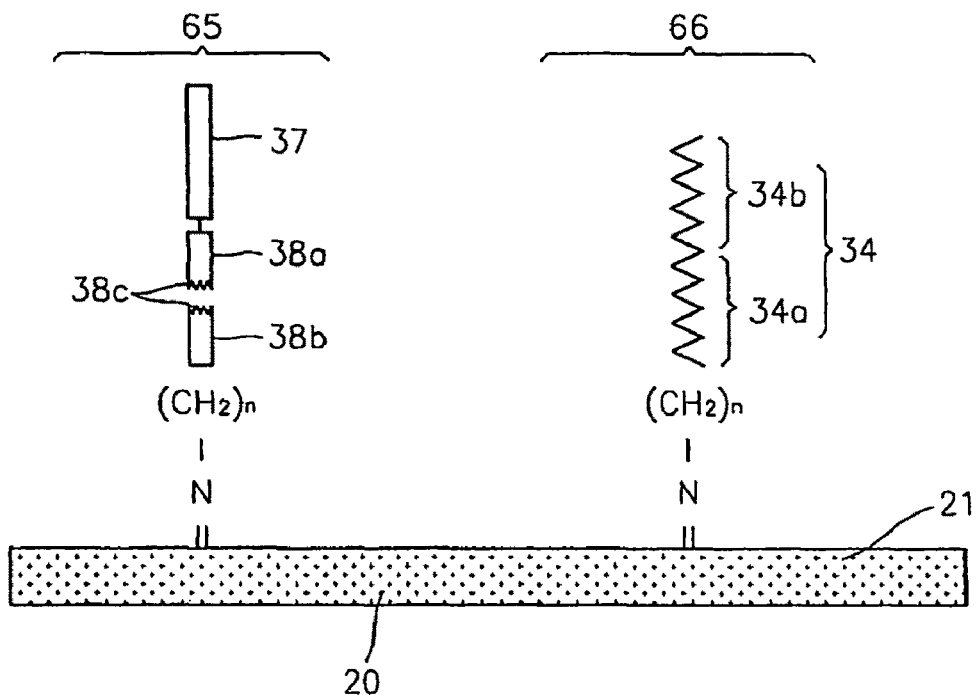
FIG. 1E is a schematic representation of a step after the assay procedure of FIGS. 1C and 1D, in which the restriction probe ligated to the end of the first capture probe that has formed the double strand is cleaved by contact with a restriction enzyme, and the cleavable first capture probe double-stranded through the complementary hybridization is removed from the substrate surface, whereas the second capture probe still remains as a single strand on the substrate surface.

In FIG. 1E, cleavage of the restriction double strand 38 by addition of a restriction enzyme after formation of the capture and restriction double strands 37 and 38 in the steps of FIGS. 1C and 1D is shown.

Figure 1F:
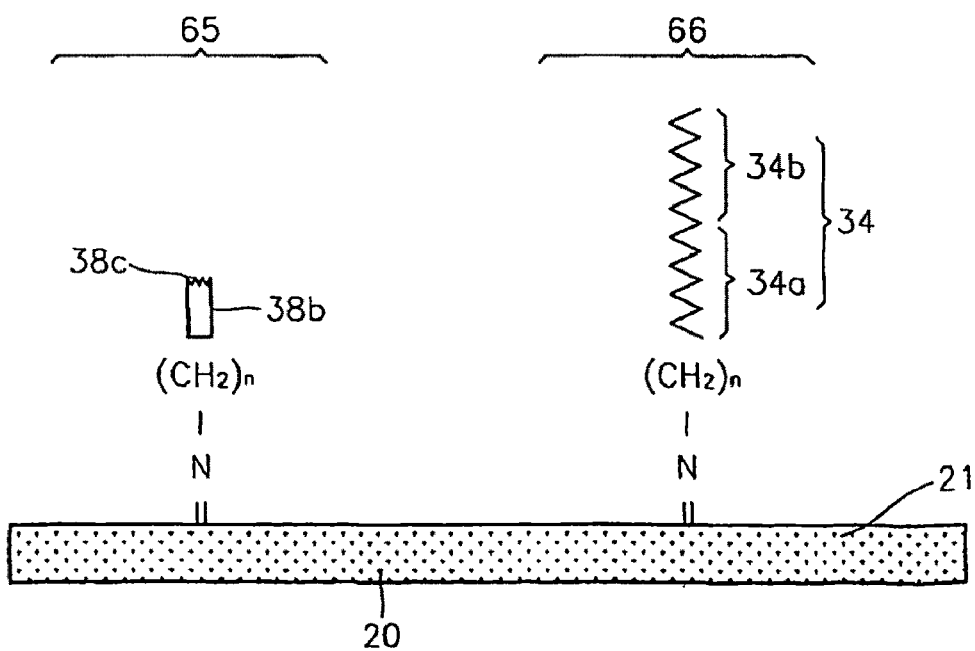
FIG. 1F is a schematic representation of the removal of the first capture probe cleaved in the procedure of FIG. 1E by washing.

After the restriction double strand 38 is cleaved at the cleavage site 38c, the first cleavable signal element 65 specifically bound with the test sample is detached and removed from the surface 21 by washing. This is illustrated in FIG. 1F. If it is desired to assay multiple samples for a single oligonucleotide, the captures probes at different sites will generally have the same oligonucleotide sequence. Presence or absence of a cleavable signal element (after cleavage) on the surface 21 may be detected from differential reflectance of incident light, in particular, incident laser light, or by a capacitance and impedance measurement device capable of measuring conductivity variations.

FIG. 1G illustrates an alternative embodiment of labeling after the washing to increase the sensitivity of a detector. The uncleaved signal element 66 remaining on the substrate 20 after the step of FIG. 1F is brought into contact with a label 39, for example, an SSB protein, to form a "label-attached uncleaved probe" structure and thus increase a difference in reflectivity or conductivity between the cleaved signal element 65 and the uncleaved signal element 66, thereby resulting a higher sensitivity of the detector.

FIG. 2A is a schematic representation of an embodiment of the nucleic acid hybridization assay according to the present invention to increase the sensitivity of a detector including an optical device, an electrochemical device, a mass measurement device, or a capacitance and impedance measurement device. As shown in FIG. 2A, a plurality of cleavable capture probes (cleavable signal elements) are covalently bound to a derivarized site of the plastic substrate (polycarbonate) surface of an assay device, and a label 40, such as a metal microsphere, conductive polymer, or fluorescent label is attached to the other free end of the cleavable capture probes.

The label 40, such as the metal microsphere, act as a reflective signal generation element to permit detection of the presence of the first and second cleavable signal elements 65 and 66 coupled to the substrate 20 of the assay device. Suitable materials for the reflective signal generation element include gold (Au), silver (Ag), nickel (Ni), chromium (Cr), platinum (Pt), and copper (Cu), but Au is preferred due to its nature to easily and strongly bind to a thiol (SH)-group attached to one end of the cleavable signal elements 34 and 35. The metal microsphere may be formed of solid metal, metal-coated plastic, or glass bead. Any reflective materials, instead of metal, can be used. Au-microspheres directly bind to a thiol group attached to one end of the cleavable signal elements 34 and 35.

In FIG. 2A, the first and second cleavable signal elements 65 and 66 have the oligonucleotides 35b and 34b, respectively. When contacted with a test sample containing an oligonucleotide, the complementary oligonucleotide 35b binds with the oligonucleotide present in the test sample to form a double strand (not shown). If there no complementarity between the sample oligonucleotide and the oligonucleotide 34b, there is no binding between those groups. The capture probe 35b forms the double strand with the sample oligonucleotide, whereas the restriction probe 35a at one end of the capture probe 35b currently remains as a single strand.

To form a double strand with the restriction probe 35a at one end of the capture probe 35b that have formed the double strand, a DNA polymerization solution is added. The restriction probe 35a is double-stranded via DNA extension using a target nucleic acid of the hybridized capture probe as a primer. After formation of the complete double strand, the double-stranded restriction probe is cleaved by addition of a restriction enzyme.

After the double-stranded restriction probe is cleaved at the cleavage site 38c, the first cleavable signal element 65 specifically bound with the test sample and the label 40 are detached and removed from the surface 21 by washing. This is illustrated in FIG. 2B. Presence or absence of a cleavable signal element (after cleavage) on the surface 21 may be detected from differential reflectance of incident light, in particular, incident laser light, and by a capacitance and impedance measurement device capable of measuring conductivity variations.

FIG. 2C shows an embodiment of the labeling of cleavable capture probes with the label 39, which may be a metal microsphere, conducting polymer, or fluorescent label, in FIG. 1G. In FIG. 2C, a plurality of cleavable signal elements are covalently bound to a derivatized site of the surface 21 of the assay device substrate 20, and the other end of the cleavable signal elements is labeled with the label 39, such as a metal microsphere, conducting polymer, or fluorescent label, via avidin 51 and biotin 50.

Figure 3A:
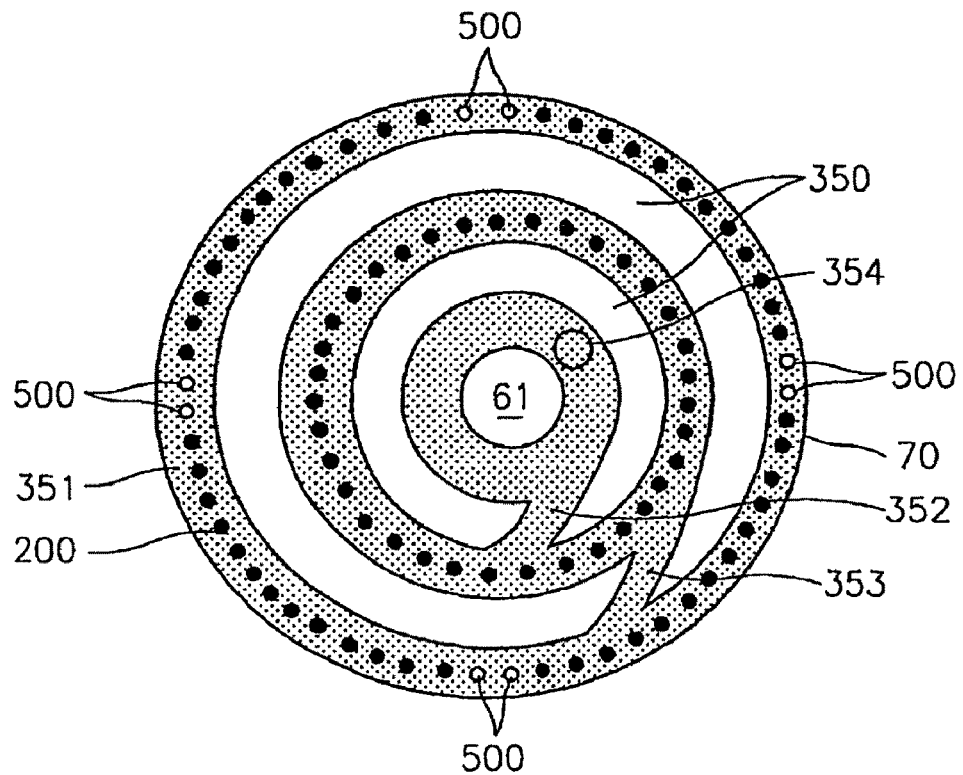
FIGS. 3A through 3D show alternative embodiments of the spatially addressable arrangement of the cleavable signal elements.

FIGS. 3A through 3D show alternative embodiments of the spatially addressable arrangement of the cleavable signal elements. In particular, FIG. 3A shows an address pattern 500 formed on a substrate 70 of a circular disk to provide coded address information, from which the location of a cleavable signal element 200 may be optically or fluorescently measured, and the attachment of the cleavable signal element 200 to annular tracks 351 by deposition. The circular disk has a central void 61 to engage a rotational drive means. Adjacent annular tracks are connected with each other by spiral-track bridges 352 and 353 to permit the sample injected through a sample injection port 354 to uniformly and outwardly spread by a centrifugal force generated as the disk rotates. The address information of the disk can be obtained from the address pattern 500, which is a regular pattern impressed at a fixed location. Reference numeral 350 denotes a track-to-track interval. FIG. 3A shows the deposition of the cleavable signal element in an appropriate pattern to assay in parallel a single sample for multiple analytes.

Figure 3B:
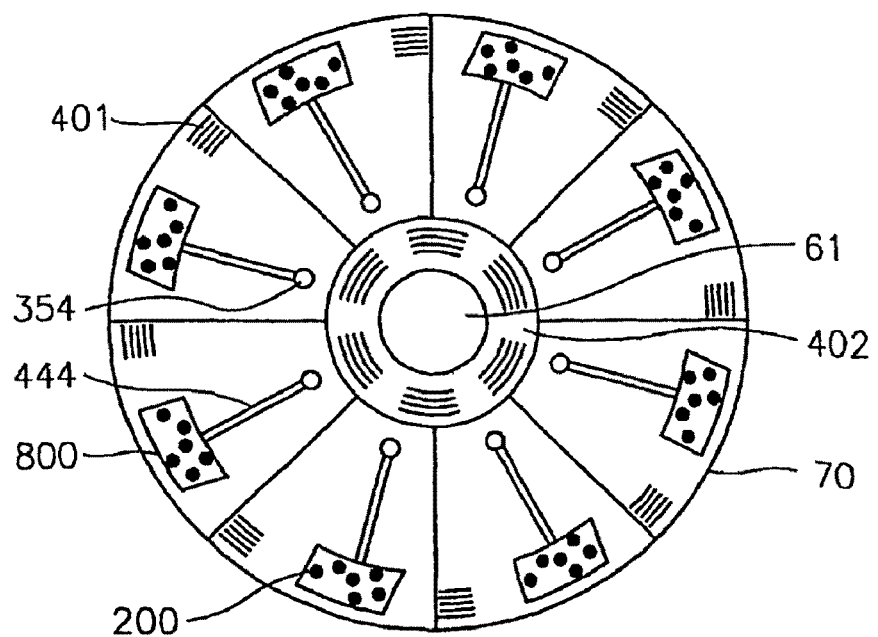

FIG. 3B shows an address pattern 401 formed on the substrate 70 of the circular disk to provide coded address information, from which the location of the cleavable signal element 200 may be optically or fluorescently measured, and the attachment of the cleavable signal element 200 to radial tracks 351 by deposition. The circular disk has a central void 61 to engage a rotational drive means. FIG. 3B shows the deposition of the cleavable signal element in an appropriate pattern to assay in parallel multiple samples. A database associated with bioinformatics required for diagnosis and assay interpretation, and telephone numbers, web link information, and software required for remote diagnosis may be coded and stored in a central track 402. The embodiment of FIG. 3B shows assay sectors with individual sample injection ports 354 and segregated from one another, thereby permitting rotation of the assay device without sample mixing. In FIG. 3B, reference numeral 444 denotes a sample flow channel along which a sample flows from the sample injection port 354 to a corresponding assay sector 800. If multiple sample injection ports 354 are interconnected with each other, a single sample can be assayed for multiple analytes.

Figure 3C:
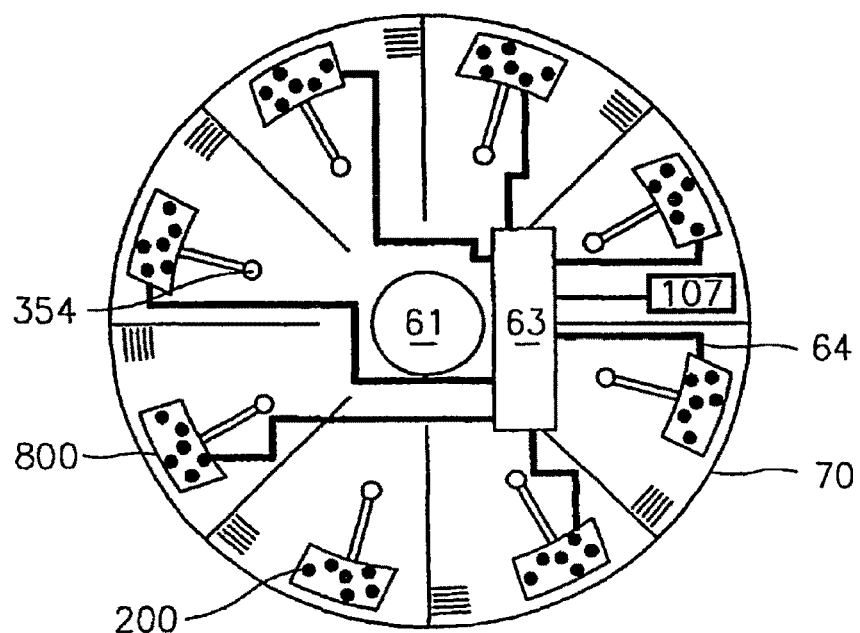

FIG. 3C shows the attachment of the cleavable signal element 200 to a radial track for each assay sector 800 by deposition. To electrically measure whether the cleavable signal element 200 is cleaved or not using the detector including a capacitance and impedance measurement device described above, an electronic control unit 63 and a circuit pattern 64 connecting each of the assay sectors 800 to the electronic control unit 63 are mounted on the substrate 70 of the circular disk. The electronic control unit 63 measures the capacitance and impedance with respect to each of the assay sectors 800 by checking for their frequency response characteristics, thereby providing information on whether the cleavable signal element 200 is cleaved or not, or information on the degree of cleavage. The frequency response characteristics measured by the electronic control unit 63 is transmitted to an external central controller (not shown) or storage device (not shown) via a non-contact interface 107, for example, an infrared interface or optical interface, designed on the disk. In FIG. 3C, reference numeral 354 denotes a sample injection port.

Figure 3D:
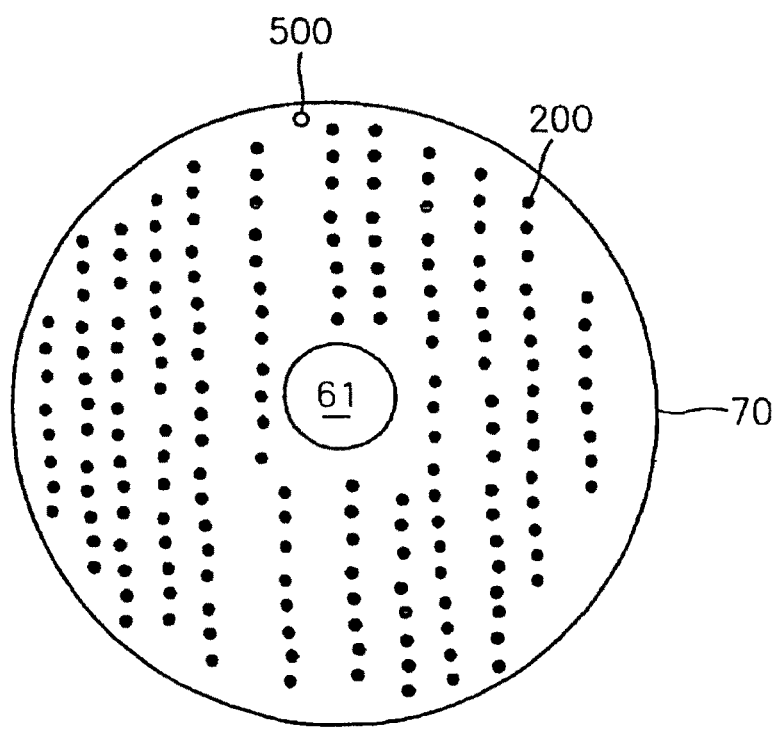

FIG. 3D shows an address pattern 401 formed on the substrate 70 of the circular disk to provide coded address information, from which the location of the cleavable signal element 200 may be optically or fluorescently measured, and the attachment of the cleavable signal element 200 at a constant interval over the entire surface of the disk by deposition. The circular disk has a central void 61 to engage a rotational drive means. The structure of FIG. 3D is suitable for a single-analyte assay with multiple samples or for a multiple-analyte assay with a single sample. To end this, samples may be injected through individual sample injection ports arranged in an ink-jet array corresponding to the location of each capture probes. Alternatively, a sample may be injected through a single sample injection port and spread over the entire substrate by a rotational force.

Figure 4A:
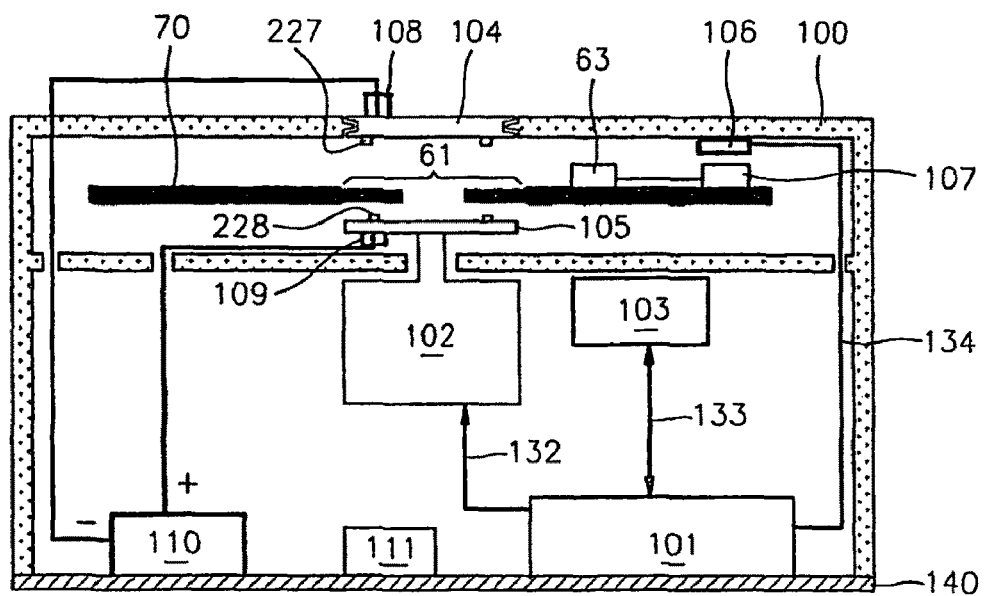
FIGS. 4A through 4E show alternative embodiments of the supply of power to a rotating assay device (disk)
Figure 4B:
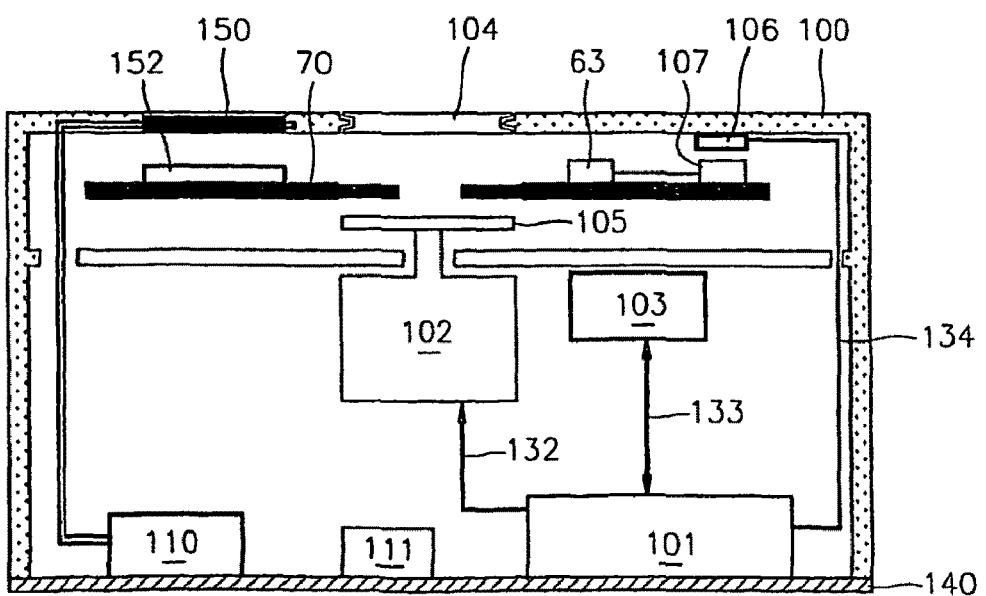

FIGS. 4A and 4B shows embodiments of a bio-driver, which is a mechanical device for rotating the disk of the assay devices described above. The electronic control device 63 transmits the measured frequency response characteristics to an external central controller 101 or storage device 111 through a non-contact interface, for example, an infrared interface or optical interface, which are located adjacent the central void 61 of the disk. Reference numerals 106 and 107 denote reception and transmission portions, respectively, of the non-contact interface. The reception and transmission portions 106 and 107 of the non-contact interface may be implemented with infrared sensors for infrared interfacing, or photosensors for optical interfacing.

In FIGS. 4A and 4B, embodiments of the supply of power to the electronic control unit 63 on the disk while it rotates are also shown. Reference numeral 100 denotes a driver body for supporting the bio-driver. A printed circuit board (PCB) 140 is connected to the driver body 100 below the bio-driver, and the central controller 101 for controlling the bio-driver and the storage unit 111 are mounted on the PCB 104. The central controller 101 controls a motor 102 to rotate the disk or stop rotation of the disk, controls movement of an optical device 103, and controls upper and lower rotors 104 and 105 such that they rotate adjacent the central void 651 of the disk upon rotation of the disk. The central controller 101 transmits the information read from the disk by the optical device 103 to the storage unit 111, or information to be written to the optical device 103, and provides a number of control signals required to read/write information to the other elements.

FIG. 4A shows an embodiment of the supply of power to the electronic control unit 63 on the disk by frictional contact between the upper and lower rotors 104 and 105 and respective brushes 108 and 109. In FIG. 4A, reference numeral 110 denotes a power supply unit for supplying a DC power to the brushes 108 and 109, and reference numerals 227 and 228 denotes arms. Alternatively, one of the upper and lower rotors 104 and 105 may be used. In this case, two opposite nodes of the power supply unit 110 are connected to one brush.

Figure 4C:
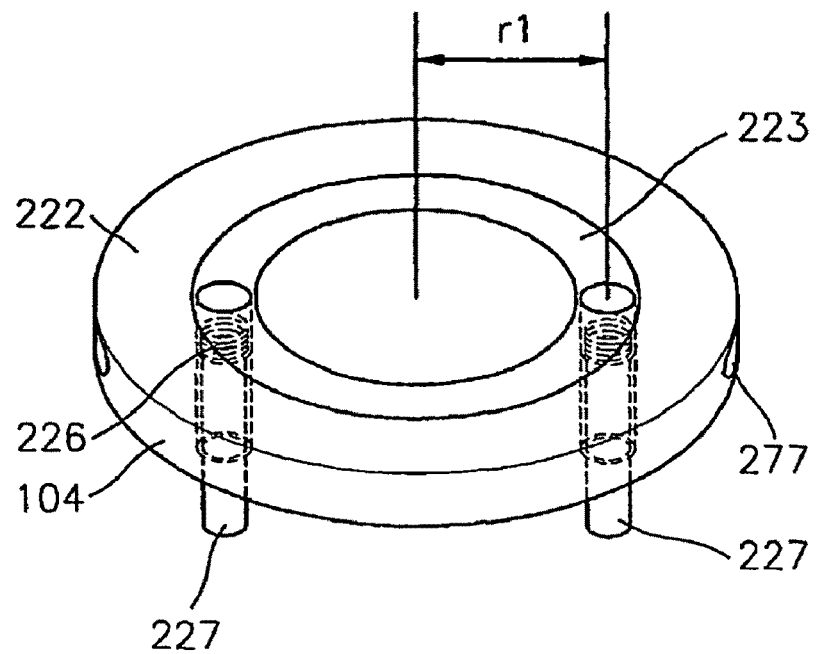
Figure 4D:
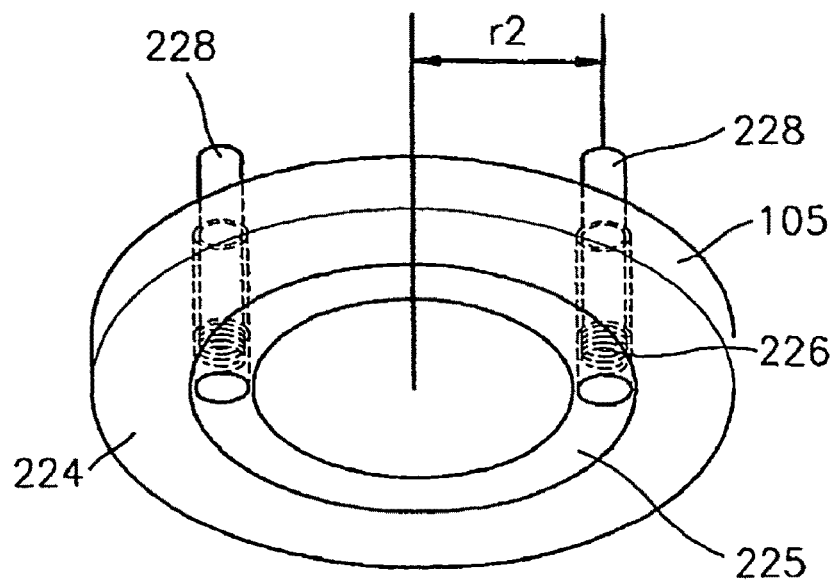

FIGS. 4C and 4D show embodiments of the supply of power to the electronic control unit 63 mounted on the disk by frictional contact between the upper rotor 104 and the brush 108, and between the lower rotor 105 and the brush 109, respectively. In particular, in FIG. 4C, an annular electrode plate 223 mounted on a top plate 222 of the upper rotor 104 to frictionally contact the brush 108 is shown. The two conductive arms 227 connected to the annular electrode plate 223 act as connectors to engage holes 302, which are described later, formed near the central void 61 of the disk. The annular electrode plate 223 has a radius of r1. Reference numeral 277 denotes a groove which supports the upper rotor 104 against the driver body 100. In FIG. 4C, an annular electrode plate 225 mounted on a bottom plate 224 of the lower rotor 105 to frictionally contact the brush 109 is shown. The two conductive arms 229 connected to the annular electrode plate 225 act as connectors to engage holes 301, which are described later, formed near the central void 61 of the disk.

Figure 4E:
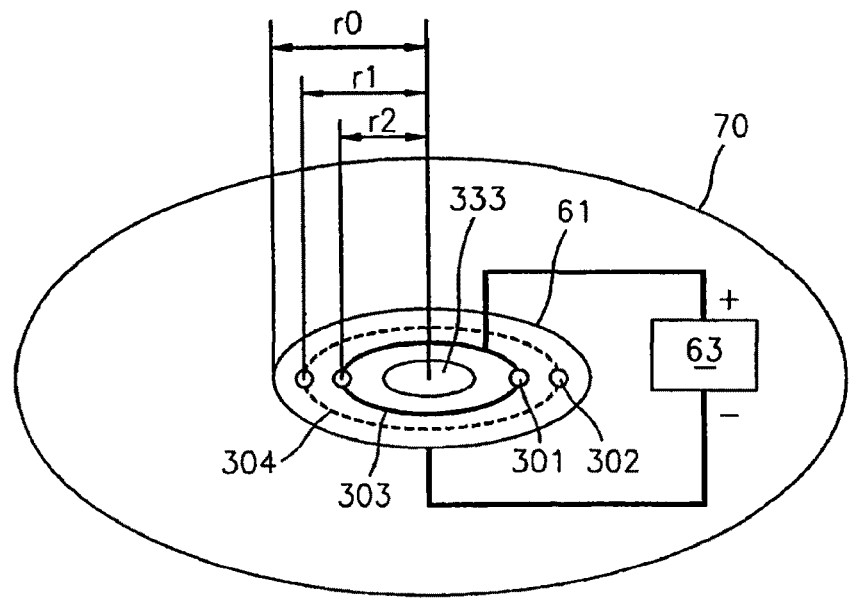

FIG. 4E shows the holes 301 and 302 to engage the conductive arms 227 and 229, respectively, formed in the central void 61 of the disk. The central void 61 has a radius of r0. Reference numeral 333 denotes a hole in the central void 61.

As the disk starts to rotate, the conductive arms 227 and 228 rotate while being engaged with the holes 301 and 302 as the upper rotor 104 and the lower rotor 105 are pushed closer together. A negative (ground) voltage is applied to the conductive arm 227 connected to the upper rotor 104, whereas a positive voltage is applied to the conductive arm 228 connected to the lower rotor 105. The holes 301 and 302 of the disk, which are engaged with the conductive arms 227 and 228, are connected to circuit patterns 303 and 304 to thereby supply power to the electronic control unit 63. To make the holes 301 and 302 engage easier with the conductive arms 227 and 118 when the upper rotor 104 and the lower rotor 105 are pushed closer together upon rotation of the disk. The conductive arms 227 and 228 have a spring 226 at its one end connected to the respective annular electrode plates 223 and 225.

FIG. 4B shows an embodiment of the supply of power to the electronic control unit 63 where an AC voltage is induced to a wound coil 152 on the disk and rectified by magnetic induction between an electromagnet 150 attached to the driver body 100 and the wound coil 152 to thereby supply power to the electronic control unit 63 in a non-contact manner. In FIG. 4B, reference numeral 110 denotes a power supply unit for supplying an AC current to the electromagnet 150.

Figure 4F:
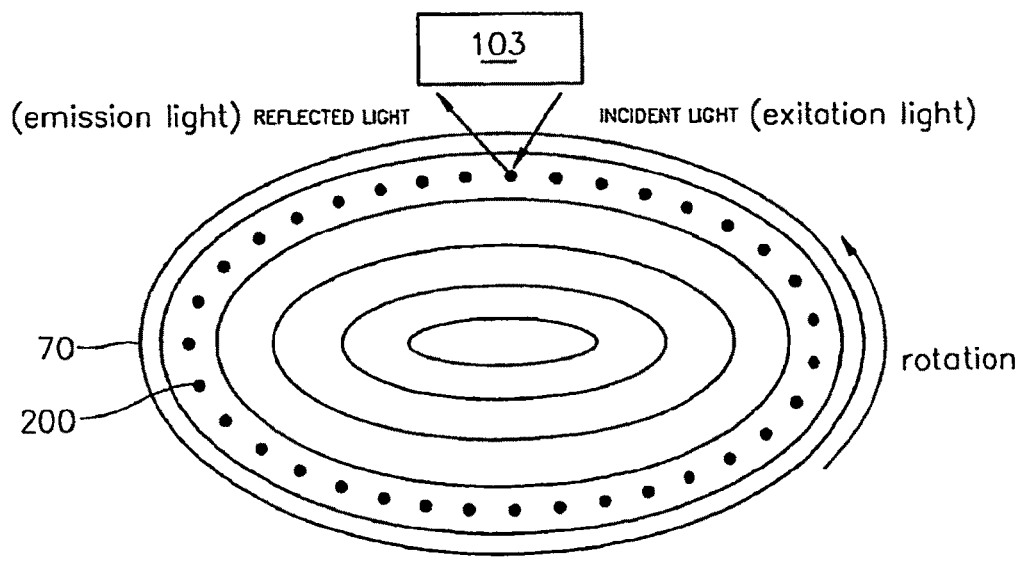
FIG. 4F shows an implementation of detection of analyte-specific signals generated by the assay device using an optical device.

FIG. 4F shows an implementation of detection of analyte-specific signals generated by the assay device of FIG. 3A, 3B, or 3D using the optical (or fluorescent) device 103. The optical device 103 is provided with differentially reflective (fluorescent) signals between the uncleaved signal element 66 and the cleaved signal element 65 with respect to incident light, in particular, incident laser light. The optical device 103 may include a light source, an incident light emitting portion, and a reflective light receiving portion.

Figure 5A:
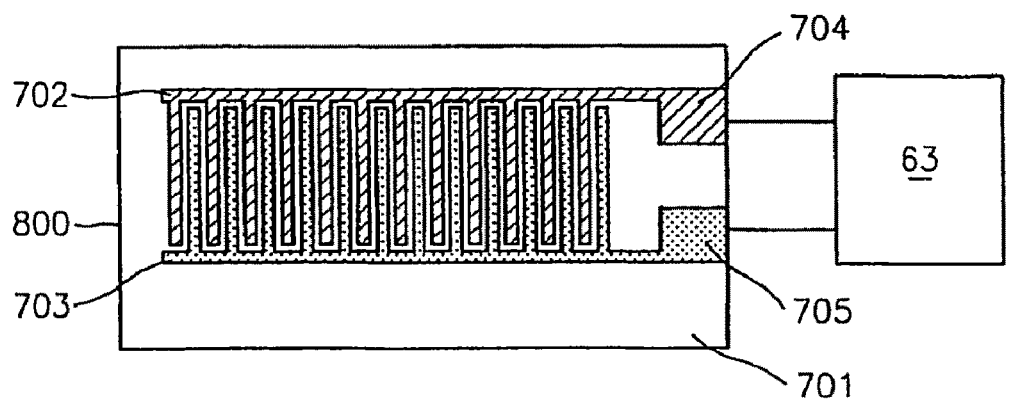
FIGS. 5A through 5I show alternative embodiments of the detection of analyte-specific signals generated by the assay device of FIG. 3C using a capacitance and impedance measurement device having interdigitated array electrodes.

FIGS. 5A through 5G show alternative embodiments of the detection of analyte-specific signals generated by the assay device of FIG. 3C using a capacitance and impedance measurement device having interdigitated array electrodes. In particular, FIG. 5A shows an embodiment of the capacitance and impedance measurement device implemented by interdigitated array electrodes 702 and 703 and a plurality of cleavable signal elements. The cleavable signal elements are attached to digits between the interdigitated array electrodes 702 and 703. The sensitivity of the detector increases with more digits.

Capacitance and impedance can be determined by measuring the frequency characteristics of the sample with application of AC signals having a predetermined bandwidth from the electronic control unit 63 to two input ports 704 and 705 of the interdigitated array electrodes 702 and 703.

Figure 5B:
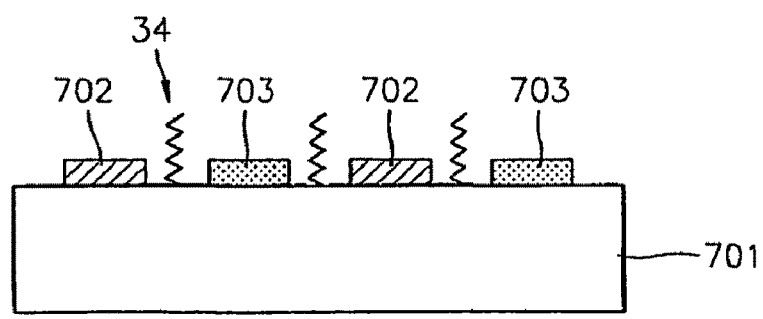
Figure 5C:
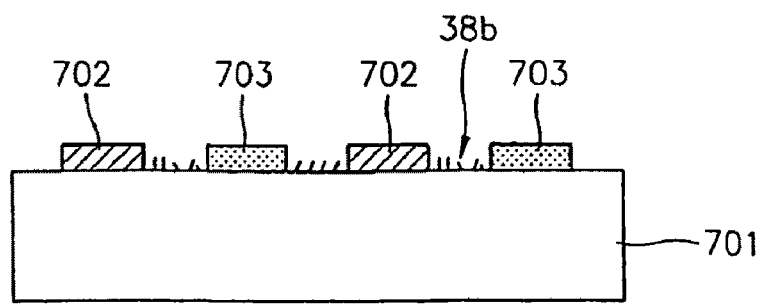

FIG. 5B shows a state where the uncleaved signal element 34 remains between the interdigitated array electrodes 702 and 703 on the surface of a substrate 701. FIG. 5C shows a state where only a cleaved residue 38b remains after most of the cleavable signal element is has been detached. The electronic control unit 63 is provided with the differential frequency response characteristics between the uncleaved signal element 34 and the cleaved signal element 38b.

Figure 5D:
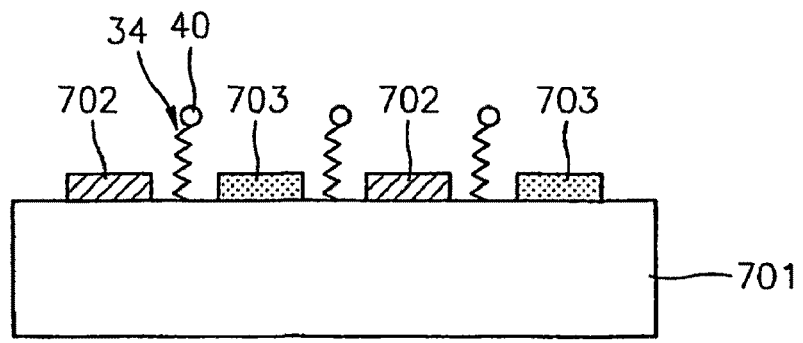
Figure 5E:
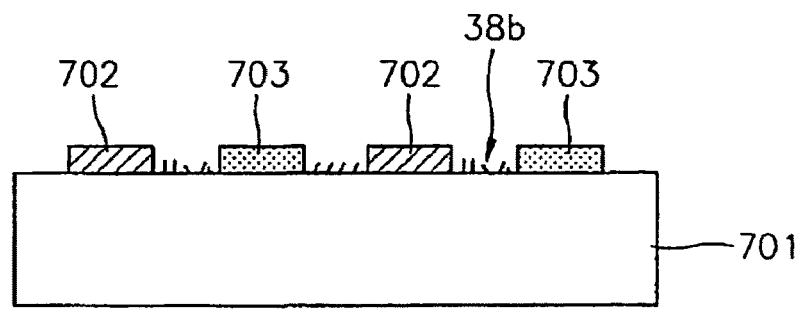

FIGS. 5D and 5E are for illustrating an embodiment of the capacitance and impedance measurement device implemented with interdigitated array electrodes and cleavable signal elements having one end labeled with a label 40 such as a metal microsphere, conducting polymer (e.g., polyaniline), or a fluorescent label. FIG. 5D shows a state where the uncleaved signal element 34 remains on the surface of the substrate 701 after cleavage of the cleavable signal elements and washing. FIG. 5E shows a state where the cleavable signal element has been detached.

Figure 5F:
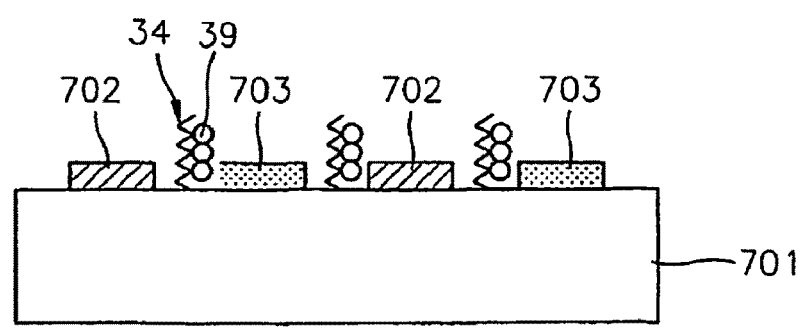
Figure 5G:
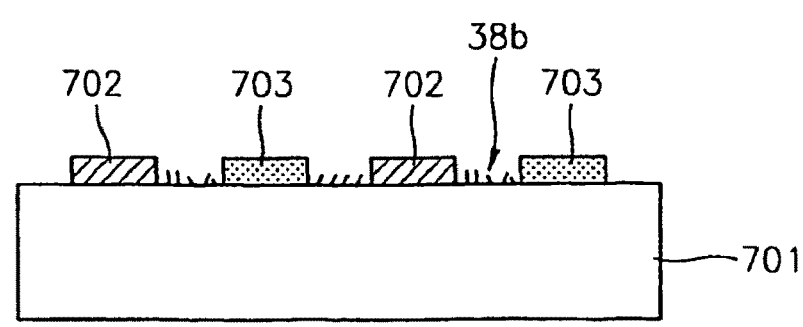

FIGS. 5F and 5G is for illustrating an embodiment of the capacitance and impedance measurement device implemented with interdigitated array electrodes and a "label-attached uncleaved probe" structure formed through additional contact between the uncleaved signal element 34 and a label 39 after cleavage and wash steps. FIG. 5F shows a state where the uncleaved signal element 34 remains on the surface of the substrate 701 being labeled with the label 39. FIG. 5G shows a state where the cleavable signal element has been detached.

Figure 5H:
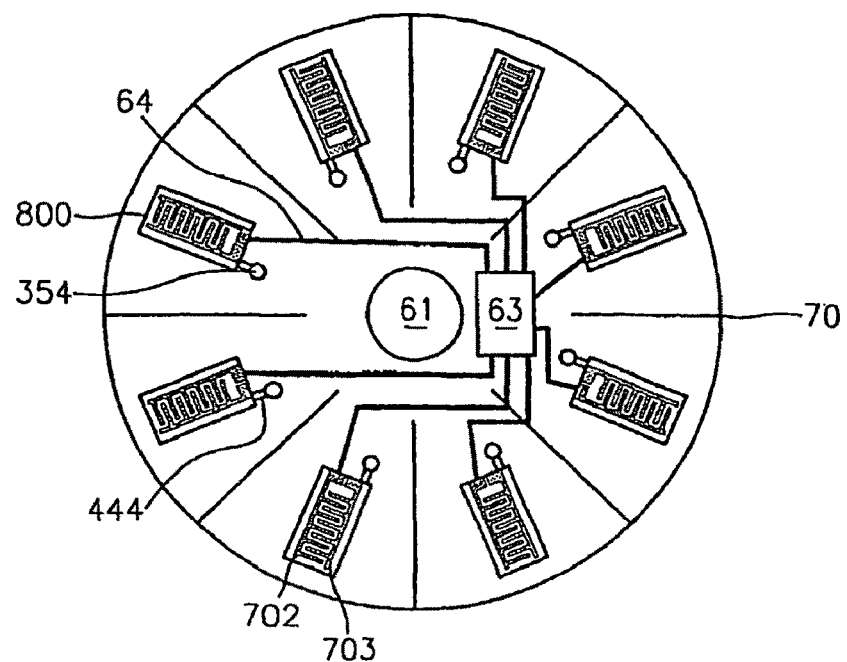

FIG. 5H shows an embodiment of arrangement of a plurality of assay sectors 800 on the disk, each including a pair of interdigitated array electrodes 702 and 703. Each of the assay sectors 800 may be constructed by combination of multiple pairs of interdigitated array electrodes 702 and 703 for multiple-analyte assay.

To enable the detector including the capacitance and impedance measurement device constructed with the interdigitated array electrodes 702 and 703 to electrically measure whether the cleavable signal element is cleaved or not, circuit patterns 64 which connect the electronic control unit 63 to each of the detectors arranged in the assay sectors 800, are imprinted in the substrate 70 of the circular disk. The electronic control unit 63 measures the capacitance and impedance with respect to each of the assay sectors 800 by checking for the frequency response characteristics from the assay sectors 800 and thereby obtains information on whether the cleavable signal element is cleaved or not or information on the degree of cleavage. In FIG. 5H, reference numeral 354 denotes a sample injection port, and reference numeral 444 denotes a sample inflow channel. Although multiple sample injection ports 354 are illustrated in FIG. 5H, only one simple injection port may be formed to assay a signal sample for multiple analytes.

Figure 5I:
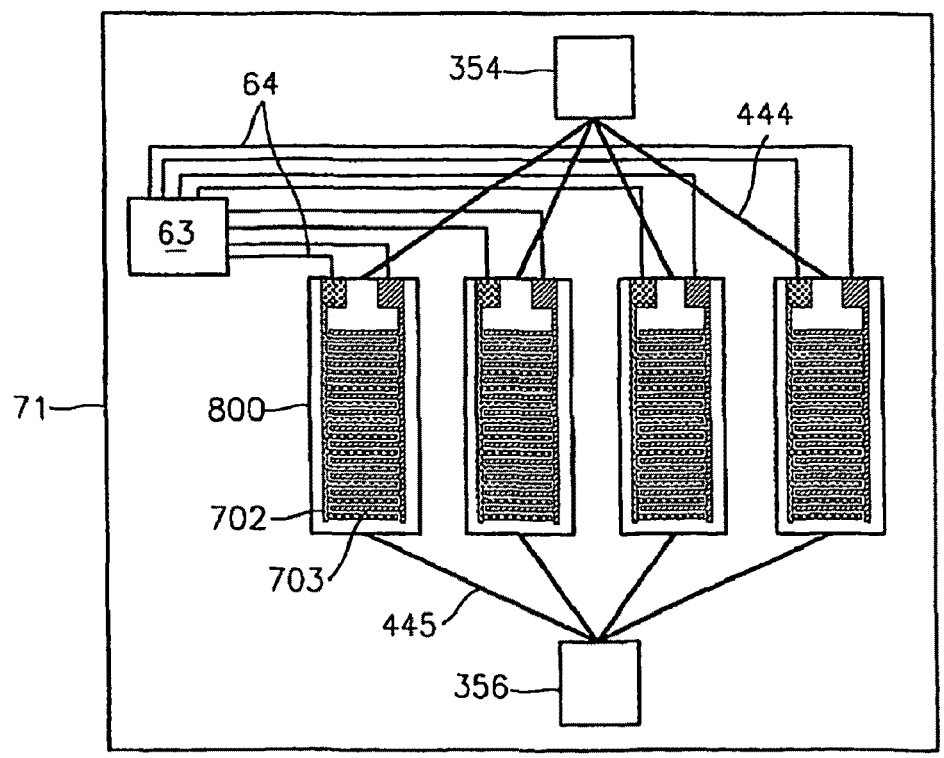

FIG. 5I shows an embodiment of the capacitance and impedance measurement device in which a plurality of assay sectors 800, each including the interdigitated array electrodes 702 and 703, are arranged on a solid support 71 of a common shape. The electronic control unit 63 and circuit patterns 64 which connect the electronic control unit 63 to each of the detectors including the capacitance and impedance measurement device and arranged in the assay sectors 800, are mounted in the solid support 71, so that whether the cleavable signal element is cleaved or not can be measured using the converter. The electronic control unit 63 measures the capacitance and impedance with respect to each of the assay sector 800 by checking for the frequency response characteristics from the assay sectors 800 and thereby obtains information on whether the cleavable signal element is cleaved or not or information on the degree of cleavage. In FIG. 5I, reference numeral 354 denotes a sample injection port, reference numeral 444 denotes a sample inflow channel, reference numeral 356 denotes a sample exhaust port, and reference numeral 445 denotes a sample exhaust channel.

Figure 6A:
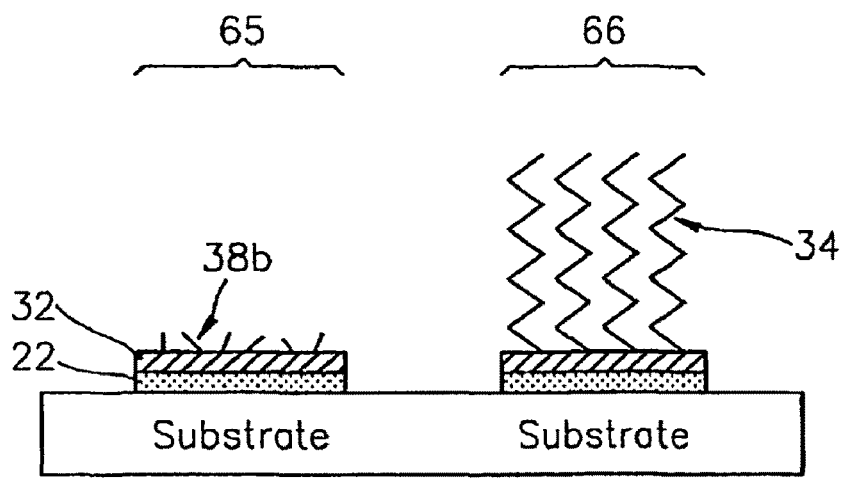
FIGS. 6A and 6B show alternative embodiments of implementation of the differential reflection between an uncleaved signal element and a cleaved signal element.
Figure 6B:
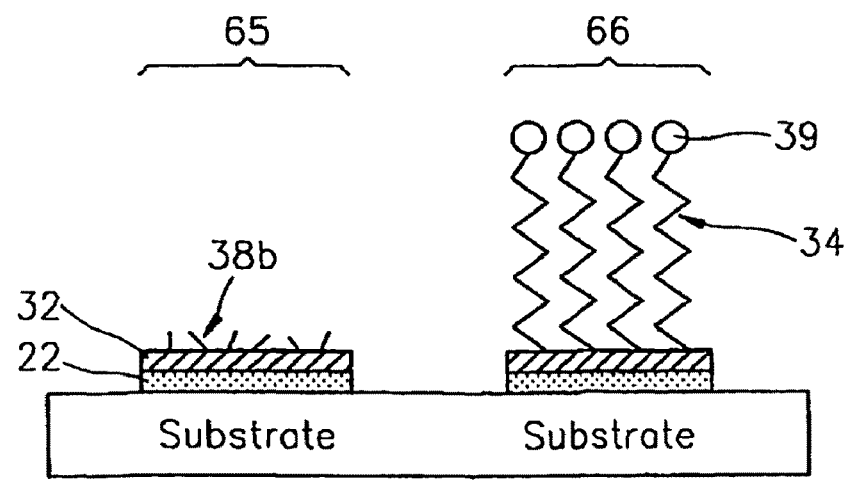

FIGS. 6A and 6B show alternative embodiments of implementation of the differential reflection between a cleaved signal element and an uncleaved signal element. Referring to FIG. 6A, a gold layer 22 and a self-assembled monolayer (SAM) 32 are sequentially formed on a substrate, and a cleavable signal element 34 is immobilized on the SAM 32. Reference numeral 65 denotes a cleaved signal element having a cleaved residue 38b left after the cleavable signal element has been detached. Reference numeral 66 denotes an uncleaved signal element. FIG. 6B illustrates the application of a label 39, such as a metal microsphere, conducting polymer, or fluorescent label, to increase the sensitivity of the detector. As shown in FIG. 6B, the gold layer 22 and the SAM 32 are sequentially formed on the substrate, and a cleavable signal element 34 is immobilized on the SAM 32. Reference numeral 65 denotes a cleaved signal element having a cleaved residue 38b left after the cleavable signal element has been detached. Reference numeral 66 denotes an uncleaved signal element.

Figure 6C:
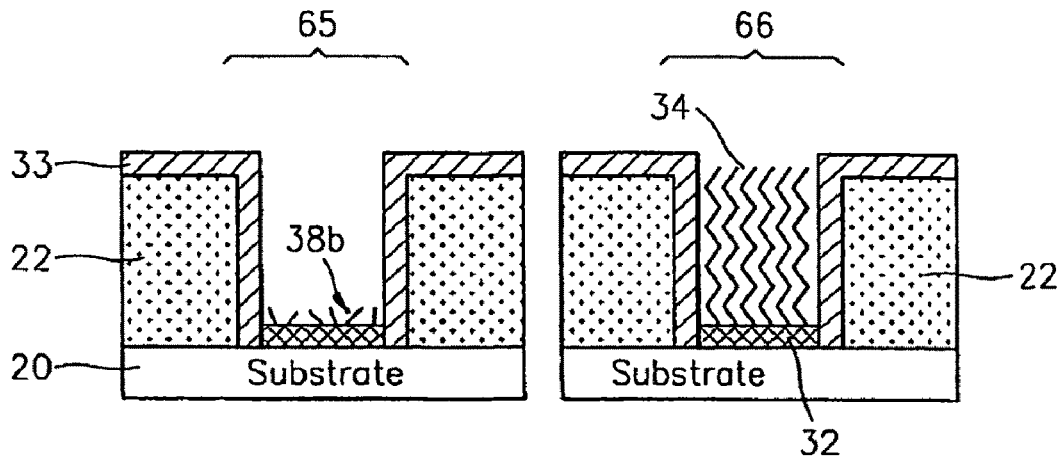
FIGS. 6C through 6E show alternative embodiments of implementation of the differential conductance (impedance or capacitance) between the uncleaved signal element and the cleaved signal element using the interdigitated array electrodes.
Figure 6D:
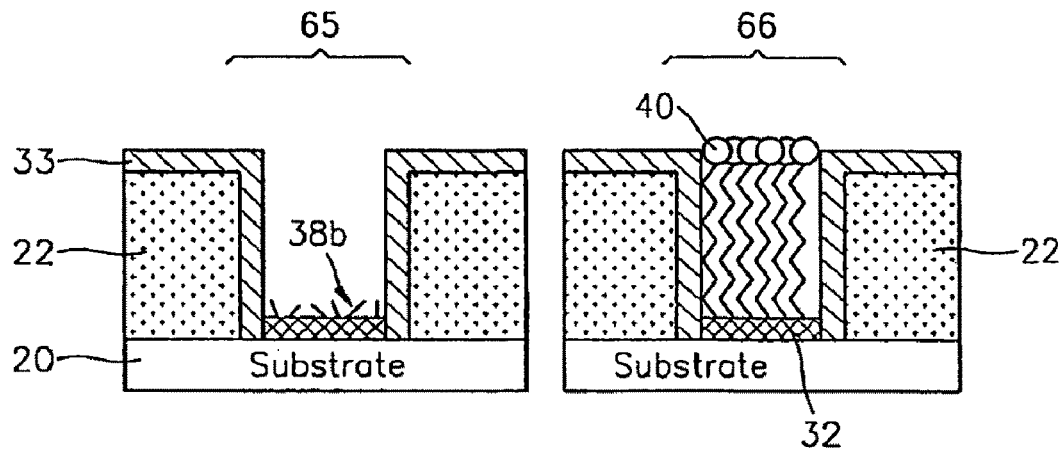
Figure 6E:
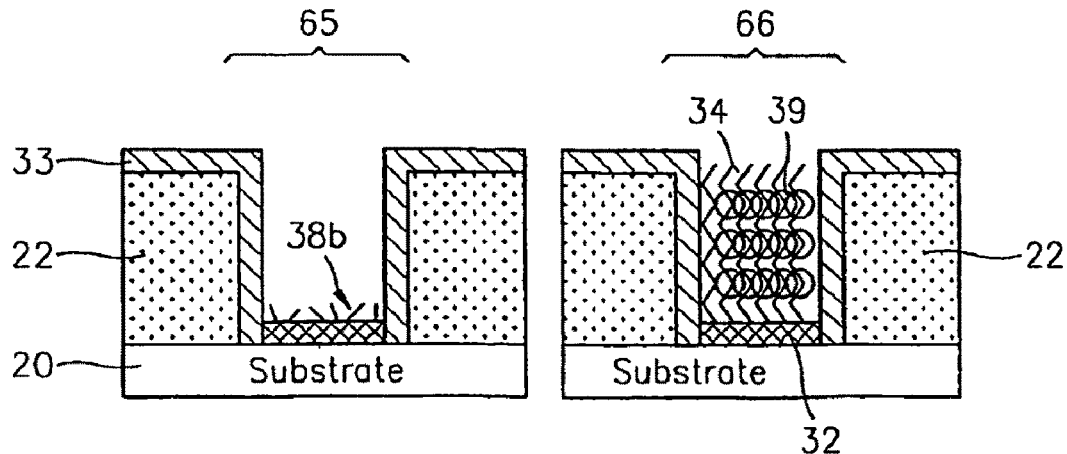

FIGS. 6C through 6E show alternative embodiments of implementation of the differential conductance (impedance or capacitance) between the cleaved signal element and the uncleaved signal element using interdigitated array electrodes. Referring to FIG. 6C, the gold layer 22 and the SAM 32 for immobilization of the cleavable signal element 34 are formed on a substrate 20. The gold layer 22 constitutes the interdigitated array electrodes. A protective layer 33 is formed to protect the gold layer 22 from the cleavable signal element 34 adhering to the gold layer 22. As shown in FIG. 6C, which is a partial cross-sectional view of the assay sector 800 of FIG. 5A, only a cleaved residue 38b of a cleaved signal element 65 remains after the cleavable signal element has been detached. Reference numeral 66 denotes an uncleaved signal element.

FIG. 6D shows an embodiment of labeling one free end of the cleavable capture probe, which constitutes a cleavable signal element whose the other end is attached to the substrate, with a label 40 such as a metal microsphere, conducting polymer, or fluorescent label to increase the sensitivity of the detector. FIG. 6E shows an embodiment of formation of a "label-attached uncleaved probe" structure after washing by additional labeling of the uncleaved signal element 66 with a label 39, such as a metal microsphere, conducting polymer, or fluorescent label. As shown in FIGS. 6D and 6E, which are partial cross-sectional views of the assay sector 800 of FIG. 5A, only a cleaved residue 38b of a cleaved signal element 65 remains after the cleavable signal element has been detached. Reference numeral 66 denotes an uncleaved signal element labeled with the label 40 or 39.

Figure 7A:
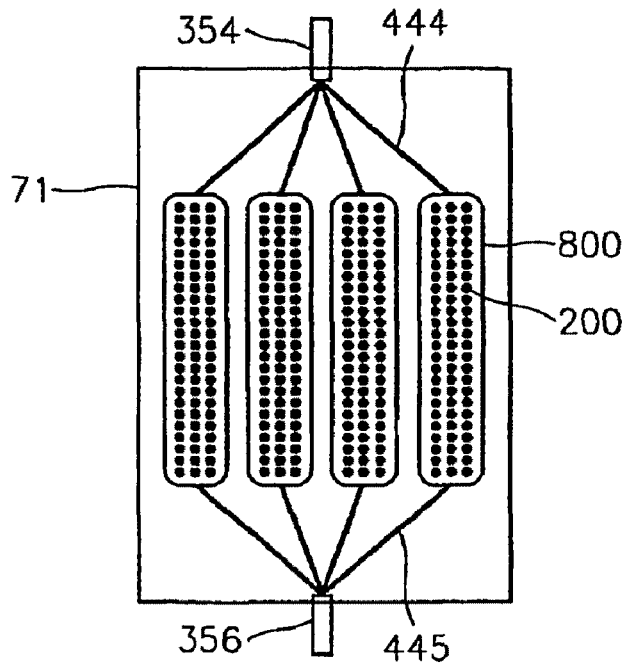
FIG. 7A illustrates the arrangement of four separate assay sectors in an assay device, each containing a different cleavable signal element, to assay in parallel a single sample for four different analytes.

FIG. 7A illustrates the arrangement of four separate assay sectors in an assay device, each containing a different cleavable signal element 200, to assay in parallel a single sample for four kinds of analytes. The single sample injected through the sample injection port 354 is supplied to each of the assay sectors through the sample inflow channel 444. On each of the assay sectors 800, the cleavable signal element 200 having a capture probe complementary to a different analyte is deposited. Preferably, the cleavable signal element 200 is fluorescently detected. In this case, a fluorescent label is applied to the end of the cleavable signal element 200, as illustrated in FIG. 2A. The assay device of FIG. 7A includes a sample exhaust port 356 and a sample exhaust channel 445. Alternatively, different kinds of cleavable signal elements 200 that are complementary to a plurality of discrete analytes may be deposited within one assay sector to enable multi-analyte assay in a single assay sector.

Figure 7B:
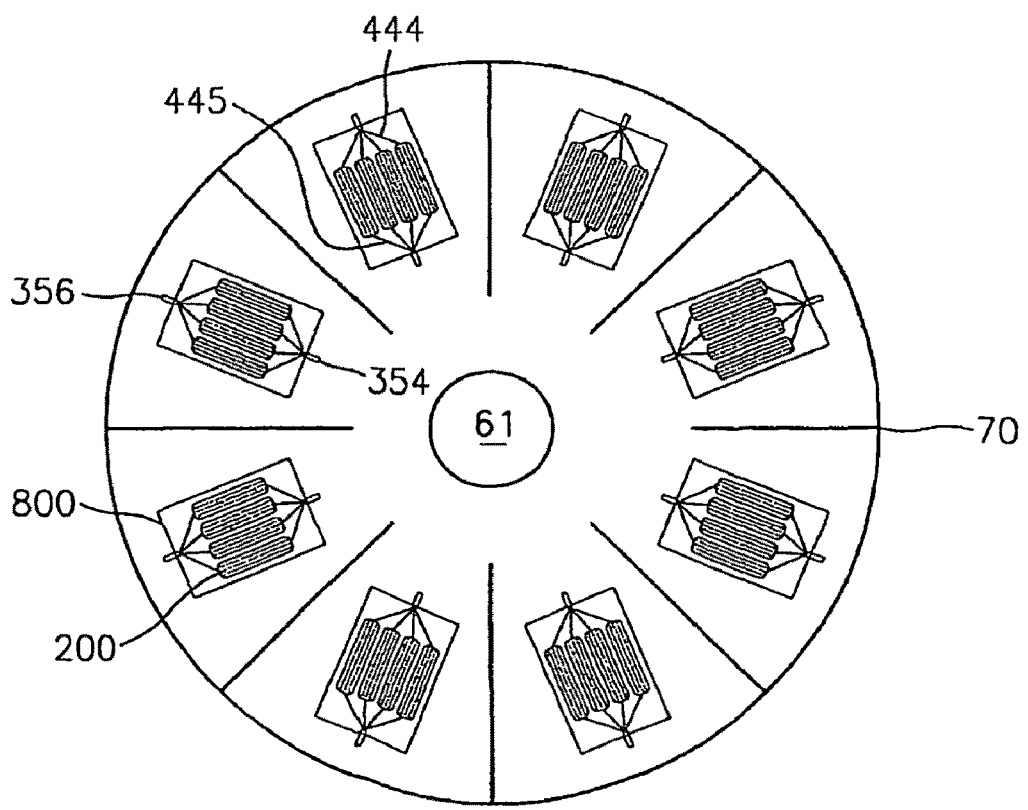
FIG. 7B shows an embodiment of the arrangement of the assay device of FIG. 7A on a disk.

FIG. 7B shows an embodiment of the assay device according to the present invention, in which a plurality of assay devices of FIG. 7A are radially arranged on a disk.

Figure 8:
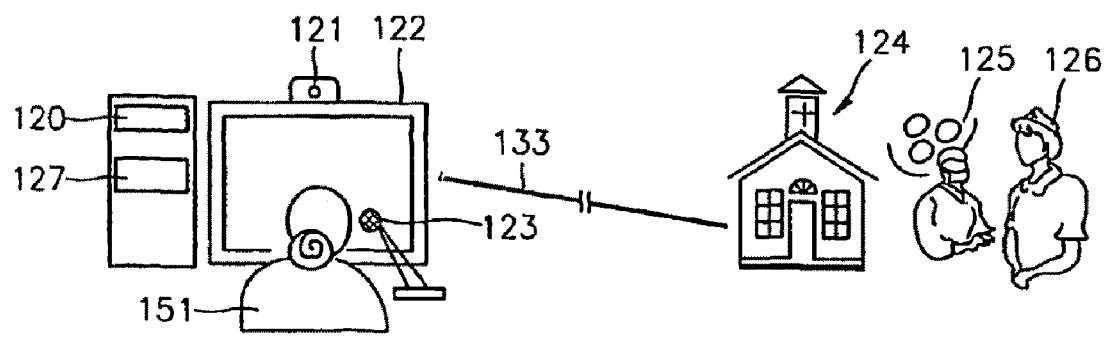
FIG. 8 shows an embodiment of a remote diagnostic system according to the present invention, in which the information read by a detector of the assay device is digitalized as computer software and mutually transmitted to and received by a patient and a doctor through an existing communication network, for example, the Internet.

FIG. 8 shows an embodiment of a remote diagnostic system according to the present invention, in which the information read from the assay device is digitalized as computer software and mutually transmitted to and received by a patient 151 and a doctor 125 through an existing communication network 133. In FIG. 8, reference numeral 120 denotes a detector including an optical device, an electrochemical device, a mass measurement device, or a capacitance and impedance measurement device, as described above, to detect the presence or absence of the cleavable signal element on the solid support (substrate). The detector 120 may be a bio-driver including a central controller and an assay device in the form of disk, bio-CD, or bio-DVD where analyte-specific cleavable signal elements are spatially and addressibly arranged in a variety of ways. Reference numeral 127 denotes a software-installed hard disk driver (HDD) or memory. The software may include assay interpretive algorithms, bioinformatics information, and self-diagnostics related information. The software may further include software capable of uploading the diagnostic information to remote locations and device drivers. The software may include educational information for patients on clinical assays, and may be modified for chosen audiences. The software may include a variety of wet sites and links, for example, enabling a patient to communicate with a doctor or hospital based on his/her diagnosis result. Reference numerals 121 and 123 denote a camera and a microphone for viewing a patient's face and listening to his/her voice, respectively. Reference numeral 15i denotes a patient. A hospital 124, a doctor 125, and a nurse 126, which provide remote diagnosis services, are also shown in FIG. 8.

<Method of Applying Sample>

A cleavable signal element according to the present invention is suitable for detecting, in particular, a nucleic acid amplified to a limited size through an amplification scheme using a variety of polymerase chain reactions (PCRs), ligase chain reactions (LCRs), and T7 and SP6RNA polymerases.

In an assay method according to the present invention, a sample to be tested is first introduced. After a dilute fluid sample is applied near the center of the substrate (solid support) of a circular, disk-type assay device, the assay device is rotated. The fluid sample evenly diffuses over and uniformly covers the surface of the substrate by a centrifugal fore generated by the rotation of the assay device.

In this method of applying the sample, 100 μL of the test sample is diluted to about 1 mL. This dilute sample is dropwise added near the center of the disk. The assay sites and the surface of the disk are hydrophilic, and the fluid sample forms a thin fluid film on the rotating disk. The thickness of the fluid film can be adjusted by the frequency of the dropwise addition and the frequency of disk rotation. Preferably, the thickness of the fluid film is less than 10 μm to permit all molecules in the fluid sample to react with the cleavable signal element. About 10 μL of the fluid sample is needed to fully cover the surface of the disk. This sample apply method is suitable for, in particular, the assay devices of FIGS. 3A through 3D and FIG. 5F.

Another sample apply method is available with the cleavable signal element and assay device according to the present invention, in particular, the assay devices of FIGS. 3B, 3C, and 5H, each of which includes 8 separate assay sectors 800 and is suitable to apply a single sample to each assay sector.

In other aspects of the present invention, separate samples may be applied to discrete sites of the disk-type assay device. In view of this, the assay device according to present invention can assay approximately one thousand different samples. In addition, to increase the sensitivity of the detector, approximately one million gold microspheres, conducting polymers, or fluorescent labels can be applied to label assay sites.

As an embodiment, the assay device of FIG. 3D, which has at the assay sites on the disk a plurality of cleavable signal elements with identical capture probes conferring identical analyte specificity, may be designed to concurrently assay 1024 patient samples. In other words, the assay device of FIG. 3D may include 1024 cleavable signal elements on the disk. In such an embodiment, each of the capture probes on the disk may be identical, so as to assay for the same analyte. Capture probes at particular sites on the disk have the same oligonucleotide sequence as those at other sites on the disk. This application is particularly useful in mass analysis conducted in clinical laboratories where a large number of patient samples are analyzed at the same time for the presence or absence of a single analyte.

Patient samples may be applied to particular assay sites on the disk by a known method, such as ink jet printing, micropipet arrays with disposable tips, or a combination thereof.

Alternatively, the assay device of FIG. 3D may be applied to assay a single sample for multiple analytes by using a plurality of diverse, cleavable signal elements specific to different analytes for each assay device.

<Hybridization>

In a nucleic acid hybridization assay according to the present invention, after the sample injection, rotation of the disk is halted, and the disk is incubated in a stationary state at room temperature for hybridization reaction between the capture probe and the complementary target nucleic acid in the sample.

<First Wash Step>

The nucleic acid hybridization assay according to the present invention involves first and second wash steps. After the even application of the sample over the disk surface and an appropriate incubation period for the hybridization, a first wash step is necessary. For example, in nucleic acid hybridization assays, at a lower salt concentration of the wash solution, washing is smooth, thus reducing mismatch as between analyte (target nucleic acid) and capture probes. In contrast, at a higher salt concentration, washing is not smooth, thereby permitting mismatch to occur. Adjusting the stringency of wash in nucleic acid hybridization assays, in terms of salt concentration, is well within the skill in the art.

In one aspect according to the present invention, the surface of the circular, disk-type assay device may be washed by adding a wash solution near the center of the rotating disk. The sample solution is removed as it pushes out from the periphery of the disk and is collected. Because of the rotation of the disk, the wash step may be eliminated if the fluid sample is adequately removed from the disk by centrifugal force. This centrifugal force is strong enough to mechanically denature mismatching oligonucleotides.

Alternatively, mismatching oligonucleotides may be removed with application of an external electric field. Due to the nature of its phosphate backbone which is negatively charged, the sample oligonucleotides hybridized to the cleavable signal element with a weak binding force can be denatured by applying an external negative electric field.

Figure 9:
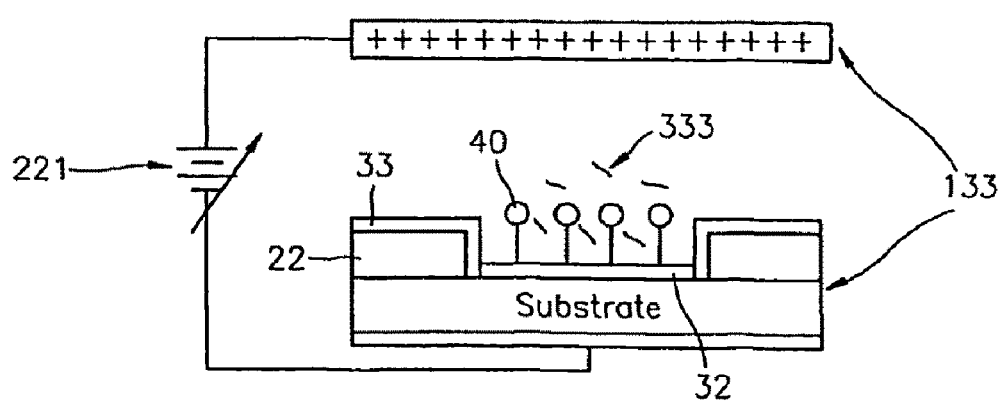
FIG. 9 illustrates a washing method by external electric field application.

As is shown in FIG. 9, the external electric field is applied with an electrode plate 133, disposed directly above the assay device, and an external voltage source 221. FIG. 9 shows an embodiment of washing away mismatching oligonucleotides 333 from the assay device of FIG. 6D with application of an external electric field.

<DNA Extension Step>

When a restriction enzyme specifically responsive to a particular sequence of a double stand is used according to the present invention, DNA extension is needed after the hybridization and first wash step. In DNA extension, a single-stranded restriction probe is double-stranded using the target nucleic acid previously hybridized to the capture probe as a primer with addition of a DNA polymerization solution containing four dNTPs and a polymerase.

Figure 12:
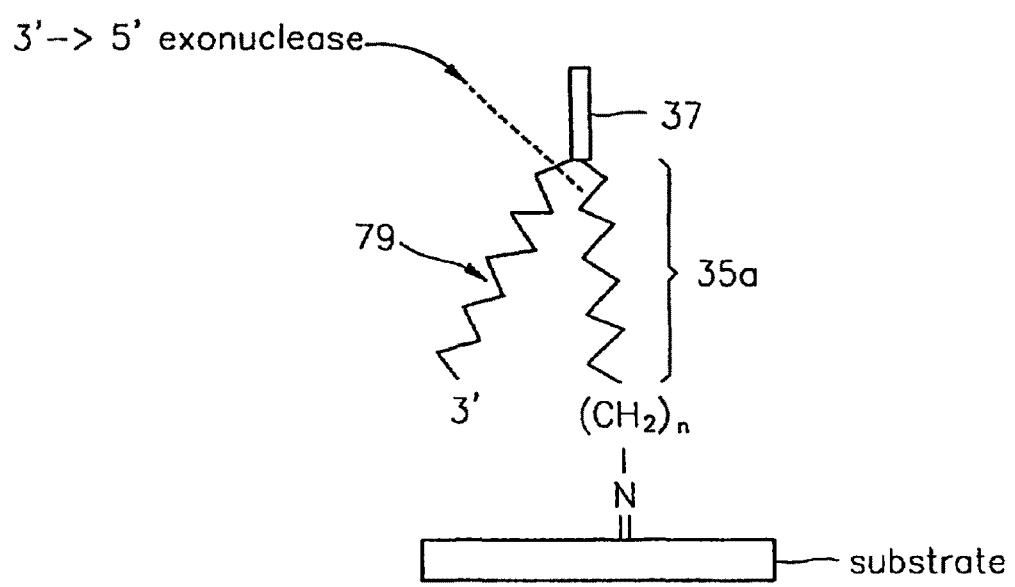
FIG. 12 shows the reaction mechanism of the 3'-5' exonuclease.

Prior to addition of the DNA polymerization solution, it is preferable to contact the restriction probe with a 3'-5' exonuclease solution. As is shown in FIG. 12, a step of hydrolytic cleaving a single-strained target nucleic acid portion 79, which is unbound to the capture probe, by addition of the 3'-5' exonuclease solution, may be further included before the DNA extension. The result is readily applied to DNA extension using the target nucleic acid previously hybridized to the capture probe as a primer.

<Cleavage Step>

After the first wash step (or DNA extension), a solution containing a restriction enzyme or cleavage enzyme (DNAse or nuclease) is added and distributed over the surface of the disk. The disk is incubated in a stationary state at room temperature, and the complementary double strand or single strand resulting from the hybridization is specifically cleaved. This enzymatic cleavage is maintained for a few seconds.

<Second Wash Step>

After the enzymatic cleavage step, a second wash step is needed to remove the cleaved signal elements. In this second wash step, differential wash stringencies are provided to permit variation in the specificity and sensitivity of the nucleic acid hybridization assay.

The cleaved signal elements may be removed by rotating the assay device, with or without addition of wash solution, or by applying an external electric field. In this aspect, four parameters may be varied to provide differential wash stringency: label particle size (such as metal microspheres, conducting polymers, or fluorescent labels), rotational speed, the valency of capture probe attachment, and the intensity of external electric field.

Gold microspheres suitable for use in the cleavable signal element and assay device of the present invention are readily available in varying diameters from Aldrich Chemical Company, British BioCell International, Nanoprobes, Inc., ranging from 1 nm to and including 0.5-5 micrometers in diameter. Gold microspheres of lesser or greater diameter may be formed as needed in the present invention. At a given rotational speed, the largest gold microspheres experience larger centrifugal and drag forces and are removed before smaller microspheres with equal bonding. This provides a basis for differential stringency of wash, and also of quantitative analysis.

The centrifugal force affecting the gold microspheres may also be adjusted by rotation frequency so that the loose and weakly bound gold microspheres are removed. Only the capture probes which have bound to a complementary molecule from the sample will continue to bind the gold microspheres to the substrate.

Furthermore, while the above embodiments of the invention have been described with a single metal microsphere attached to the end of a single cleavable signal element, it should be appreciated that when gold microspheres are used in a preferred embodiment of the invention, thousands of cleavable signal elements may bind to one gold microsphere, depending upon its diameter. Thus, the stringency of the assay wash may be adjusted, at any given rotational speed, by varying the diameter of the gold microsphere, and by varying additionally the relative density of cleavable signal elements to gold microspheres. Thus, if virtually all cleavable signal elements under a certain gold sphere are connected by complementary molecules, the binding is very strong. If the cleavable signal elements are fixated only partially under a certain gold microsphere, the microsphere may remain or be removed depending on the radius of the microsphere and the frequency of rotation. Alternatively, ferromagnetic microspheres, gold-coated iron beads, or an iron alloy beads may be used instead of the gold microspheres. In this case, those probes detached through cleavage may be removed with application of a magnetic field.

<Detection Step>

After removal of cleaved signal elements through the second wash step, the disk may be read directly. Alternatively, the disk may be covered by an optically transparent plastic coating to prevent the further removal of the gold microspheres through spin coating with a polymerizable lacquer that is polymerized with UV-light. Spin coating of compact disks is well established in the art. The assay device disk is expected to have a shelf-life of over ten years.

Subsequently, the disk can be scanned by a laser reader which will detect, through reflection, the presence of a microsphere or other reflective elements at the various spatially predetermined locations. Based on the distance of the microsphere from the axis of rotation of the disk and the angular distance from an address line forming a radial line on the disk, the location of a particular metal microsphere can be specifically determined. Based on that specific location and the predetermined locations of specific binding pairs as compared to a master distribution map, the identity of the bound material can be identified. Thus, in the foregoing manner it is possible in one fluid sample to analyze for thousands, or even greater numbers, of analytes simultaneously.

<Additional Labeling Step>

In the case of forming the "label-attached uncleaved probe" structure, an additional step of labeling the cleavable signal element or uncleaved probe is included before sample injection or after cleavage. In particular, the additional labeling before sample injection follows the synthesis of the capture probe or capture probe attachment to the substrate (solid support). The additional labeling after cleavage requires a preceding sample washing step.

The nucleic acid hybridization assay according to the present invention involves the sample injection, hybridization, first wash and cleavage, additional labeling reaction, and second wash steps described above.

<Synthesis of Cleavable Signal Element and Attachment to Glass Substrate>

Figure 10A:
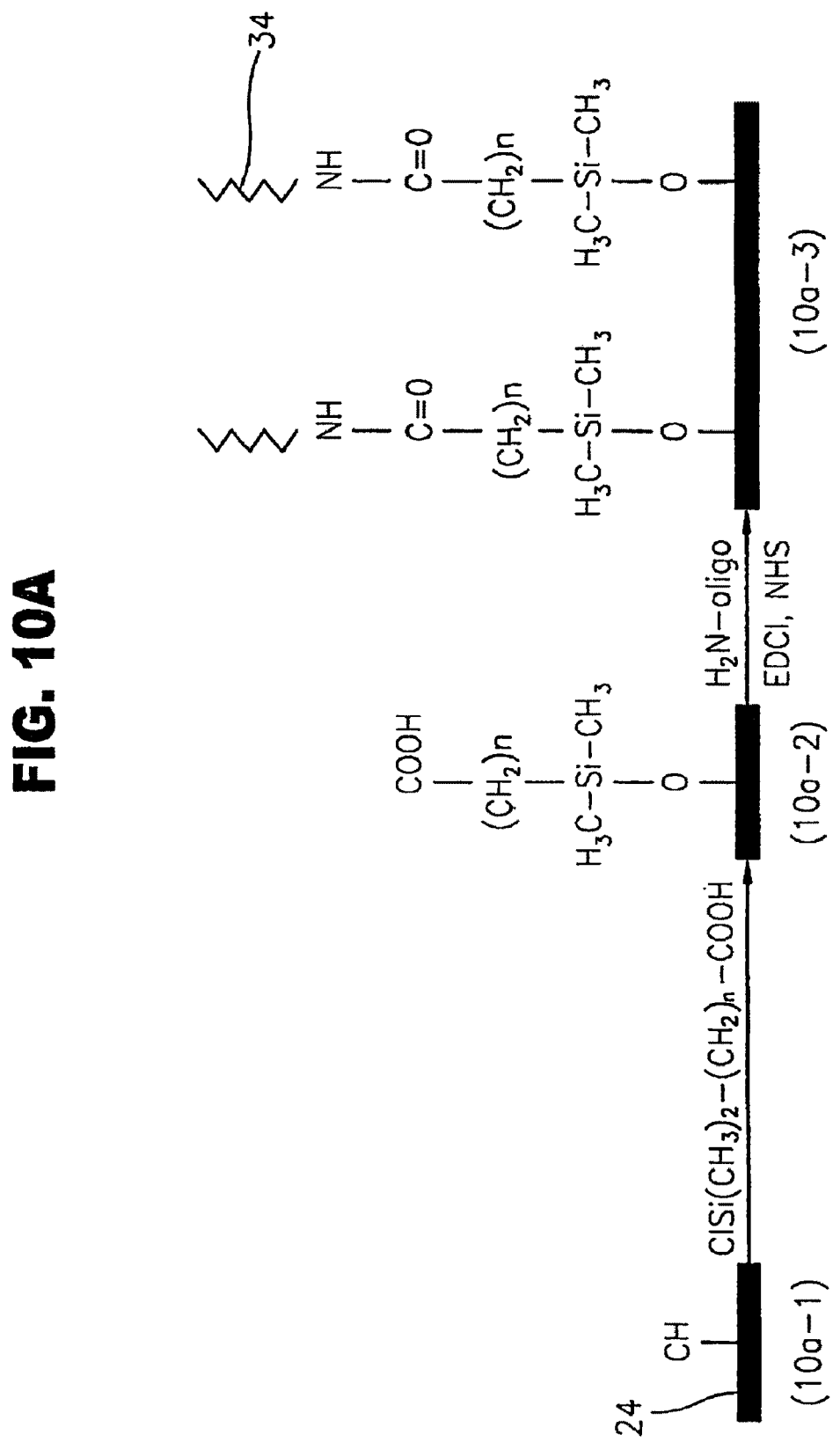
Figure 10B:
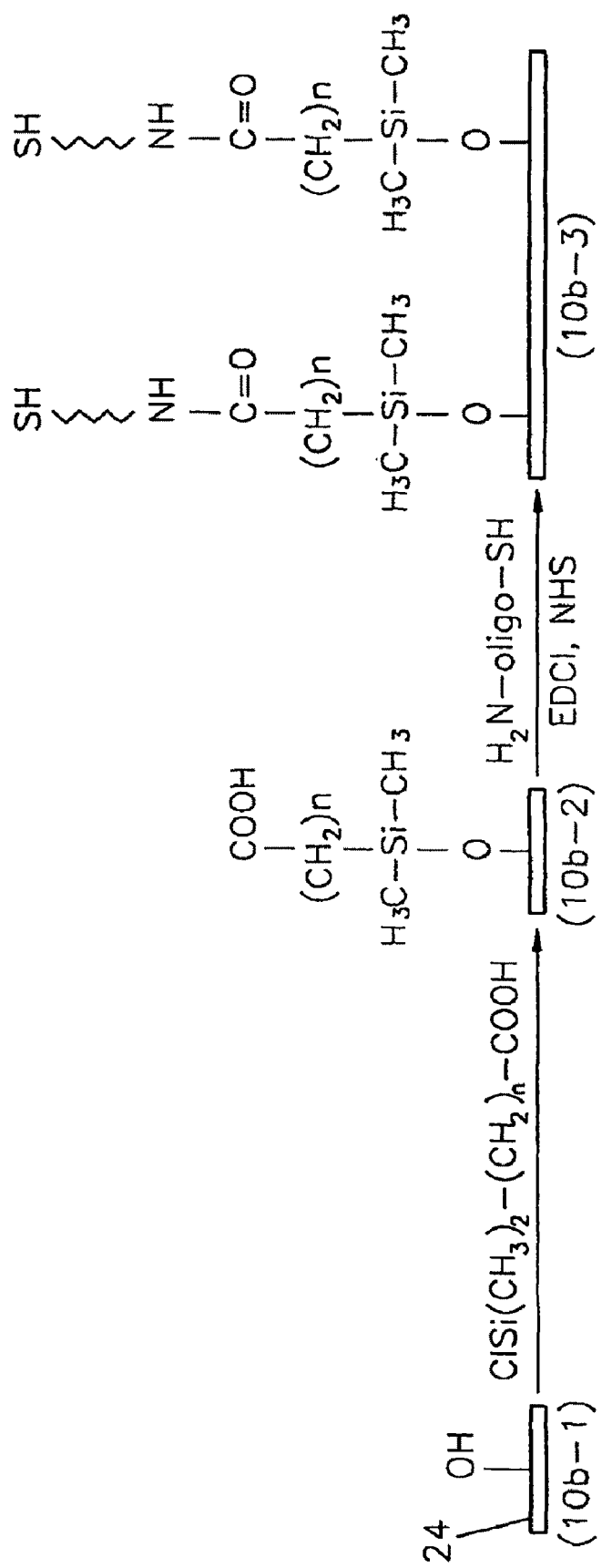
Figure 10C:
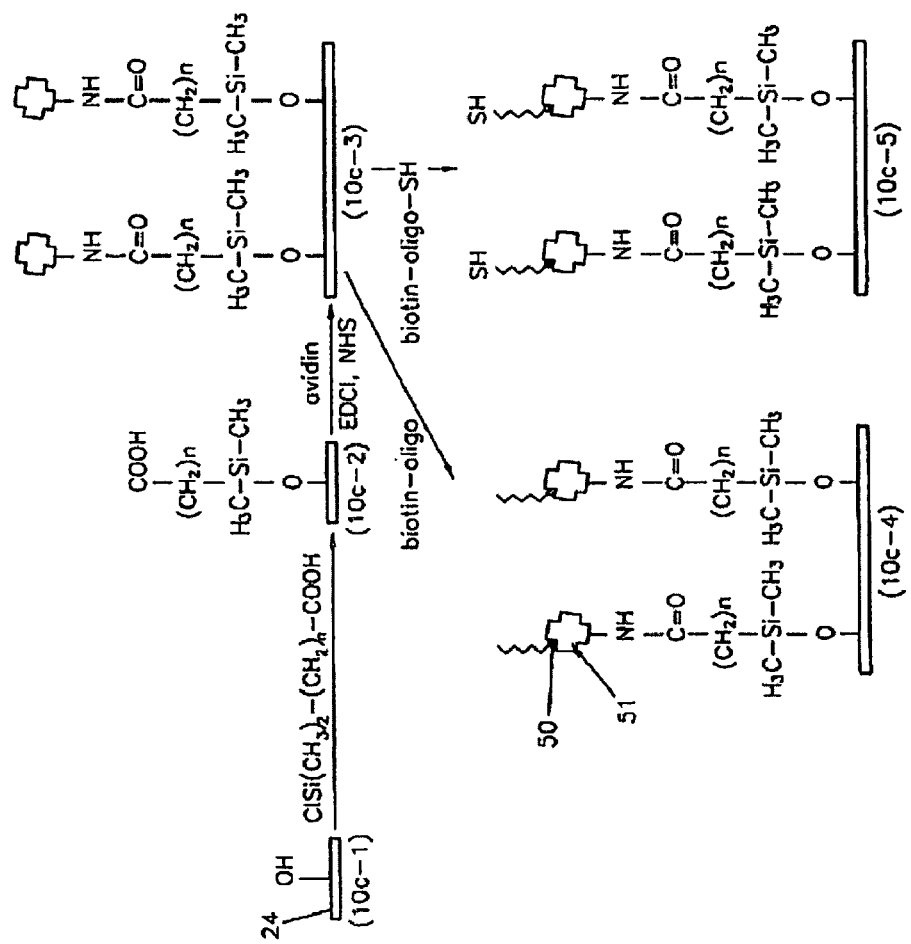

FIGS. 10A through 10C show alternative embodiments of the synthesis of cleavable signal elements and attachment to glass substrates.

1. Cleaning of Glass Substrate

A detergent (Alconox) is first dissolved in distilled water, and glass substrates are sonicated in the detergent solution for approximately 50 minutes. The glass substrates are rinsed with distilled water to remove any sticking detergent. The rinsed glass substrates are boiled or sonicated in a piranha solution (a 3:7 mixture of $H_2O_2$ and $H_2S_4$) for 30 minutes. For glass substrates coated with, for example, gold, the glass substrates are socked in the piranha solution for washing, without sonication. Next, the glass substrates are removed from the piranha solution and rinsed copiously with distilled water to completely remove the piranha solution from the glass substrate surface (Steps 10a-1, 10b-1, and 10c-1 of FIGS. 10A, 10B, and 10C).

2. Reaction for Oligonucleotide Attachment (a) Attachment of Oligonucleotide Using Amine-Oliginucleotide FIG. 10A shows the procedure of attachment of oligonucleotide 34 on a cleaned glass substrate 24 using amino-oligonucleotide. The cleaned glass substrate 24 is reacted with a silanazation material, for example, (10-carbomethoxydecyl)dimethylchlorosilane ($ClSi(CH_3)_2$—$(CH_2)_n$—COOH), with a carboxyl-convertible functional group.

For the reaction, the cleaned glass substrate 24 is dried in a vacuum and reacted in a solution of the silanization material of about 0.5 mL in 20 mL of toluene for about 24 hours in an argon gas atmosphere. Next, the glass substrate is washed with toluene and then acetone, and dried in a vacuum or by flowing gas. The glass substrate is socked and reacted in a 1 M HCl solution at 50° C. for 5 hours, thereby resulting in a carboxyl-substituted glass substrate (Step 10a-2). The glass substrate with the carboxyl group is washed with acetone and dried. The glass substrate is reacted in an aqueous solution of 0.2M N-hydroxysuccinimide (NHS), 0.2M 1-(3-dimethylaminopropyl)-3-ethylcarbodiimide hydrochloride (EDCl), and amine-oligonucleotide ($H_2N$-oligo) of 0.01-0.1 mg/mL for 20 hours, followed by surface washing. The result is an oligonucletide-attached glass substrate (Step 10a-3).

(b) Attachment of Oligonucleotide Using Amine-Oligo-Thiol Group

FIG. 10B shows the procedure of attachment of oligonucleotide on the cleaned glass substrate 24 using an amine-oligo-thiol group. The cleaned glass substrate 24 is reacted with a silanazation material, for example, (10-carbomethoxydecyl)dimethylchlorosilane ($ClSi(CH_3)_2$—$(CH_2)_n$—COOH), with a carboxyl-convertible functional group.

For the reaction, the cleaned glass substrate 24 is dried in a vacuum and reacted in a solution of the silanization material of about 0.5 mL in 20 mL of toluene for about 24 hours in an argon gas atmosphere. Next, the glass substrate is washed with toluene and then acetone, and dried in a vacuum or by flowing gas. The glass substrate is socked and reacted in a 1M HCl solution at 50° C. for 5 hours, thereby resulting in a carboxyl-substituted glass substrate (Step 10b-2). The glass substrate with the carboxyl group is washed with acetone and dried. The glass substrate is reacted in an aqueous solution of 0.2M NHS, 0.2M EDCl, and an amine-oligonucleotide-thiol group ($H_2N$-oligo-SH) of 0.01-0.1 mg/mL for 20 hours, followed by surface washing. The result is an oligonucletide-attached glass substrate (Step 10b-3).

(c) Attachment of Oligonucleotide Using Biotin-Avidin Reaction

FIG. 10C shows the procedure of attachment of oligonucleotide on the cleaned glass substrate 24 using biotin-avidin reaction. The cleaned glass substrate 24 is reacted with a silanazation material, for example, (10-carbomethoxydecyl)dimethylchlorosilane ($ClSi(CH_3)_2$—$(CH_2)_n$—COOH), with a carboxyl-convertible functional group.

For the reaction, the cleaned glass substrate 24 is dried in a vacuum and reacted in a solution of the silanization material of about 0.5 mL in 20 mL of toluene for about 24 hours in an argon gas atmosphere. Next, the glass substrate is washed with toluene and then acetone, and dried in a vacuum or by flowing gas. The glass substrate is socked and reacted in a 1M HCl solution at 50° C. for 5 hours, thereby resulting in a carboxyl-substituted glass substrate (Step 10c-2). The glass substrate with the carboxyl group is washed with acetone and dried. The glass substrate is reacted in an aqueous solution of 0.2M NHS, 0.2M EDCl, and avidin (denoted by reference numeral 51) of 11 mg/mL for 20 hours, followed by surface washing with buffer (10 mN Tris, pH 7.2).

Next, the glass substrate surface is reacted with a solution of biotin (denoted by reference numeral 50)-oligonucleotide in 1 XTBE for 8 hours and washed with buffer (Step 10c-4). Alternatively, the glass substrate is reacted with a solution of biotin-oligo-SH in 1 XTBE and washed with buffer (Step 10c-5).

<Synthesis of Cleavable Signal. Element and Attachment to Gold Substrate>

FIGS. 10D through 10H show alternative embodiments of the synthesis of cleavable signal elements and attachment to gold substrates.

1. Cleaning of Gold Substrate

Gold substrates are soaked in a saturated KOH solution for 1 hour and rinsed copiously with distilled water. The gold substrates are then soaked in sulfuric acid for approximately 2 hours, followed by rinsing with distilled water (Steps 10d-1, 10e-1, 10g-1, and 10h.sup.-1).

2. Reaction for Oligonucleotide Attachment (a) Attachment of Oligonucleotide Using Thiol Group FIG. 10D shows the procedure of attachment of the oligonucleotide 34 on a cleaned gold substrate 22 using a thiol group. The entire surface of the gold substrate 22 is spray-coated with a buffer solution into which HS—$(CH_2)_n$-oligo has been dissolved, tightly sealed to prevent coating evaporation, and reacted for approximately 5 hours. Following washing with buffer (Step 10d-2), a buffer solution containing HS—$(CH_2)_n$—OH is applied to the gold substrate surface to space out the oligonucleotides immobilized on the surface (Step 10d-3).

FIG. 10E shows another embodiment of the attachment of the oligonucleotide 34 on the cleaned gold substrate 22 using the thiol group. The entire surface of the gold substrate 22 is spray-coated with a buffer solution containing HS—$(CH_2)_n$—COOH, for example, HS—$(CH_2)_6$—COOH in 0.2M aqueous mercaptohexanoic acid solution, tightly sealed to prevent coating evaporation, and reacted for approximately 10 hours. Following washing with distilled water and drying (Step 10e-2), the resulting gold substrate is reacted in an aqueous solution of 0.2M NHS, 0.2M EDCl, and amine-oligonucleotide-thiol ($H_2$N-oligo-SH) of 0.01-0.1 mg/mL for 10 hours (Step 10e-3).

(b) Attachment of Oligonucleotide Using Biotin-Avidin Reaction

Figure 10F:
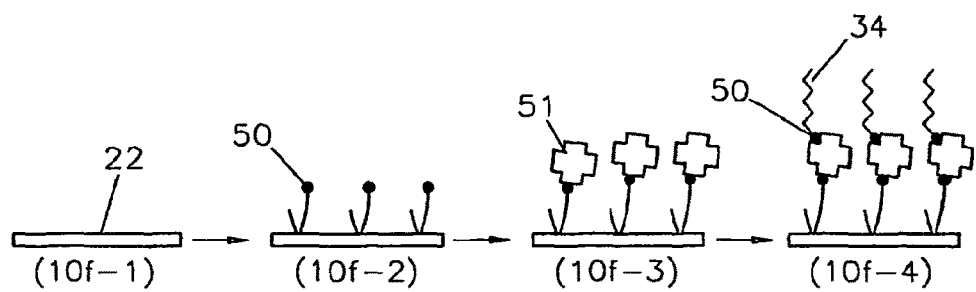

FIG. 10F shows the procedure of attachment of the oligonucleotide 34 on the cleaned gold substrate 22 using biotin-avidin reaction. The entire surface of the gold substrate 22 is coated with a solution of biotin disulfide N-hydroxysuccinimide (prepared by dissolving 1 g of biotin disulfide N-hydroxysuccinimide in 200 μL of dimethylformamide (DMF) and diluting the solution with addition of 800 μL of distilled water), tightly sealed to prevent coating evaporation, and reacted for approximately 5 hours. Following washing with distilled water (Step 10f-2), the resulting gold substrate is spray-coated with an avidin solution, tightly sealed, and reacted for 10 hours (Step 10f-3, reference numeral 51 denotes an avidin molecule. Next, the glass substrate surface is reacted with a solution of biotin (denoted by reference numeral 50)-oligonucleotide in 1 XTBE for approximately 8 hours and washed with buffer (Step 10f-4).

Figure 10G:
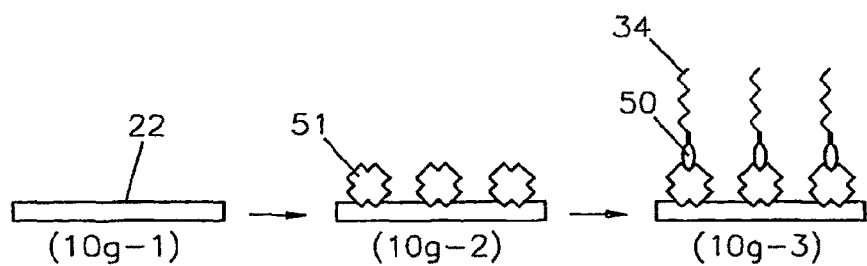

FIG. 10G shows another embodiment of the attachment of the oligonucleotide 34 on the cleaned gold substrate 22 using the biotin-avidin reaction. The surface of the gold substrate 22 is coated with a solution of avidin (denoted by reference numeral 51) in 1 XTBE, tightly sealed to prevent coating evaporation, and reacted for approximately 5 hours (Step 10g-2). Next, the glass substrate surface is reacted with a solution of biotin (denoted by reference numeral 50)-oligonucleotide in 1 XTBE for approximately 8 hours and washed with buffer (Step 10g-3).

(c) Attachment of Oligonucleotide-Biotin Using Thiol Group

Figure 10H:
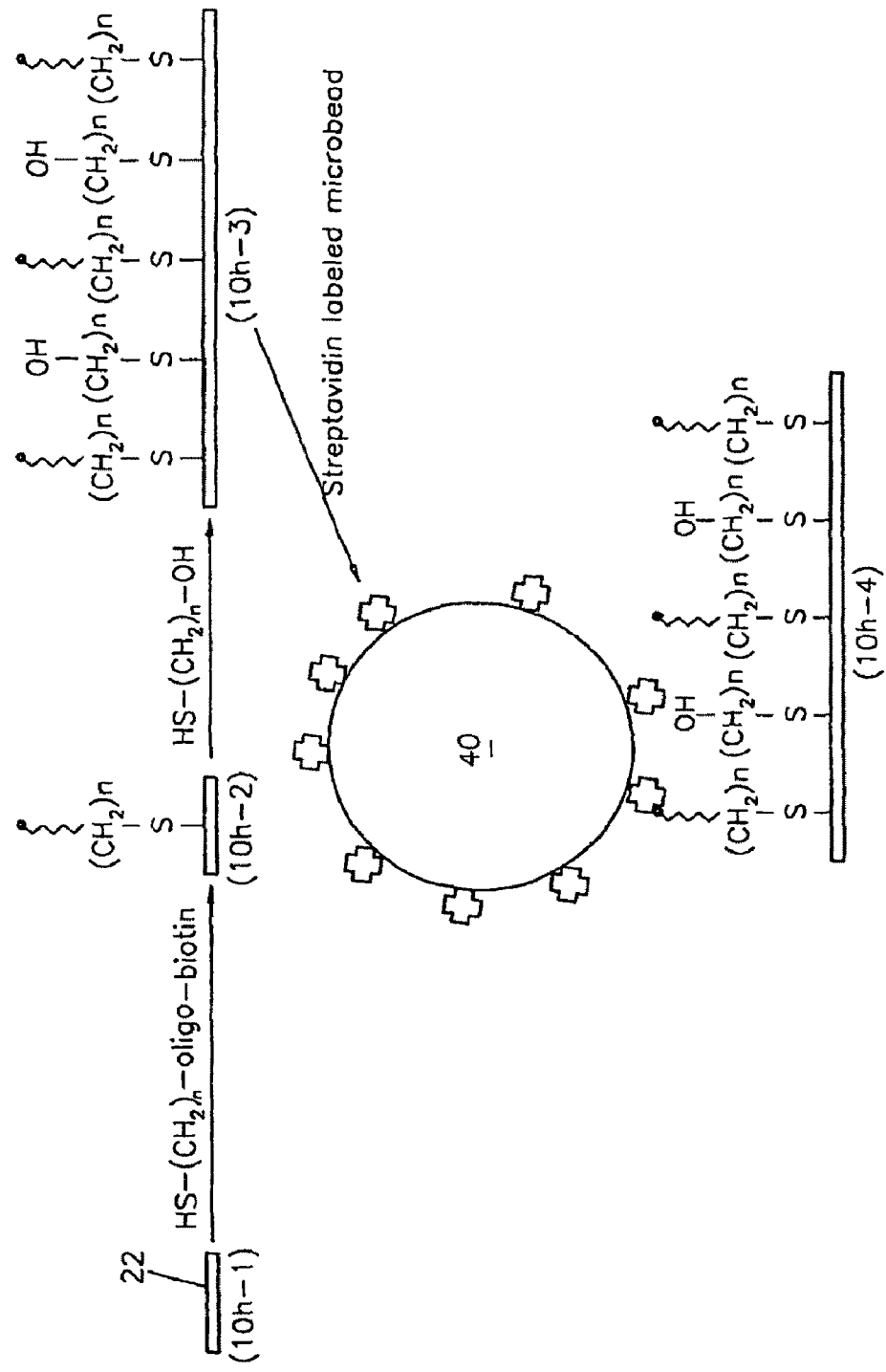

FIG. 10H shows the procedure of attachment of oligonucleotide-biotin on the cleaned gold substrate 22 using the thiol group. The entire surface of the cleaned gold substrate 22 is spray-coated with a buffer solution into which HS—$(CH_2)$.sub.n-oligo-biotin has been dissolved, tightly sealed to prevent coating evaporation, and reacted for approximately 5 hours. Following washing with buffer (Step 10h-2), a buffer solution containing HS—$(CH_2)_n$—OH is applied to the gold substrate surface to space out the oligonucleotides immobilized on the surface (Step 10h-3).

<Synthesis of Cleavable Signal Element and Attachment to Plastic Substrate>

Figure 10I:
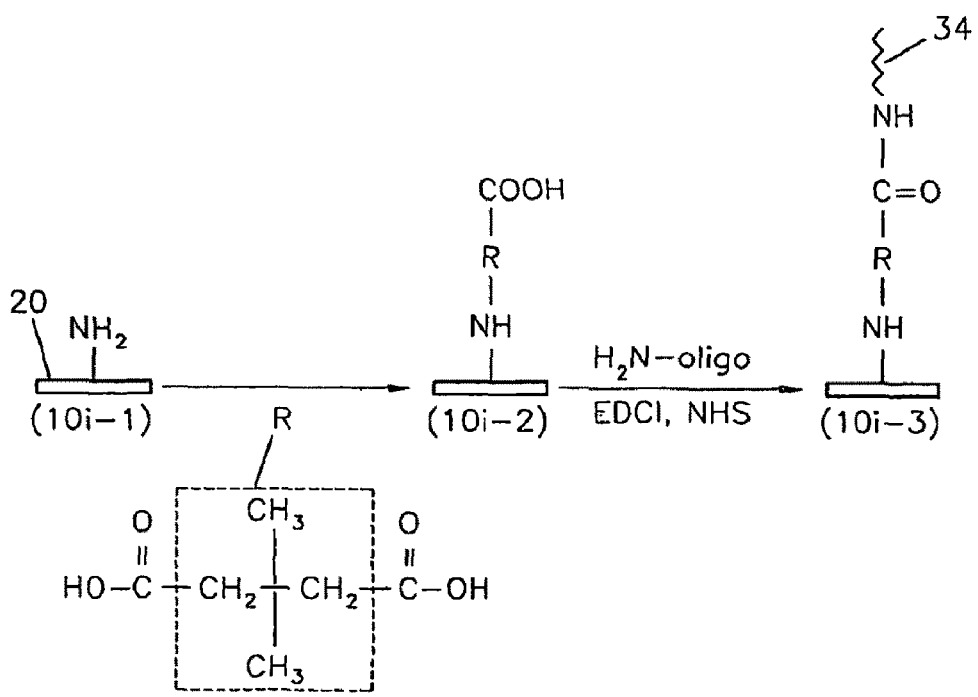
Figure 10J:
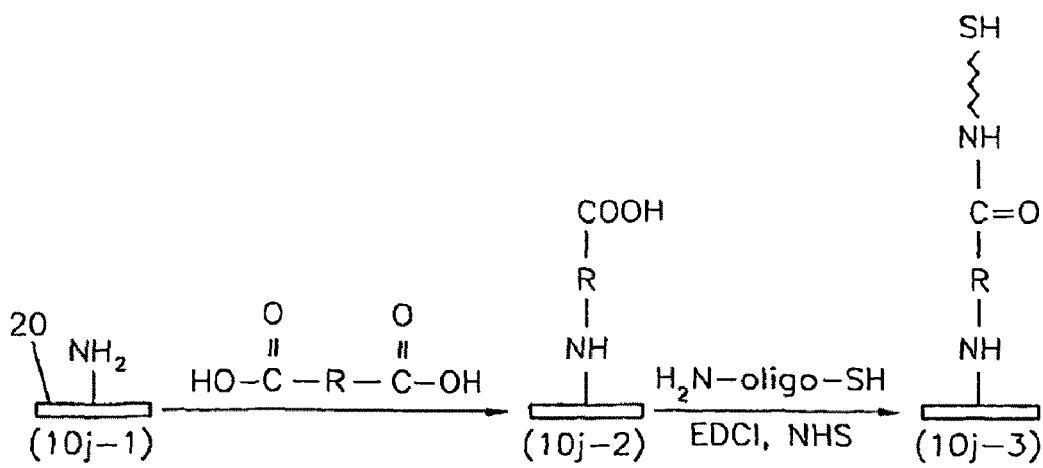
Figure 10K:
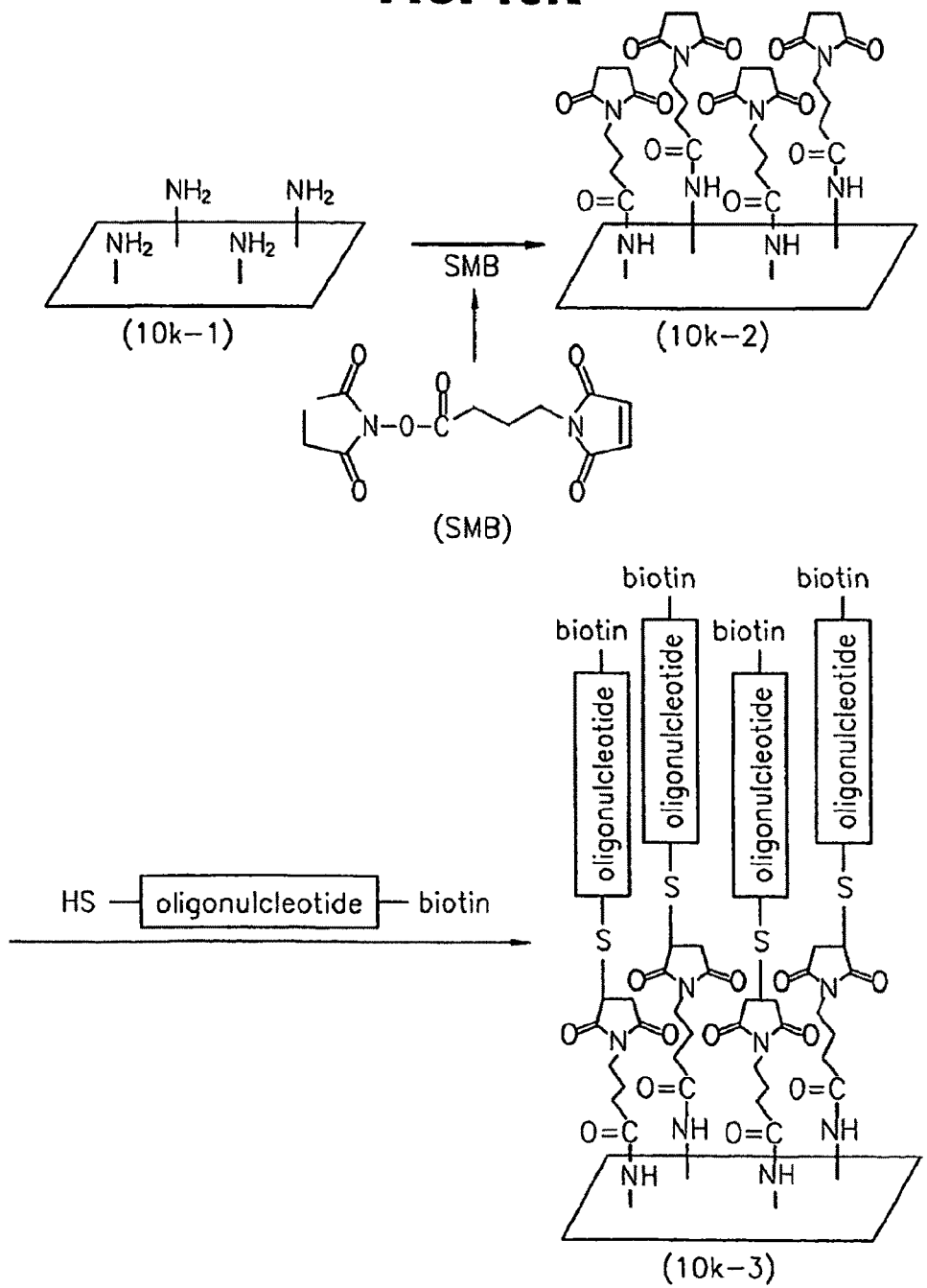

FIGS. 10I through 10K shows alternative embodiments of the synthesis of cleavable signal elements and attachment to plastic substrates.

1. Cleaning of Plastic Substrate

Gold substrates are soaked and sonicated in a Alconox solution for about 30 minutes and rinsed copiously with distilled water.

2. Reaction for Oligonucleotide Attachment

FIG. 10I shows an embodiment of the attachment of the oligonucleotides 34 on a cleaned plastic substrate 20. The surface of the plastic substrate 20 is aminated by ammonia plasma (Step 10i-1) and completely spray-coated with a buffer solution in which —COOH—R—COOH, where R is any amine-reactive formula, for example, 3,3-diimethylgutaric acid (—HOOC—$CH_2$—$C(CH_3)_2$—$CH_2$—COOH), has been dissolved (Step 10i-2). Preferably, R is alkane or other functional groups. The plastic substrate 20 is tightly sealed and reacted for approximately 10 hours. Following washing with distilled water and drying, the plastic substrate is reacted in an aqueous solution of 0.2M NHS, 0.2M EDCl, and amine-oligonucleotide ($H_2$N-oligo) of 0.01-0.1 mg/mL for 10 hours (Step 10i-3).

FIG. 10J shows another embodiment of the attachment of the oligonucleotides on the cleaned plastic substrate 20. The surface of the plastic substrate 20 is aminated by ammonia plasma (Step 10j-1) and completely spray-coated with a buffer solution in which —COOH—R—COOH has been dissolved (Step 10j-2). The plastic substrate 20 is tightly sealed and reacted for approximately 10 hours. Following washing with distilled water and drying, the plastic substrate is reacted in an aqueous solution of 0.2M NHS, 0.2M EDCl, and amine-oligonucleotide-thiol ($H_2$N-oligo-SH) of 0.01-0.1 mg/mL for 10 hours (Step 10j-3).

FIG. 10K shows still another embodiment of the attachment of the oligonucleotides to the cleaned plastic substrate 20. The surface of the plastic substrate 20 is aminated by ammonia plasma (Step 10k-1) and completely spray-coated with a solution of succinimidyl 4-maleimido butyrate (SMB), a heterobifunctional crosslinker, in a 1:10 mixture of DMF and sodium bicarbonate buffer (50 mM, pH 8.5) (Step 10k-2: monolayer formation). The resulting plastic substrate is tightly sealed and reacted for approximately 3 hours. Following washing with distilled water and drying, the plastic substrate is reacted with HS-oligonucleotide-biotin in HEPES buffer (10 mM, pH 6.6, 5.0 mM EDTA) for 3 hours (Step 10k-3).

<Method to Increase Detector Sensitivity>

In the nucleic acid hybridization assay according to the present invention, to increase the sensitivity of the detector including an optical device, an electrochemical device, a mass measurement device, or a capacitance and impedance measurement device, after Steps 10b-3, 10c-5, 10e-3, and 10j-e, or after the first wash step and cleavage, a metal microsphere suspension is spread over the substrate and reacted at room temperature for about 0.5 hours to form a metal microsphere-attached cleavable signal element or a "label-attached uncleaved probe" structure.

In the nucleic acid hybridization assay according to the present invention, to increase the sensitivity of the detector including an optical device, an electrochemical device, a mass measurement device, or a capacitance and impedance measurement device, alternatively, after Steps 10a-3, 10c-4, 10*d*-3, 10*f*-4, 10*g*-4, and 10*i*-3, or after the first wash step and cleavage, a conducting polymer solution is spread over the substrate and reacted at room temperature for about 5 hours to form a conducting polymer-attached cleavable signal element or a "label-attached uncleaved probe" structure.

In the nucleic acid hybridization assay method according to the present invention, to increase the sensitivity of the detector including an optical device, an electrochemical device, a mass measurement device, or a capacitance and impedance measurement device, alternatively, after Steps 10*a*-3, 10*c*-4, 10*d*-3, 10*f*-4, 10*g*-4, and 10*i*-3, or after the first wash step and cleavage, an aqueous solution of fluorecein isothiocyanate of 0.1 mg/mL, a fluorescer, is spread over the substrate and left in a dark room for about 5 hours to form a fluorescent-labeled cleavable signal element or a "label-attached uncleaved probe" structure.

For label attachment, the amine group of the oligonucleotides should extend towards the reaction solution.

In the nucleic acid hybridization assay method according to the present invention, to increase the sensitivity of the detector including an optical device, an electrochemical device, a mass measurement device, or a capacitance and impedance measurement device, alternatively, after Steps 10*h*4 and 10*k*-3 or after the first wash step and cleavage, a suspension of streptavidin labeled microbeads 40 or streptavidin-labeled magnetic microbeads is spread over the substrate and reacted at room temperature for about 5 hours to form a streptavidin-labeled microbead-attached (or magnetic microbead attached) cleavable signal element" or a "label-attached uncleaved probe" structure.

<Gold Particles as Signal Responsive Moieties>

In preferred embodiments of the present invention, particles that reflect or scatter light are used as signal responsive moieties. A light reflecting and/or scattering particle is a molecule or a material that causes incident light to be reflected or scattered without absorbing the light energy. Such light reflecting and/or scattering particles include, for example, metal particles, colloidal metal such as colloidal gold, colloidal non-metal labels such as colloidal selenium, dyed plastic particles made of latex, polystyrene, polymethylacrylate, polycarbonate or similar materials.

The size of such particles ranges from 1 nm to 10 μm, preferably from 500 nm to 5 μm, and most preferably from 1 to 3.mu.m. The larger the particle, the greater the light scattering effect. Metal microspheres 1 nm to 10 μm in diameter, preferably 0.5-5 μm, most preferably 1-3 μm in diameter, are presently preferred in the light reflecting/light scattering embodiment of the present invention. Metal microspheres provide a convenient signal responsive moiety for detection of the presence of an uncleaved signal element bound to the disk. Typical materials are gold, silver, nickel, chromium, platinum, copper, and the like, or alloys thereof, with gold being most preferred. The metal microspheres may be solid metal or may be formed of plastic, or glass beads or the like, upon which a coating of metal has been deposited. Metal microspheres may also be alloys.

Gold spheres suitable for use in the cleavable reflective signal element and assay device of the present invention are readily available in varying diameters from Aldrich Chemical Company, British BioCell International, Nanoprobes, Inc., and others, ranging from 1 nm to and including 0.5 μm (500 nm)-5 μm in diameter. It is within the skill in the art to create gold microspheres of lesser or greater diameter as needed in the present invention. Much smaller spheres can be used advantageously when reading is performed with optical microscopy, UV-light, electron beam or scanning probe microscopy. Smaller spheres are preferred because more cleavable signal elements can be discriminated in a given area of a substrate.

Although spherical particles are preferred, non-spherical particles are also useful for some embodiments. In biological applications, the signal responsive moiety—particularly gold or latex microspheres—will preferably be coated with detergents or derivatized so that they have a surface charge. This is done to prevent the attachment of these particles nonspecifically with surfaces or with each other.

The preferred gold microspheres bind directly to the thiol group of the end of the cleavable signal element, yielding a very strong bond.

Furthermore, while the above embodiments of the invention have been described with a single metal microsphere attached to the end of a single cleavable signal element, it should be appreciated that when gold is used in a preferred embodiment of the invention, thousands of cleavable signal elements may bind one gold microsphere, depending upon its diameter. It is estimated that one sphere of 1-3 μm may be bound by approximately 1,000-10,000 cleavable signal elements.

As a result, the stringency of the assay wash may be adjusted to give higher assay reliability, at any given rotational speed, by varying not only the diameter of the gold sphere, but also the relative density of cleavable signal elements to gold microspheres.

Accordingly, if virtually all captures probes under a certain gold microsphere are connected by complementary molecules, the binding is very strong. If the capture probes are fixated only partially under a certain gold microsphere, the microsphere may remain or be removed depending on the radius of the microsphere and the frequency of the rotation.

In another preferred embodiment of the present invention, since the metal microsphere increases conductivity, it can improve the sensitivity of a detector constructed of the capacitance and impedance measurement device.

In still another preferred embodiment of the present invention, conducting polymers or fluorescent labels may be used instead of the metal microsphere. The conducting polymer or fluorescent label acts as a light reflecting (light diverging) and scattering particle or a conductivity-increasing particle, so it can improve detection sensitivity when used with a photodetector (fluorescent detector) or a detector constructed of the capacitance and impedance measurement device.

<Other Light-Responsive Signal Responsive Moieties>

In other embodiments of the cleavable signal element and assay device of the present invention, a light-absorbing rather than light-reflective material can be used as a signal responsive moiety. The approach is analogous to that used in recordable compact disks.

Although similar in concept and compatible with CD readers, information is recorded differently in a recordable compact disk (CD-R) as compared to the encoding of information in a standard CD. In CD-R, the data layer is separate from the polycarbonate substrate. The polycarbonate substrate instead has impressed upon it a continuous spiral groove as a reference alignment guide for the incident laser. An organic dye is used to form the data layer. Although cyanine was the first organic dye used for these disks, a metal-stabilized cyanine compound is generally used instead of "raw" cyanine. An alternative material is phthalocyanine. One such metallophthalocyanine compound is described in U.S. Pat. No. 5,580,696.

In CD-R, the organic dye layer is sandwiched between the polycarbonate substrate and the metalized reflective layer, usually 24 carat gold, but alternatively silver, of the media.

Information is recorded by a recording laser of appropriate preselected wavelength that selectively melts "pits" into the dye layer, it simply melts it slightly, causing it to become non-translucent so that the reading laser beam is refracted rather than reflected back to the reader's sensors. As in a standard CD, a lacquer coating protects the information layers.

A greater number of light-absorbing dyes may be used in this embodiment of the present invention than may be used in CD-R. Light-absorbing dyes are any compounds that absorb energy from the electromagnetic spectrum, ideally at wavelength(s) that correspond to the wavelength(s) of the light source. As is known in the art, dyes generally consist of conjugated heterocyclic structures, exemplified by the following classes of dyes: azo dyes, diazo dyes, triazine dyes, food colorings or biological stains. Specific dyes include: Coomasie Brilliant Blue R-250 Dye (Biorad Labs, Richmond, Calif.); Reactive Red 2 (Sigma Chemical Company, St. Lois, Mo.), bromophenol blue (Sigma); xylene cyanol (Sigma); and phenolphthalein (Sigma). The Sigma-Aldrich Handbook of Stains, Dyes and Indicators by Floyd J. Green, published by Aldrich Chemical Company, Inc., (Milwaukee, Wis.) provides a wealth of data for other dyes. With these data, dyes with the appropriate light absorption properties can be selected to coincide with the wavelengths emitted by the light source.

In other embodiments, the signal responsive moiety may be a fluorescer, such as fluorescein, propidium iodide or phycoerythrin, or a chemiluminescer, such as luciferin, which responds to incident light, or an indicator enzyme that cleaves soluble fluorescent substrates into insoluble form. Other fluorescent dyes useful in this embodiment include texas red, rhodamine, green fluorescent protein, and the like. Fluorescent dyes will prove particularly useful when blue lasers become widely available.

The present invention preferentially employs a circular assay device as the substrate for the patterned deposition of light-reflective, light-scattering, light-absorptive, or fluorescent cleavable signal elements. In a preferred embodiment, the assay device is compatible with existing optical disk readers, such as a compact disk (CD) reader or a digital versatile disk (DVD) reader, and is therefore preferentially a disk of about 120 mm in diameter and about 1.2 mm in thickness. It will be appreciated, however, that the cleavable signal elements of the present invention may be deposited in spatially-addressable patterns on substrates that are not circular but rectangular.

The maximum number of cleavable signal elements that can be spatially discriminated on an optical disk is a function of the wavelength and the numerical aperture of the objective lens. One known way to increase memory capacity in all sorts of optical memory disk, such as CD-ROMs, WORM (Write Once Read Many) disks, and magneto-optical disks, is to decrease the wavelength of the light emitted by the diode laser which illuminates the data tracks of the optical memory disks. Smaller wavelength permits discrimination of smaller data spots on the disk, that is, higher resolution, and thus enhanced data densities. Current CD-ROMs employ a laser with a wavelength of 780 nanometers (nm). Current DVD readers employ a laser with a wavelength between 635 and 650 nm. New diode lasers which emit, for example, blue light (around 481 nm) would increase the number of signal elements that could be spatially addressed on a single assay device disk of the present invention. Another way to achieve blue radiation is use of a second harmonic generator (SHG) that achieves frequency doubling of infrared laser by non-linear optical material.

Current CD-ROM readers employ both reflection reading and transmission reading. Both data access methods are compatible with the present invention. Gold particles are especially suitable for use as a signal responsive moiety for reflection type CD-ROM readers. Light-absorbing dyes are more suitable for transmission type readers such as the ones discussed in U.S. Pat. No. 4,037,257.

<Other Signal Responsive Moieties>

It will be apparent to those skilled in the art that signal responsive moieties suitable for adaptation to the cleavable signal element of the present invention are not limited to light-reflecting or light-absorbing metal particles or dyes. Suitable signal responsive moieties include, but are not limited to, any composition detectable by spectroscopic, photochemical, biochemical, immunochemical, electrical, optical or chemical means. In preferred embodiments, suitable signal responsive moieties include calorimetric labels such as colloidal gold or colored glass or plastic (e.g., polystyrene, polypropylene, latex, etc.) beads, biotin-bound beads with labeled streptavidin conjugate, magnetic beads (e.g., DynabeadS™), radiolabels (e.g., $^{3}H$, $^{125}I$, $^{35}S$, $^{14}C$, or $^{32}P$), and enzymes (e.g., horse radish peroxidase (HRP), alkaline phosphatase, etc.).

It will be apparent to those skilled in the art that numerous variations of signal responsive moieties may be adapted to the cleavable signal elements of the present invention. A number of patents, for example, provide an extensive teaching of a variety of techniques for producing detectable signals in biological assays. Such signal responsive moieties are generally suitable for use in some embodiments of the present invention. As a non-limiting illustration, the following is a list of U.S. patents teach the several signal responsive moieties suitable for embodiments of the present invention: U.S. Pat. No. 3,646,346, radioactive signal generating means; U.S. Pat. Nos. 3,654,090, 3,791,932 and 3,817,838, enzyme-linked signal generating means; U.S. Pat. No. 3,996,345, fluorescer-quencher related signal generating means; U.S. Pat. No. 4,062,733, fluorescer or enzyme signal generating means; U.S. Pat. No. 4,104,029, chemiluminescent signal generating means; U.S. Pat. No. 4,160,645, non-enzymatic catalyst generating means; U.S. Pat. No. 4,233,402, enzyme pair signal generating means; U.S. Pat. No. 4,287,300, enzyme anionic charge label. All above-cited U.S. patents are incorporated herein by reference for all purposes.

Other signal generating means are also known in the art, for example, U.S. Pat. Nos. 5,021,236 and 4,472,509, both incorporated herein by reference for all purposes. A metal chelate complex may be employed to attach signal generating means to the cleavable signal elements. In other embodiments, magnetic spheres may be used in place of reflective spheres, and magnetic poles may be vertically aligned by treating the disk with a magnetic field that is of sufficient strength. Since the empty sites will not have any magnetic material present, the presence or absence of a target nucleic acid in the test sample can be identified. The location of the uncleaved signal element can be detected using an optomagnetic sensor widely used in existing optomagnetic disks based on the Kerr effect or a magneto resistance (MR) sensor.

Paramagnetic ions might be used as a signal generating means, for example, ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III), with gadolinium being particularly preferred. Ions useful in other contexts, such as X-ray imaging, include but are not limited to lanthanum (III), gold (III), lead (II), and especially bismuth (III).

Means of detecting such labels are well known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and calorimetric labels are detected by simply visualizing the colored label. Colloidal gold label can be detected by measuring scattered light. A preferred non-reflective signal generating means is biotin, which may be detected using an avidin or streptavidin compound. The use of such labels is well known to those of skill in the art and is described, for example, in U.S. Pat. Nos. 3,817,837; 3,850,752; 3,939,350; 3,996,345; 4,277,437; 4,275,149 and 4,366,241; each incorporated herein by reference for all purposes.

<Patterned Deposition of Cleavable Signal Elements on Plastic Substrate>

A photoresist may also profitably be used to pattern the deposition of cleavable signal elements. The resist is partially depolymerized by incident laser light during fabrication and can be dissolved from these areas. The exposed or metalized portion of the plastic substrate is treated chemically, for example, aminated by ammonia plasma. After the resist is removed, the cleavable signal elements are attached to the substrate. The use of photoresists for the patterning of master disks is well known in the compact disk fabrication arts.

Alternatively, instead of using a resist, a solid mask containing small holes can be used during ammonia plasma treatment. Holes have a diameter of about 1 to 3 micrometers. The holes are located circularly in the mask, forming a spiral track or a pattern that is a combination of spiral and circular paths. The mask can be metal or plastic. Several metals, such as aluminum, nickel or gold can be used. Polycarbonate is a preferred plastic, because it will retain shape well. Plastics are reactive with the ammonia plasma, however, and a preferred method for using plastic masks therefore involves depositing a metal layer on the plastic, by evaporation, sputtering, or other methods known in the art. Holes may be made in the mask by laser. Those with skill in the art will appreciate that it is possible to create 1000 1.mu.-sized holes in one second in a thin metal or plastic plate. Alternatively, the holes can be etched by using conventional methods known in the semiconductor industry. In the mask approach to patterning the deposition of cleavable signal elements, the mask is pressed against the substrate and subjected to amination by ammonia plasma. The mask may be used repeatedly.

<SNP Detection in Nucleic Acid Hybridization Assay Using Cleavable Signal Element>

In a nucleic acid hybridization assay according to the present invention, the capture probe of the cleavable signal element is oligonucleotides designed to hybridized to a complementary sequence of a target nucleic acid to be detected in the sample. For many applications of this methodology, cross-reactivity with sample oligonucleotides having even a single mismatched nucleotide should be minimized. In particular, nucleic acid hybridization assays adapted to use the cleavable signal element of the present invention for detection of point mutations, as, e.g., for detection of point mutations in the BRCA1 and BRCA2 genes that predispose to breast and ovarian cancers, must be able to discriminate between nucleic acid samples containing a single mismatched nucleotide, i.e., must be able to detect SNP.

The longer the oligonucleotides of the capture probe—and thus the longer the sequence that is complementary between the oligonucleotides and the nucleic acid sample—the greater the possibility of erroneously recognizing a mismatched sample, since the strength of hybridization, even given the presence of a mismatch, will be reasonably high.

Thus, one way to reduce erroneous recognition of mismatched nucleic acid sequences is to reduce the length of the oligonucleotides. Specificity is increased by shortening the length of the oligonucleotides to 15-20-mers. In this case, the mismatched oligonucleotides would use fewer nucleotides for pairing and will form highly unstable binding at room temperature. This unstable binding is denatured during the first wash step and removed. However, multiple SNP detections at a plurality of assay sites are required for diagnosing a certain disease.

Figure 11A:
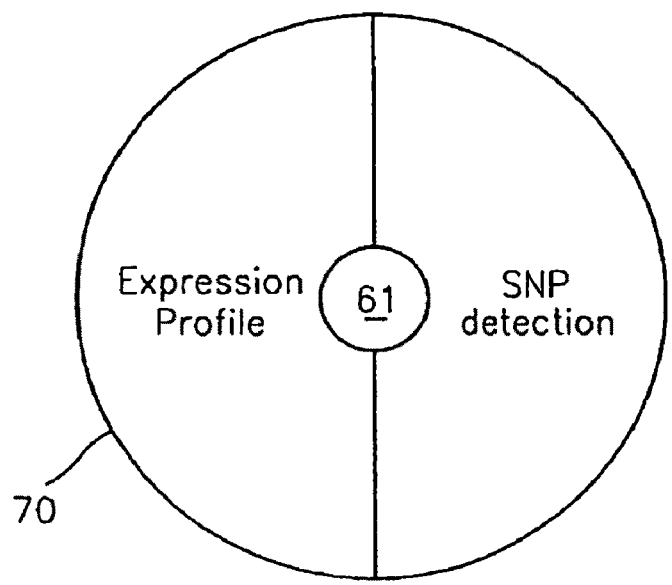
FIGS. 11A and 11B show alternative embodiments of an assay device using the cleavable signal element according to the present invention for diagnosing a variety of diseases through both single nucleotide polymorphism (SNP) detection and gene expression profile determination.
Figure 11B:
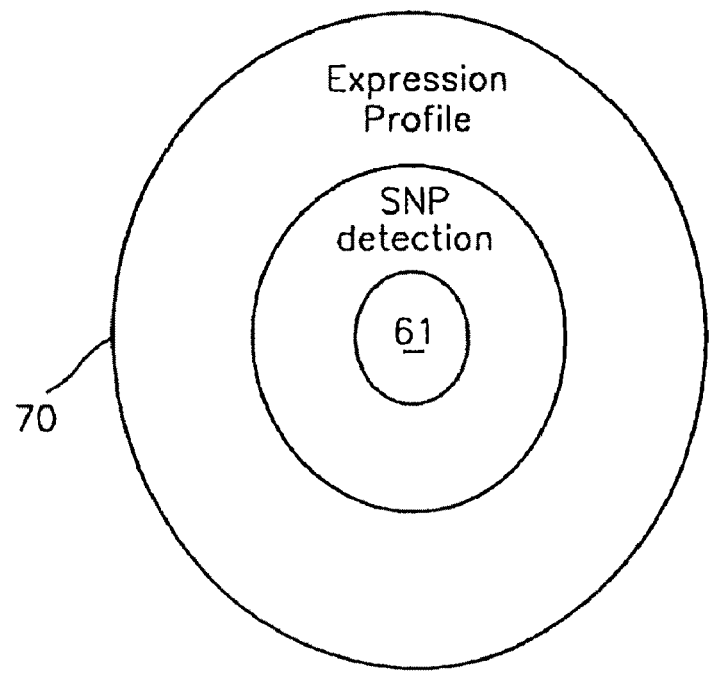

FIGS. 11A through 11B show alternative embodiments of an assay device using the cleavable signal element according to the present invention capable of both single nucleotide polymorphism (SNP) detection and gene expression profile determination for diagnosis. Reference numeral 61 denotes a center void of the substrate (disk) 70. An assay sector with shorter capture probes for SNP detection and an assay sector with longer capture probes (cDNA) for gene expression profile analysis are arranged separate on the substrate 70. The assay devices shown in FIGS. 11A through 11B can be modified in a variety of ways and forms according to the arrangements shown in FIGS. 3A through 3D, to concurrently measure SNP and expression profile.

FIG. 11A shows that the assay sectors for SNP detection and expression profile analysis are arranged separate in an angular direction. FIG. 11B shows that the assay sectors for SNP detection and expression profile analysis are arranged separate in a radial direction. The concurrent determination of the DNP and expression profile doubles diagnostic reliability and reduces assay sites by appropriate combination of assay sites.

BEST MODE FOR CARRYING OUT THE INVENTION

The present invention will be described in greater detail with reference to the following examples. The following examples are for illustrative purposes and are not intended to limit the scope of the invention.

Example 1

Detection of HIV-1

HIV-1 proviral DNA from clinical samples is amplified as follows, essentially as described in U.S. Pat. No. 5,599,662, incorporated herein by reference.

Peripheral blood monocytes are isolated by standard Ficoll-Hypaque density gradient methods. Following isolation of the cells, the DNA is extracted as described in Butcher and Spadoro, *Clin. Immunol.* Newsletter 12:73-76 (1992), incorporated herein by reference. Polymerase chain reaction (PCR) is performed in a 100 µL reaction volume, of which 50 µL is contributed by the sample. The PCR contained the following reagents at the following initial concentrations:
0.10 mM Tris-HCI (pH 8.4)
50 mM KCI
200 µM each dATP, dCTP, dGTP, and dUTP
25 pmoles of Primer 1 (sequence: 5'-TGA GAC ACC AGG AAT TAG ATA TCA GTA CAA TGT-3') (SEQ ID NO: 1)
25 pmoles of Primer 2 (sequence: 5'-CTA AAT CAG ATC CTA CAT ATA AGT CAT CCA TGT-3') (SEQ ID NO: 2) 3.0 mM MgC$_2$
10% glycerol 2.0 units of Taq DNA polymerase (Perkin-Elmer)
2.0 units UNG (Perkin-Elmer)

Amplification is carried out in a TC9600 DNA Thermal Cycler (Perkin Elmer, Norwal, Conn.) using the following temperature profile: (1) pre-incubation—50° C. for 2 minutes; (2) initial cycle—denature at 94° C. for 30 seconds, anneal at 50° C. 30 seconds, extend at 72° C. for 30 seconds; (3) cycles 2 to 4—denature at 94° C. for 30 seconds, anneal for 30 seconds, extend at 72° C. for 30 seconds, with the annealing temperature increasing in 2° C. increments (from 52° C. to 58 C); (4) cycles 5 to 39—denature at 90° C. for 30 seconds, anneal at 60° C. for 30 seconds, extend at 72° C. for 30 seconds.

Following the temperature cycling, the reaction mixture is heated to 90° C. for 2 minutes and diluted to 1 mL. Alternatively, the sample is stored at −20° C., and after thawing, heated to 90° C. for 2 minutes then diluted to 1 mL.

The cleavable signal elements are attached in a uniform density to a derivatized 120-mm polycarbonate disk substrate, as described above.

```
First capture probe
5'-TAG ATA TCA GTA CAA-3' (SEQ ID NO: 3) portion:

Second capture probe
5'-TAT TCA GTA GGT ACA-3' (SEQ ID NO: 4) portion:

First restriction probe
5'-CCCGGG-3' portion:

Second restriction probe
5'-CCCGGG-3' portion:
```

A suspension of gold microspheres, 1-3 μm in diameter, is added dropwise to the disk, which is gently rotated to distribute the gold particles. Gold particles are added until the cleavable signal elements are saturated with the gold particles. Cleavable signal elements labeled with the gold particles at its end are attached in a uniform density to a derivatized 120-mm polycarbonate disk substrate, as described above.

Sample is applied at room temperature dropwise near the center of the stationary assay device, and the assay device is rotated. Rotation is halted after the sample reaches the outer edge of the disk, and the disk is incubated in a stationary state at room temperature for 3-5 minutes (Hybridization reaction).

One mL of buffer is added dropwise as a washing solution while the disk is rotated, to distribute the buffer by disk rotation. The disk was incubated in a stationary state for 1-2 minutes, then 5 ml of buffer is added dropwise during vigorous rotation of the disk to wash the disk, with or without the application of an external electric field vertically through the disk (First Wash Step).

About 0.1 L of a DNA polymerase solution (e.g., PCR Core Systems I, Promega Corporation) containing a mixed solution of the four dNTPs listed above and a DNA polymerase is added dropwise while the disk is rotated, to distribute the DNA polymerase solution. The disk is incubated in a stationary state for 1-2 minutes (DNA extension).

A restriction enzyme solution (e.g., sma 1, Promega Corporation) that recognizes the sequence CCCGGG of the restriction probe is added dropwise and distributed by disk rotation. The restriction enzyme cleaves between C and G of the restriction probe sequence. The disk is incubated in a stationary state for 1-2 minutes (Cleavage Step).

Five mL of buffer was added dropwise during vigorous rotation of the disk with or without the application of an external electric field (Second Wash Step). An appropriate restriction solution has a reaction temperature of 37° C. and to contain 10 mM Tris-HCl (pH7.4), 300 mM KCl, 0.1 mM EDTA (Ethylene Diamine Tetra Acetic acid), 1 mM DTT (DiThioTreitol), 0.5 mg/mL BSA (Bovine Serum Albumine), and 50% glycerol.

The disk is dried, then read directly in a detector programmed to assay each predetermined site upon which cleavable signal elements are deposited, which includes an optical device, an electrochemical device, a mass measurement device, or a capacitance and impedance measurement device.

The diagnostic data and a prescription are displayed on a computer monitor, the computer automatically or manually accesses the Internet to transmit the diagnostic data to a specialist at a remote location through the Internet. The patient waits for a prescription from the specialist.

Example 2

Detection of HIV-1

HIV-1 proviral DNA from clinical samples is amplified as follows, essentially as described in U.S. Pat. No. 5,599,662, incorporated herein by reference.

Peripheral blood monocytes is isolated by standard Ficoll-Hypaque density gradient methods. Following isolation of the cells, the DNA is extracted as described in Butcher and Spadoro, *Clin. Immunol.* Newsletter 12:73-76 (1992), incorporated herein by reference. PCR was performed in a 100 μL reaction volume, of which 50 μL is contributed by the sample. The PCR contains the following reagents at the following initial concentrations:
10 mM Tris-HCl (pH 8.4)
50 mM KCl
200 μM each dATP, dCTP, dGTP, and dUTP
25 pmoles of Primer 1 (sequence: 5'-TGA GAC ACC AGG AAT TAG ATA TCA GTA CAA TGT-3') (SEQ ID NO: 1)
25 pmoles of Primer 2 (sequence: 5'-CTA AAT CAG ATC CTA CAT ATA AGT CAT CCA TGT-3') (SEQ ID NO: 2) 3.0 mM MgC$_2$
10% glycerol
2.0 units of Taq DNA polymerase (Perkin-Elmer)
2.0 units UNG (Perkin-Elmer)

Amplification is carried out in a TC9600 DNA Thermal Cycler (Perkin Elmer, Norwal, Conn.) using the following temperature profile: (1) pre-incubation—50° C. for 2 minutes; (2) initial cycle—denature at 94° C. for 30 seconds, anneal at 50° C. 30 seconds, extend at 72° C. for 30 seconds; (3) cycles 2 to 4—denature at 94° C. for 30 seconds, anneal for 30 seconds, extend at 72° C. for 30 seconds, with the annealing temperature increasing in 2° C. increments (from 52° C. to 58 C); (4) cycles 5 to 39—denature at 90° C. for 30 seconds, anneal at 60° C. for 30 seconds, extend at 72° C. for 30 seconds.

Following the temperature cycling, the reaction mixture is heated to 90° C. for 2 minutes and diluted to 1 mL. Alternatively, the sample is stored at −20° C., and after thawing, heated to 90° C. for 2 minutes then diluted to 1 mL.

Following cleaning a polycarbonate disk substrate, the surface of the disk substrate is aminated by ammonia plasma and completely spray-coated with a solution of succinimidyl 4-maleimido butyrate (SMB), a heterobifunctional crosslinker, in a 1:10 mixture of DMF and sodium bicarbonate buffer (50 mM, pH 8.5). The resulting polycarbonate substrate is tightly sealed and reacted for approximately 3 hours. Following washing with distilled water and drying, a HEPES buffer (10 mM, pH 6.6, 5.0 mM EDTA) containing HS-oligonucleotide-biotin is applied to the derivatized surface of the polycarbonate substrate to attach the HS-oligonucleotide-biotin in a uniform density, thereby constructing an assay device. The cleavable signal elements attached have the following sequences:

First capture probe
5'-TAG ATA TCA GTA CAA-3' (SEQ ID NO: 3)
(oligonucleotide) portion:

Second capture probe
5'-TAT TCA GTA GGT ACA-3' (SEQ ID NO: 4) Portion:

Sample is applied dropwise near the center of the stationary assay device, and the assay device is rotated. Rotation is halted after the sample reaches the outer edge of the disk, and the disk is incubated in a stationary state at room temperature for 3-5 minutes (Hybridization reaction).

One mL of buffer is added dropwise as a washing solution while the disk is rotated, to distribute the buffer by disk rotation. The disk is incubated in a stationary state for 1-2 minutes, then 5 ml of buffer is added dropwise during vigorous rotation of the disk to wash the disk, with or without the application of an external electric field vertically through the disk (First Wash Step).

A DNAse or nuclease solution is added dropwise and distributed by disk rotation. The disk is incubated in a stationary state for 1-2 minutes (Cleavage Step).

Following buffer addition, disk rotation, and a simple washing with the application of an external field, a suspension of streptavidin-labeled gold microspheres is added dropwise to the disk surface, and the disk is gently rotated to evenly distribute the gold particles (label-attached uncleaved probe structure formation), thereby resulting in a biotin-avidin binding structure. Next, distilled water is added dropwise during vigorous rotation of the disk to wash the disk, with or without the application of an external electric field (Second Wash Step).

The disk is dried, then read directly in a detector programmed to assay each predetermined site upon which cleavable signal elements are deposited, which includes an optical device, an electrochemical device, a mass measurement device, or a capacitance and impedance measurement device.

The diagnostic data and a prescription are displayed on a computer monitor, the computer automatically or manually accesses the Internet to transmit the diagnostic data to a specialist at a remote location through the Internet. The patient waits for a prescription from the specialist.

Experimental Example 1

Optical Measurement

Following the hybridization reaction, first wash step, cleavage step, and second wash step according to Example 2, whether hybridization to a target nucleic acid had occurred or not was determined by atomic force microscopy (AFM). As a result, the topography images by AFM are shown in FIGS. 13A and 13B.

Figure 13A:
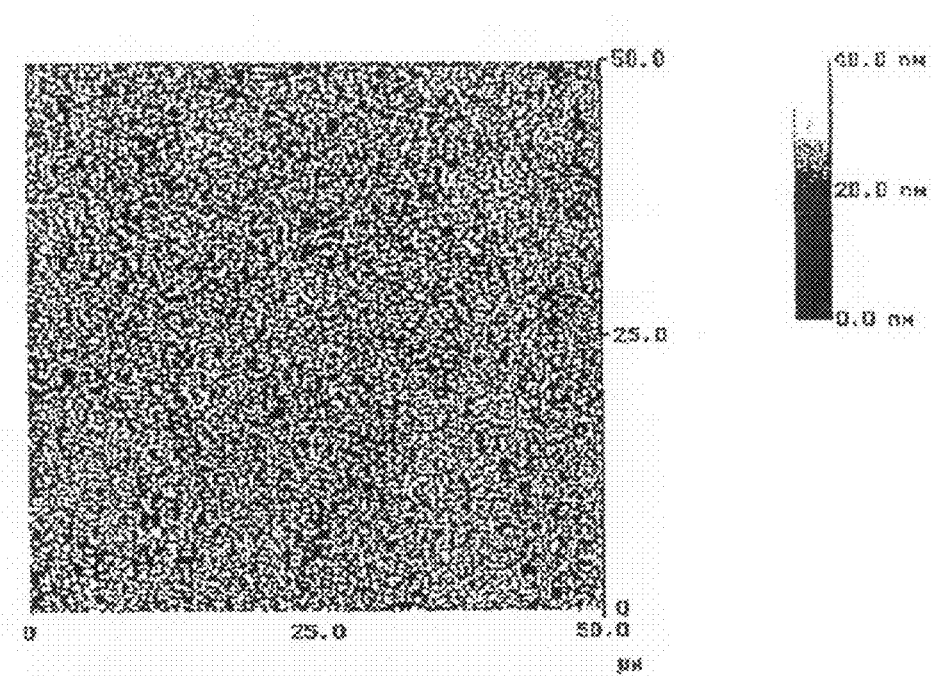
FIGS. 13A and 13B are photographs showing the results of an analysis in Example 2 optically measured by atomic force microscopy (AFM)

FIG. 13A is a topography image taken after hybridization of biotin-attached cleavable signal elements to an oligonucleotide sample of a complementary sequence, in which after the hybridization, the substrate was reacted with a mung bean-derived nuclease, washed, and additionally labeled with streptavidin-coated 40-nm metal microspheres. Since the cleavable signal elements are double-stranded, the cleavable signal elements are not cleaved by the nuclease, and the biotin-attached cleavable signal elements remain on the substrate and form a "label-attached uncleaved probe" structure by additionally contacting the streptoavidin-coated metal microspheres, thereby increasing optical selectivity. Due to the streptoavidin-to-biotin coupling, the sensitivity of the detector is increased.

Figure 13B:
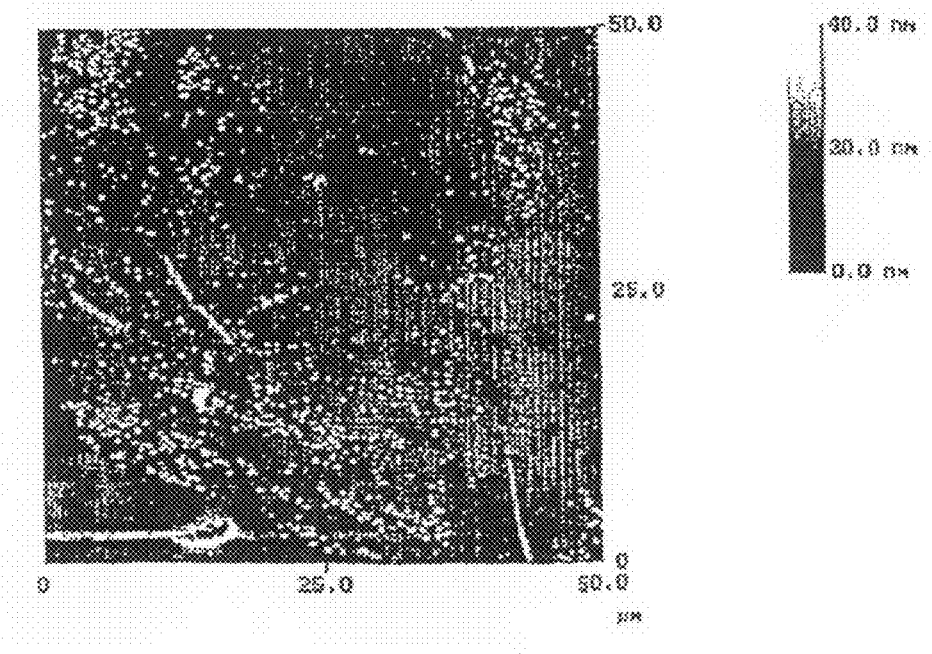

FIG. 13B is a topography image taken after reacting the biotin-attached cleavable signal elements with an oligonucleotide sample of a non-complementary sequence, in which after the reaction, the substrate was reacted with a mung bean-derived nuclease, washed, and additionally labeled with streptavidin-coated 40-nm metal microspheres. Since the cleavable signal elements remain as single strands, the cleavable signal elements are cleaved by the nuclease, and the biotin-attached cleavable signal elements are removed from the substrate. As a result, even after additionally contacting the streptoavidin-coated metal microspheres, the cleavable signal elements do not form a "label-attached uncleaved probe" structure.

Apparently, the substrate is mostly covered with the metal microspheres in FIG. 13A, whereas few metal microspheres are shown in FIG. 13B. Differential signals from the metal microspheres are provided to the detector.

Experimental Example 2

Impedance Measurement

Figure 14:
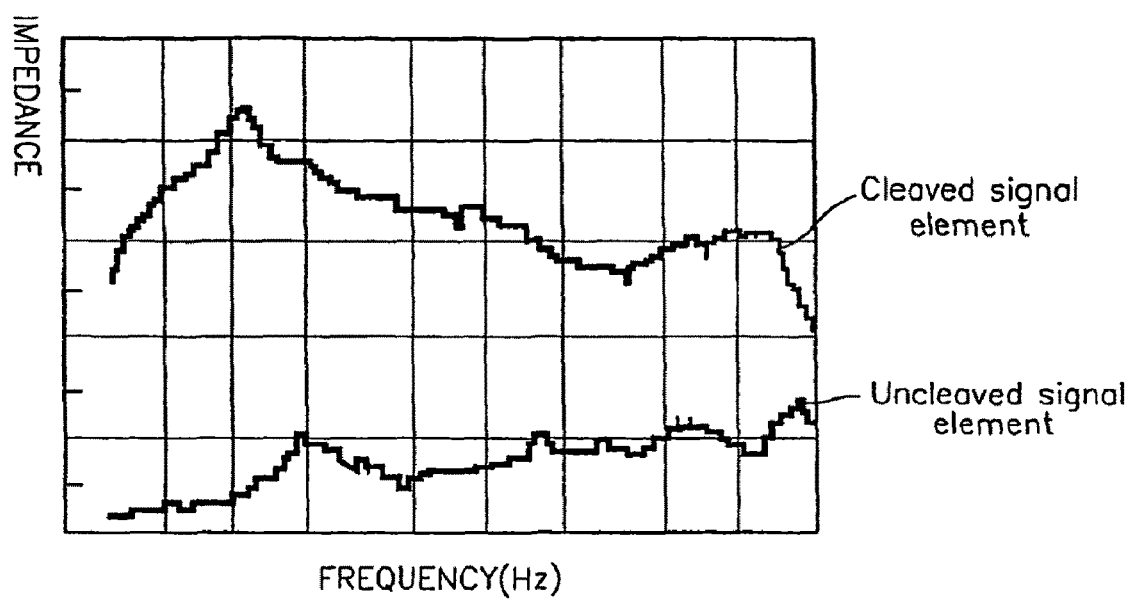
FIG. 14 is a graph of the impedance measured in Example 2.

Following the hybridization reaction, first wash step, cleavage step, and second wash step according to Example 2, whether hybridization to a target nucleic acid had occurred or not was determined by measuring the impedance characteristics with respect to frequency. The result is shown in FIG. 14.

As can be inferred form FIG. 13, differential impedance signals between the uncleaved signal element (low impedance) and the cleaved signal element (high impedance) are provided to the detector.

While this invention has been particularly shown and described with reference to preferred embodiments thereof, it will be understood by those skilled in the art that various changes in form and details may be made therein without departing from the spirit and scope of the invention as defined by the appended claims.

INDUSTRIAL APPLICABILITY

As described above, the present invention provides a cleavage technique specifically responsive to a complementary double strand or single strand of nucleic acids, a nucleic acid hybridization assay method and device using the cleavable technique, and a diagnostic method and system capable of more accurately diagnosing many kinds of diseases through single nucleotide polymorphism (SNP) detection and expression profile determination that can be concurrently determined. In a preferred embodiment according to the present invention, the diagnostic system using the nucleic acid hybridization assay method and device based on the cleavage technique specifically responsive to the complementary double strand or single strand of nucleic acids can be modified for detection with standard laser-based detection systems, including CD-ROM readers and DVD readers, which enables self-diagnosis by patients at home without the need to go to a hospital. In addition, the present invention provides an assay device and method for detecting analytes using the nucleic acid hybridization assay device according to the present invention. This analyte assay device and method are useful in assaying for a number of discrete analytes with a test sample and a single analyte with multiple samples. The present invention also provides a remote diagnostic system providing convenience to both patients and doctors, in which information read from the assay device is digitized as software and transmitted to and received by patient and doctor through an existing communication network, such as the Internet.

What is claimed:

1. A nucleic acid hybridization assay method comprising:
contacting a nucleic acid hybridization assay device with a liquid sample including a target nucleic acid, wherein the nucleic acid hybridization assay device comprises a cleavable signal element comprising a capture probe of a single strand having a complementary sequence to the target nucleic acid; and a single stranded restriction probe not being complementary to the target nucleic acid, wherein one end of the single stranded restriction probe is ligated to the capture probe; and a solid support substrate attached to the other end of the single stranded restriction probe;
hybridizing the cleavable signal element to the target nucleic acid present in the liquid sample;
making the single stranded restriction probe into a double stranded restriction probe by DNA extension in the presence of a DNA polymerization solution using the target nucleic acid hybridized to the capture probe as a primer;
cleaving the double stranded restriction probe by a restriction enzyme and/or the double stranded cleavable signal element by a cleavage enzyme, wherein the double stranded restriction probe is cleaved by the restriction enzyme specifically responsive to a double strand with a particular sequence and/or the cleavage enzyme is specifically responsive to double stranded nucleic acids;
washing the nucleic acid hybridization assay device to remove the cleavable signal element cleaved by the restriction enzyme and/or the cleavage enzyme; and
detecting whether the uncleaved signal element or the cleaved signal element exists on the solid support substrate.

2. A nucleic acid hybridization assay method comprising:
contacting a nucleic acid hybridization assay device with a liquid sample including a target nucleic acid, wherein the nucleic acid hybridization assay device comprises a cleavable signal element comprising a capture probe of a single strand having a complementary sequence to the target nucleic acid; and a single stranded restriction probe not being complementary to the target nucleic acid, wherein one end of the single stranded restriction probe is ligated to the capture probe; and a solid support substrate attached to the other end of the single stranded restriction probe;

hybridizing the cleavable signal element to the target nucleic acid present in the liquid sample;

maintaining the single stranded restriction probe remain as a single strand after DNA extension except when the single stranded restriction probe is changed into a double stranded restriction probe by the DNA extension, where the DNA extension is done in the presence of a DNA polymerization solution using the target nucleic acid hybridized to the cleavable signal element as a primer;

cleaving the single stranded restriction probe by a cleavage enzyme after the DNA extension, wherein the cleavage enzyme is specifically responsive to the single stranded nucleic acids;

washing the nucleic acid hybridization assay device to remove the cleavable signal element cleaved by the cleavage enzyme; and detecting whether the uncleaved signal element or the cleaved signal element exists on the solid support substrate.

3. The nucleic acid hybridization assay method of claim 1 or 2, wherein the cleavage enzyme is a DNase or a nuclease.

4. The nucleic acid hybridization assay method of claim 1 or 2, further comprising contacting the cleavable signal element with a 3'-5' exonuclease solution before contacting with the DNA polymerization solution.

5. The nucleic acid hybridization assay method of claim 1 or 2, further comprising attaching a label to one end of the capture probe, or to the uncleaved signal element.

6. The nucleic acid hybridization assay method of claim 5, the label is one or more selected from the group consisting of a metal microsphere, a conducting polymer, a fluorescent dye, a magnetic microsphere, and a streptavidin-labeled microsphere.

7. The nucleic acid hybridization assay method of claim 1 or 2, wherein whether the uncleaved signal element or the cleaved signal element exists on the solid support substrate is detected by a detector, which is one or more selected from the group consisting of an optical device, an electrochemical device, a mass measurement device, or a capacitance and impedance measurement device.

8. The nucleic acid hybridization assay method of claim 1 or 2, wherein the solid support substrate has the shape of a circular disk.

9. The nucleic acid hybridization assay method of claim 8, wherein washing is performing by rotating the solid support substrate, or by applying an external electric field.

10. The nucleic acid hybridization assay method of claim 1 or 2, further comprising diagnosing remotely a patient by
a communication network;
a computer to which the nucleic acid hybridization assay device is connected; and
a software installed in the computer, wherein the software is capable of controlling access to the communication network and digitizing information read from the nucleic acid hybridization assay device, wherein the digitized information is transmitted to a doctor or a hospital, and the patient is provided with a prescription, through the communication network.

* * * * *

SEQUENCE LISTING

<160> NUMBER OF SEQ ID NOS: 4

<210> SEQ ID NO 1
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tgagacacca ggaattagat atcagtacaa tgt                               33

<210> SEQ ID NO 2
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ctaaatcaga tcctacatat aagtcatcca tgt                               33

<210> SEQ ID NO 3
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
tagatatcag tacaa                                                  15

<210> SEQ ID NO 4
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 4
tattcagtag gtaca                                                  15